(12) United States Patent
Keating et al.

(10) Patent No.: US 6,323,026 B1
(45) Date of Patent: Nov. 27, 2001

(54) **MUTATIONS IN THE *KCNE1* GENE ENCODING HUMAN MINK WHICH CAUSE ARRHYTHMIA SUSCEPTIBILITY THEREBY ESTABLISHING *KCNE1* AS AN LQT GENE**

(75) Inventors: Mark T. Keating; Michael C. Sanguinetti; Igor Splawski, all of Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/444,871

(22) Filed: Nov. 22, 1999

Related U.S. Application Data

(60) Division of application No. 09/135,020, filed on Aug. 17, 1998, which is a continuation-in-part of application No. 08/921,068, filed on Aug. 29, 1997, now abandoned, which is a continuation-in-part of application No. 08/739,383, filed on Oct. 29, 1996, now abandoned.

(60) Provisional application No. 60/094,477, filed on Jul. 29, 1998, and provisional application No. 60/019,014, filed on Dec. 22, 1995.

(51) Int. Cl.$^7$ ..................................................... C12N 15/12

(52) U.S. Cl. ........................... 435/325; 436/7.1; 436/7.2; 436/69.1; 436/252.3; 436/520.1; 536/23.5

(58) Field of Search ........................... 435/7.1, 7.2, 69.1, 435/252.3, 320.1; 536/23.5; 437/325

(56) References Cited

PUBLICATIONS

Ackerman, M.J. "The Long QT Syndrome: Ion Channel Diseases of the Heart"; *Mayo Clin. Proc.;* 1998; 73:250–269.

Attali, B., "A new wave for heart rhythms"; *Nature;* Nov. 7, 1996; 384:24–25.

Attali, B., et al. "A corticosteriod–induced gene expressing an "IsK–like" K$^+$ channel activity in *Xenopus oocytes*"; *Proc. Natl. Acad. Sci. USA;* Jun. 1995; 92;6092–6096.

Barhanin, J., et al. "K$_v$LQT1 and IsK (minK) proteins associate to form $I_{Ks}$ cardiac potassium current"; *Nature;* Nov. 7, 1996; 384:78–80.

Ben–Efraim, I., et al. "Secondary Structure and Membrane Localization of Synthetic Segments and a Truncated Form of the IsK (minK) Protein"; *Biochemistry;* 1994; 33:6966–6973.

Brahmajothi, M.V. et al. "In Situ Hybridization Reveals Extensive Diversity of K$^+$ Channel mRNA in Isolated Ferret Cardiac Myocytes"; *Cir. Res.;* 1996; 78:1083–1089.

Busch, A.E. amd Suessbrich, H. "Role of the $I_{SK}$ protein in the $I_{minK}$ channel complex"; *Trends Pharmacol. Sci.;* Jan. 1997; 18:26–29.

Chevillard, C. et al. "Localization of a Potassium Channel Gene (KCNE1) to 21q22.1–q22.2 by in Situ Hybridization and Somatic Cell Hybridization"; *Genomics;* 1993; 15:243–245.

Duggal, P. et al. "Mutation of the Gene for IsK Associated With Both Jervell and Lange–Nielsen and Romano–Ward Forms of Long–QT Syndrome"; 1998; *Ciruclation;* 97:142–146.

Freeman, L.C. and Kass, R.S. "Expression of a Minimal K$^+$ Channel Protein in Mammalian Cells and Immunolocalization in Guinea Pig Heart"; 1993; *Cir. Res.;* 73:968–973.

Goldstein, S.A.N. and Miller, C. "Site–Specific Mutations in a Minimal Voltage–Dependent K$^+$ Channel Alter Ion Selectivity and Open–Channel Block"; Sep. 1991; *Neuron.;* 7:403–408.

Iwai, M. et al. "Characterization of Gene Organization and Generation of Heterogeneous mRNA Species of Rat $I_{SK}$ Protein"; 1990; *J. Biochem.;* 108:200–206.

Kaczmarek, L.K. and Blumenthal, E.M. "Properties and Regulation of the minK Potassium Channel Protein"; Jul. 1997; *Physiological Reviews;* 77(3):627–641.

Lai. L–P et al. Polymorphisms of the gene encoding a human minimal potassium ion channel (minK); 1994; *gene;* 151:339–340.

McDonald, T.V. et al. "A minK–HERG complex regulates the cardiac potassium current $I_{Kr}$"; Jul. 1997; *Nature;* 388:289–292.

Mercer, E.A.J. et al. "Synthetic putative transmembrane region of minimal potassium channel protein(minK) adopts an α–helical conformation in phospholipid memebranes"; 1997; *Biochem. J,;* 325:475–479.

Muria, T. et al. "Molecular Cloning and Sequence Analysis of Human Genomic DNA Encoding a Novel Membrane Protein which Exhibits a Slowly Activating Potassium Channel Activity"; May 30, 1989; *Biochem. Biophys. Res. Commun.;* 161(1):176–181.

Romey, G. et al. "Molecular Mechanism and Functional Significance of the MinK Control of the KvLQT1 Channel Activity"; Jul. 4, 1997; *J. Biol. Chem.;* 272:16713–16716.

Sanguinetti, M.C. et al. "Coassembly of K$_v$LQT1 and minK (IsK) proteins to form cardiac $I_{Ks}$ potassium channel"; Nov. 7, 1996; *Nature;* 384:80–83.

Sanguinetti, M.C. and Jurkiewicz, N.K. "Delayed rectfier outward K$^+$ current is composed of two currents in guinea pig atrial cells"; 1991; *American Journal of Physiology;* 260(1):H393–H399.

*Primary Examiner*—John Ulm
(74) *Attorney, Agent, or Firm*—Rothwell, Figg, Ernst & Manbeck

(57) ABSTRACT

The genomic structure including the sequence of the intron/ exon junctions is disclosed for KVLQT1 and KCNE1 which are genes associated with long QT syndrome. Additional sequence data for the two genes ARE also disclosed. Also disclosed are newly found mutations in KVLQT1 which result in long QT syndrome. The intron/exon junction sequence data allow for the design of primer pairs to amplify and sequence across all of the exons of the two genes. This can be used to screen persons for the presence of mutations which cause long QT syndrome. Assays can be performed to screen persons for the presence of mutations in either the DNA or proteins. The DNA and proteins may also be used in assays to screen for drugs which will be useful in treating or preventing the occurrence of long QT syndrome.

18 Claims, 26 Drawing Sheets

OTHER PUBLICATIONS

Schulze–Bahr, E. et al. "KCNE1 mutations cause Jervell and Lange–Nielsen syndrome"; Nov. 1997; *Nat. Genet.;* 17:267–268.

Splawski, I. et al. "Mutations in the hminK gene cause long QT syndrome and suppress $I_{Ks}$ function"; Nov. 1997; *Nature Genetics;* 17:338–340.

Tai, K–K et al. "MinK potassium Channels Are Heteromultimeric Complexes"; Jan. 1997; *J. Biol. Chem.;* 272:1654–1658.

Takumi, T. et al. "Cloning of a Membrane Protein That Induces a Slow Voltage–Gated Potassium Current"; Nov. 1988; *Science;* 242:1042–1045.

Takumi, T. et al. "Alteration of Channel Activities and Gating by Mutations of Slow $I_{SK}$ Potassium Channel"; Nov. 1991; *J. Biol. Chem.;* 266:22192–22198.

Tesson, F. et al. "Exclusion of KCNE1 (IsK) as a Candiate Gene for Jervell and Lange–Nielsen Syndrome"; 1996; *J. Mol. Cell Cardiol.;* 28:2051–2055.

Tyson, J. et al. "IsK and KvLQT1: mutation in either of the two subunits of the slow component of the delayed rectifier potassium channel can cause Jervell and Lange–Nielsen syndrome"; 1997; *Human Molecular Genetics;* 6:2179–2185.

Veldkamp, M. et al. "Delayed Rectifier Channels in Human Ventricular Myocytes"; Dec. 1995; *Circulation;* 92:3497–350.

Vetter, D.E. et al. "Inner Ear Defects Induced by Null Mutation of the isk Gene"; Dec. 1996; *Neuron;* 17:1251–1264.

Wang, K–W and Goldstein, S.A.N. "Subunit Composition of MinK Potassium Channels"; Jun. 1995; *Neuron;* 14:1303–1309.

Wang, K–W et al. "MinK Residues Line a Potassium Channel Pore"; Mar. 1996; *Neuron;* 16:571–577.

Wang, Q. et al. "Positional cloning of a novel potassium channel gene: KVLQT1 mutations cause cardiac arrhythmias"; Jan. 1996; *Nature Genetics;* 12:17–23.

Wilson, G.G. et al. "Channels in activation gating of $I_{sK}$ potassium currents brought about by mutations in the transmembrane sequence"; 1994; *FEBS Letters;* 353:251–254.

Yang, T. et al. "Anti–minK Antisense Decreases the Amplitude of the Rapidly Activating Cardiac Delayed Rectfier $K^+$ Current"; Dec. 1995; *Circulation Research;* 77:1246–1253.

Yang, T. et al. "$K^+$ Current and $K^+$ Channel mRNA in Cultured Atrial Cardiac Myocytes (AT–1 Cells)"; Nov. 1994; *Circulation Research;* 75:870–878.

```
KVLQT1    1   FLIVLVCLIFSVLSTIEQYAALATGT.................LFWMEIVLVFFGTEYVVRLWSAGCRSKYVGLMGRLRFARKPISIIDLIVVASMVLCVG.............SKGQVFAT-95
              :|::  :||:: :|  :||         :|||   :  :|   ||:     :|||  : :||:|   |  ||::            |  |  :
DMSHAKE1  237 ILLSIVIFCLETLPEFKHYKVFNTTNGTKLEEDEVPDITDPFFLIETLCIIWFTFELTVRFLACP......NKLNFCRDVMNVIDIIAIIPYFITLATVAEEDTLNLPKAPVSPQDKSSNQAMSL-358
                                       S1                                                    S2                                     S3

SAIRGIRFLQILRMLHVDRQGGTWRLLGSVVFIHRQELITTLYIGFLGLIFSSYFVVLAEKDAVNESGRVEFGSYADALMWGVTVTITIGYGDKVPQTWVGKTIASCFSVFAISFFALPAGILGSGFAL-224
              :|  || ::|::|:|:: :||   :|           ||    :| :|:|::|     |:  :|   :|  ::||:|||:||||::|||| |  | :|    :||  :||
              AILRVIRLVVFRIFRLFKLSRHSKGLQILGRTLKASMRELGLLIFFLFIGVLFSSAVFAEAGSENSF....FKSIPDAFWWAVTMTTVGYGDMTPVGFWGKIVGSLCVVAGVLTIALPVPVIVSNFNY-483
                             S4                              S5                              Pore                    S6

FIG. 3
```

```
CTGCCCCCTCCGGCCCCGCCCCGAGCGCCCGGGCTGGGCCGGCAGCGGCCCCCGCGGCGGGGCTGGCAGCAGTGGCTGCC-81
CGCACTGCGCCCGGGCGCTCGCCTTCGCTGCAGCTCCCGGTGCCGCCGCTCGGGCCGGCCCCCCGGCAGGCCCTCCTCGTT-162
ATGGCCGCGGCCTCCTCCCCGCCCAGGGCCGAGAGGAAGCGCTGGGGTTGGGGCCGCCTGCCAGGCGCCCGGCGGGGCAGC-243
 M  A  A  A  S  S  P  P  R  A  E  R  K  R  W  G  W  G  R  L  P  G  A  R  R  G  S -27
GCGGGCCTGGCCAAGAAGTGCCCCTTCTCGCTGGAGCTGGCGGAGGGCGGCCCGGCGGGCGGCGCGCTCTACGCGCCCATC-324
 A  G  L  A  K  K  C  P  F  S  L  E  L  A  E  G  G  P  A  G  G  A  L  Y  A  P  I -54
GCGCCCGGCGCCCCAGGTCCCGCGCCCCCTGCGTCCCCGGCCGCGCCCGCCGCGCCCCAGTTGCCTCCGACCTTGGCCCG-405
 A  P  G  A  P  G  P  A  P  P  A  S  P  A  A  P  A  A  P  P  V  A  S  D  L  G  P -81
CGGCCGCCGGTGAGCCTAGACCCGCGCGTCTCCATCTACAGCACGCGCCGCCCGGTGTTGGCGCGCACCCACGTCCAGGGC-486
 R  P  P  V  S  L  D  P  R  V  S  I  Y  S  T  R  R  P  V  L  A  R  T  H  V  Q  G -108
                                                              ▼
CGCGTCTACAACTTCCTCGAGCGTCCCACCGGCTGGAAATGCTTCGTTTACCACTTCGCCGTCTTCCTCATCGTCCTGGTC-567
 R  V  Y  N  F  L  E  R  P  T  G  W  K  C  F  V  Y  H  F  A  V  F  L  I  V  L  V -135
                                              ▼ S1
TGCCTCATCTTCAGCGTGCTGTCCACCATCGAGCAGTATGCCGCCCTGGCCACGGGGACTCTCTTCTGGATGGAGATCGTG-648
 C  L  I  F  S  V  L  S  T  I  E  Q  Y  A  A  L  A  T  G  T  L  F  W  M  E  I  V -162
                         S2
CTGGTGGTGTTCTTCGGGACGGAGTACGTGGTCCGCCTCTGGTCCGCCGGCTGCCGCAGCAAGTACGTGGGCCTCTGGGGG-729
 L  V  V  F  F  G  T  E  Y  V  V  R  L  W  S  A  G  C  R  S  K  Y  V  G  L  W  G -189
                              ▼
CGGCTGCGCTTTGCCCGGAAGCCCATTTCCATCATCGACCTCATCGTGGTCGTGGCCTCCATGGTGGTCCTCTGCGTGGGC-810
 R  L  R  F  A  R  K  P  I  S  I  I  D  L  I  V  V  V  A  S  M  V  V  L  C  V  G -216
                            ▼       S3
TCCAAGGGGCAGGTGTTTGCCACGTCGGCCATCAGGGGCATCCGCTTCCTGCAGATCCTGAGGATGCTACACGTCGACCGC-891
 S  K  G  Q  V  F  A  T  S  A  I  R  G  I  R  F  L  Q  I  L  R  M  L  H  V  D  R -243
                    S4                              ▼
CAGGGAGGCACCTGGAGGCTCCTGGGCTCCGTGGTCTTCATCCACCGCCAGGAGCTGATAACCACCCTGTACATCGGCTTC-972
 Q  G  G  T  W  R  L  L  G  S  V  V  F  I  H  R  Q  E  L  I  T  T  L  Y  I  G  F -270
CTGGGCCTCATCTTCTCCTCGTACTTTGTGTACCTGGCTGAGAAGGACGCGGTGAACGAGTCAGGCCGCGTGGAGTTCGGC-1053
 L  G  L  I  F  S  S  Y  F  V  Y  L  A  E  K  D  A  V  N  E  S  G  R  V  E  F  G -297
          S5                  ▼
AGCTACGCAGATGCGCTGTGGTGGGGGGTGGTCACAGTCACCACCATCGGCTATGGGGACAAGGTGCCCCAGACGTGGGTC-1134
 S  Y  A  D  A  L  W  W  G  V  V  T  V  T  T  I  G  Y  G  D  K  V  P  Q  T  W  V -324
                Pore                                              ▼
GGGAAGACCATCGCCTCCTGCTTCTCTGTCTTTGCCATCTCCTTCTTTGCGCTCCCAGCGGGGATTCTTGGCTCGGGGTTT-1215
 G  K  T  I  A  S  C  F  S  V  F  A  I  S  F  F  A  L  P  A  G  I  L  G  S  G  F -351
                              S6                                            ▼
GCCCTGAAGGTGCAGCAGAAGCAGAGGCAGAAGCACTTCAACCGGCAGATCCCGGCGGCAGCCTCACTCATTCAGACCGCA-1296
 A  L  K  V  Q  Q  K  Q  R  Q  K  H  F  N  R  Q  I  P  A  A  A  S  L  I  Q  T  A -378
TGGAGGTGCTATGCTGCCGAGAACCCCGACTCCTCCACCTGGAAGATCTACATCCGGAAGGCCCCCCGGAGCCACACTCTG-1377
 W  R  C  Y  A  A  E  N  P  D  S  S  T  W  K  I  Y  I  R  K  A  P  R  S  H  T  L -405
                                      ▼
CTGTCACCCAGCCCCAAACCCAAGAAGTCTGTGGTGGTAAAGAAAAAAAAGTTCAAGCTGGACAAAGACAATGGGGTGACT-1458
 L  S  P  S  P  K  P  K  K  S  V  V  V  K  K  K  K  F  K  L  D  K  D  N  G  V  T -432
CCTGGAGAGAAGATGCTCACAGTCCCCCATATCACGTGCGACCCCCCAGAAGAGCGGCGGCTGGACCACTTCTCTGTCGAC-1539
 P  G  E  K  M  L  T  V  P  H  I  T  C  D  P  P  E  E  R  R  L  D  H  F  S  V  D -459
              ▼
GGCTATGACAGTTCTGTAAGGAAGAGCCCAACACTGCTGGAAGTGAGCATGCCCCATTTCATGAGAACCAACAGCTTCGCC-1620
 G  Y  D  S  S  V  R  K  S  P  T  L  L  E  V  S  M  P  H  F  M  R  T  N  S  F  A -486
                                                      ▼
GAGGACCTGGACCTGGAAGGGGAGACTCTGCTGACACCCATCACCCACATCTCACAGCTGCGGGAACACCATCGGGCCACC-1701
 E  D  L  D  L  E  G  E  T  L  L  T  P  I  T  H  I  S  Q  L  R  E  H  H  R  A  T -513
                                              ▼
ATTAAGGTCATTCGACGCATGCAGTACTTTGTGGCCAAGAAGAAATTCCAGCAAGCGCGGAAGCCTTACGATGTGCGGGAC-1782
 I  K  V  I  R  R  M  Q  Y  F  V  A  K  K  K  F  Q  Q  A  R  K  P  Y  D  V  R  D -540
                                                              ▼
GTCATTGAGCAGTACTCGCAGGGCCACCTCAACCTCATGGTGCGCATCAAGGAGCTGCAGAGGAGGCTGGACCAGTCCATT-1863
 V  I  E  Q  Y  S  Q  G  H  L  N  L  M  V  R  I  K  E  L  Q  R  R  L  D  Q  S  I -567
```

FIG. 5A

```
GGGAAGCCCTCACTGTTCATCTCCGTCTCAGAAAAGAGCAAGGATCGCGGCAGCAACACGATCGGCGCCCGCCTGAACCGA-1944
 G  K  P  S  L  F  I  S  V  S  E  K  S  K  D  R  G  S  N  T  I  G  A  R  L  N  R  -594
GTAGAAGACAAGGTGACGCAGCTGGACCAGAGGCTGGCACTCATCACCGACATGCTTCACCAGCTGCTCTCCTTGCACGGT-2025
 V  E  D  K  V  T  Q  L  D  Q  R  L  A  L  I  T  D  M  L  H  Q  L  L  S  L  H  G  -621
GGCAGCACCCCCGGCAGCGGCGGCCCCCCCAGAGAGGGCGGGGCCCACATCACCCAGCCCTGCGGCAGTGGCGGCTCCGTC-2106
 G  S  T  P  G  S  G  G  P  P  R  E  G  G  A  H  I  T  Q  P  C  G  S  G  G  S  V  -648
GACCCTGAGCTCTTCCTGCCCAGCAACACCCTGCCCACCTACGAGCAGCTGACCGTGCCCAGGAGGGGCCCCGATGAGGGG-2187
 D  P  E  L  F  L  P  S  N  T  L  P  T  Y  E  Q  L  T  V  P  R  R  G  P  D  E  G  -675
TCCTGAGGAGGGGATGGGGCTGGGGGATGGGCCTGAGTGAGAGGGGAGGCCAAGAGTGGCCCCACCTGGCCCTCTCTGAAG-2268
 S  *                                                                              -676
GAGGCCACCTCCTAAAAGGCCCAGAGAGAAGAGCCCCACTCTCAGAGGCCCCAATACCCCATGGACCATGCTGTCTGGCAC-2349
AGCCTGCACTTGGGGGCTCAGCAAGGCCACCTCTTCCTGGCCGGTGTGGGGCCCCGTCTCAGGTCTGAGTTGTTACCCCA-2430
AGCGCCCTGGCCCCCACATGGTGATGTTGACATCACTGGCATGGTGGTTGGGACCCAGTGGCAGGGCACAGGGCCTGGCCC-2511
ATGTATGGCCAGGAAGTAGCACAGGCTGAGTGCAGGCCCACCCTGCTTGGCCCAGGGGGCTTCCTGAGGGGAGACAGAGCA-2592
ACCCCTGGACCCCAGCCTCAAATCCAGGACCCTGCCAGGCACAGGCAGGGCAGGACCAGCCCACGCTGACTACAGGGCCAC-2673
CGGCAATAAAAGCCCAGGAGCCCATTTGGAGGGCCTGGGCCTGGCTCCCTCACTCTCAGGAAATGCTGACCCATGGGCAGG-2754
AGACTGTGGAGACTGCTCCTGAGCCCCCAGCTTCCAGCAGGAGGGACAGTCTCACCATTTCCCCAGGGCACGTGGTTGAGT-2835
GGGGGGAACGCCCACTTCCCTGGGTTAGACTGCCAGCTCTTCCTAGCTGGAGAGGAGCCCTGCCTCTCCGCCCCTGAGCCC-2916
ACTGTGCGTGGGGCTCCCGCCTCCAACCCCTCGCCCAGTCCCAGCAGCCAGCCAAACACACAGAAGGGGACTGCCACCTCC-2997
CCTTGCCAGCTGCTGAGCCGCAGAGAAGTGACGGTTCCTACACAGGACAGGGGTTCCTTCTGGGCATTACATCGCATAGAA-3078
ATCAATAATTTGTGGTGATTTGGATCTGTGTTTTAATGAGTTTCACAGTGTGATTTTGATTATTAATTGTGCAAGCTTTTC-3159
CTAATAAACGTGGAGAATCAC(A)n                                                          -3180
```

FIG. 5B

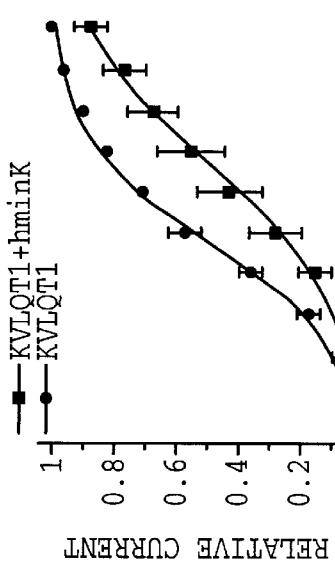
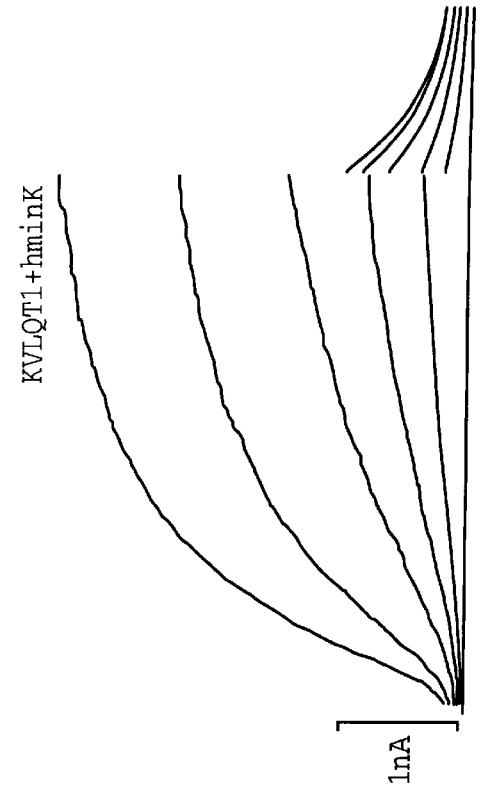
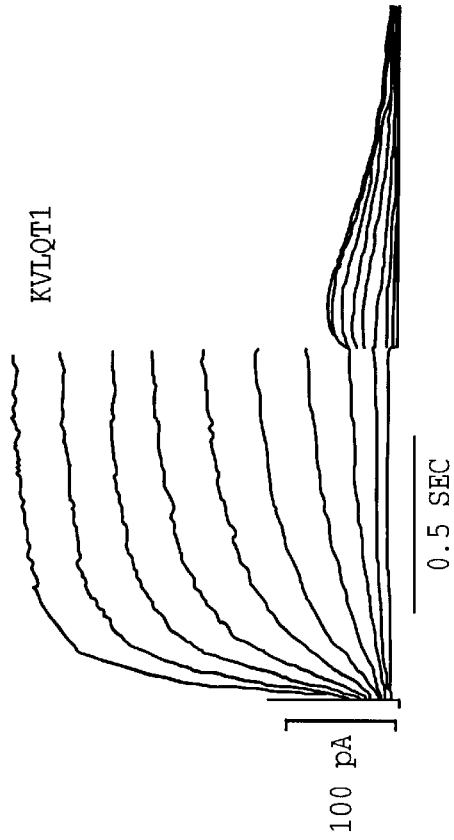
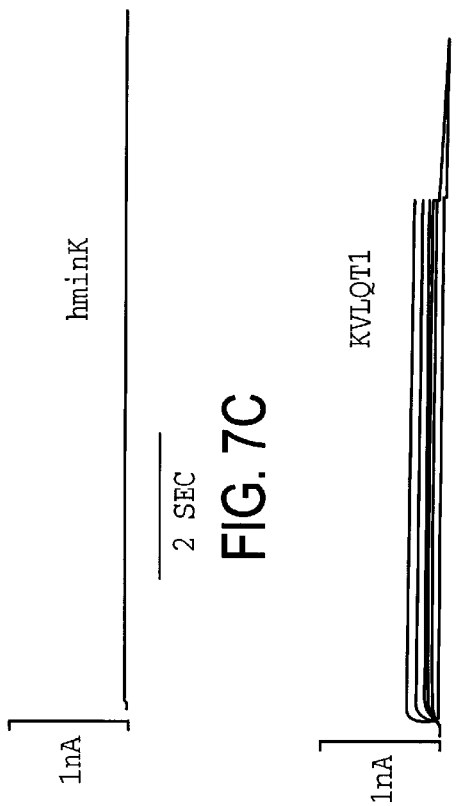

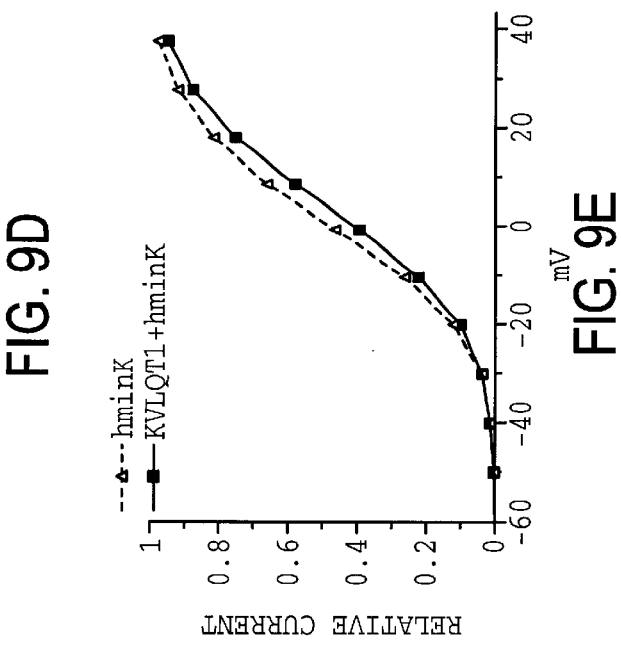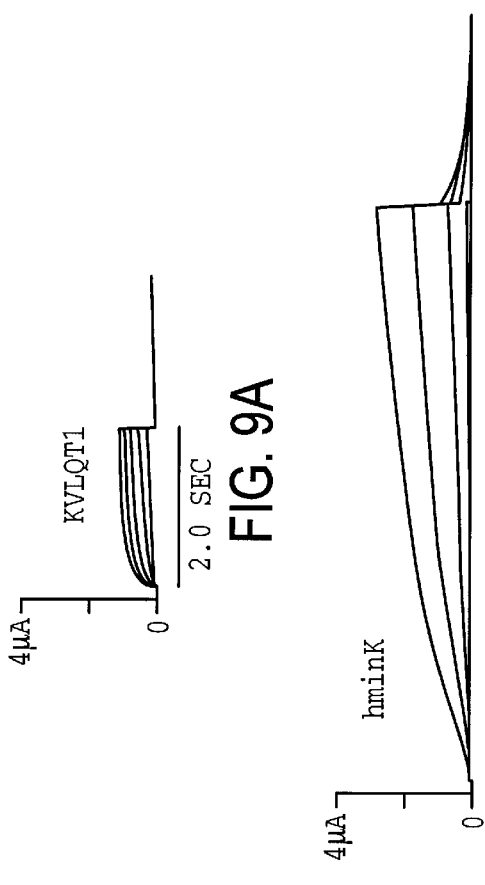

| | |
|---|---|
| XENOPUS | MNENAINSLYEAIPLPQDGSSNGQRQEDRQANSFELKRETLVATDPPRPT |
| | |
| HUMAN | QGRVYNFLERPTGWKCFVYHFAVFLIVL |
| | \|\|\|\|\|\|\|\|\|\|\|\|\|\|\|\|\|\|\|\|\| \|\|\|\|\|\| |
| XENOPUS | INLDPRVSIYSGRRPLFSRTNIQGRVYNFLERPTGWKCFVYHFTVFLIVL |
| | S1_____       _____S2_____ |
| HUMAN | VCLIFSVLSTIEQYAALATGTLFWMEIVLVVFFGTEYVVRLWSAGCRSKY |
| | \|\|\|\|\|\|\|\|\|\| \|\| \|\|\| \|\|\|\|\|\|\|\|\|\|\|\|\| \|\|\|\|\|\|\|\|\|\|\|\|\| |
| XENOPUS | ICLIFSVLSTIQQYNNLATETLFWMEIVLVVFFGAEYVVRLWSAGCRSKY |
| | _____S3_____       _____S4_____ |
| HUMAN | VGLWGRLRFARKPISIIDLIVVVASMVVLCVGSKGQVFATSAIRGIRFLQ |
| | \| \|\|\|\|\|\|\|\|\|\|\|\| \|\|\|\|\|\|\|\|\|   \|\|\|\|\|\| \|\|\|\|\|\|\|\|\|\|\|\|\|\|\| |
| XENOPUS | VGVWGRLRFARKPISVIDLIVVVASVIVLCVGSNGQVFATSAIRGIRFLQ |
| | _____                           _____S5_____ |
| HUMAN | ILRMLHVDRQGGTWRLLGSVVFIHRQELITTLYIGFLGLIFSSYFVYLAE |
| | \|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\| |
| XENOPUS | ILRMLHVDRQGGTWRLLGSVVFIHRQELITTLYIGFLGLIFSSYFVYLAE |
| | _____Pore_____ |
| HUMAN | KDAVNESGRVEFGSYADALWWGVVTVTTIGYGDKVPQTWVGKTIASCFSV |
| | \|\|\|   \|\|   \|\|\|\|\|\|\|\|\|\|\|\|\|\|\|\|\|\|\|\|\|\|\|\|\|\|\|\|\|\| \|\|\|\|\|\|\|\|\|\| |
| XENOPUS | KDAIDSSGEYQFGSYADALWWGVVTVTTIGYGDKVPQTWIGKTIASCFSV |
| | ___S6___ |
| HUMAN | FAISFFALPAGILGSGFALKVQQKQRQKHFNRQIPAAASLIQTAWRCYAA |
| | \|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\|\| |
| XENOPUS | FAISFFALPAGILGSGFALKVQQKQRQKHFNRQIPAAASLIQTAWRCYAA |
| | |
| HUMAN | ENPDSSTWKIYIRKAPRSHTLLSPSPKPKKSVVVKKKKFKLDKDNGVTPG |
| | \|\|\|\|\| \|\|\|\|\|\|\|\| \|\|\|   \|\|\|\| |
| XENOPUS | ENPDSATWKIYIRKQSRNHHIMSPSP |
| | |
| HUMAN | EKMLTVPHITCDPPEERRLDHFSVDGYDSSVRKSPTLLEVSMPHFMRTNS |
| | |
| HUMAN | FAEDLDLEGETLLTPITHISQLREHHRATIKVIRRMQYFVAKKKFQQARK |
| | |
| HUMAN | PYDVRDVIEQYSQGHLNLMRVIKELQRRLDQSIGKPSLFISVSEKSKDRG |
| | |
| HUMAN | SNTIGARLNRVEDKVTQLDQRLALITDMLHQLLSLHGGSTPGSGGPPREG |
| | |
| HUMAN | GAHITQPCGSGGSVDPELFLPSNTLPTYEQLTVPRRGPDEGS |

FIG. 10

```
ACACCCGGCTCTCTCGGCATCTCAGACCCGGGAAAAATCCCTCTGCTTTCTCTGGCCAGTTTCACACAATCATCAGGTGAG-81
                                    ▼
CCGAGGATCCATTGGAGGAAGGCATTATCTGTATCCAGAGGAAATAGCCAAGGATATTCAGAGGTGTGCCTGGGAAGTTTG-162
AGCTGCAGCAGTGGAACCTTAATGCCCAGGATGATCCTGTCTAACACCACAGCGGTGACGCCCTTTCTGACCAAGCTGTGG-243
                             M  I  L  S  N  T  T  A  V  T  P  F  L  T  K  L  W  -17
CAGGAGACAGTTCAGCAGGGTGGCAACATGTCGGGCCTGGCCCGCAGGTCCCCCCGCAGCGGTGACGGCAAGCTGGAGGCC-324
 Q  E  T  V  Q  Q  G  G  N  M  S  G  L  A  R  R  S  P  R  S  G  D  G  K  L  E  A  -44
CTCTACGTCCTCATGGTACTGGGATTCTTCGGCTTCTTCACCCTGGGCATCATGCTGAGCTACATCCGCTCCAAGAAGCTG-405
 L  Y  V  L  M  V  L  G  F  F  G  F  F  T  L  G  I  M  L  S  Y  I  R  S  K  K  L  -71
GAGCACTCGAACGACCCATTCAACGTCTACATCGAGTCCGATGCCTGGCAAGAGAAGGACAAGGCCTATGTCCAGGCCCGG-486
 E  H  S  N  D  P  F  N  V  Y  I  E  S  D  A  W  Q  E  K  D  K  A  Y  V  Q  A  R  -98
GTCCTGGAGAGCTACAGGTCGTGCTATGTCGTTGAAAACCATCTGGCCATAGAACAACCCAACACACACCTTCCTGAGACG-567
 V  L  E  S  Y  R  S  C  Y  V  V  E  N  H  L  A  I  E  Q  P  N  T  H  L  P  E  T  -125
AAGCCTTCCCCATGAACCCCACCACTGGCTAAACTGGACACCTCCTGCTGGNNNNNNAGATTTTCTAATCACATTCCTCTCA-648
 K  P  S  P  *
TACTCTTTATTGTGATGGATACCACTGGATTTCTTTTTGGCTGTTGTAANGGGTGAGGGGTGGATTAATGACACTGTTTCA-729
CTGTTTCTCTAAAATCACGTTCTTTTGTGATAGACTGTCAGTGGTTCCCCCATATCTGTCCCTGCCTTGCTAAATTTAGCA-810
GAATCCCTGAGGACATGGCCTCTGAGAATAGCAGCTGCATTTCCCAGACTCCCTTGCAGCTAGCAAGGTTGTGTGACTAAG-891
CCCTGGCCAGTAGGCATGGAAGTGAAGACTGTAATGTCCAAGTAATCCTTGGAAAGAAAAGAACGTGCCCTTAACTAACTT-972
TGTCCTGCTTCCCAGTGGCTGGATGTGGAGGAGGTGGAGAGCAGTTATGAGACTGGGAAAGTTCGGGGCACTCAAAGAGCC-1053
ACACACATCTGGGCCTGGGCGACGTGATCCTCCTTACCACCCACCAGGCCAGATTTACAGGAGAGAGAAATCCACTCCAC-1134
TCTTCCTTAAGCCACTGTTATTCTGATCTCTGTTAAGGTCGCAGAATCAATGCCCTTACTGATACACCTACCTTATAGGAC-1215
TGAACCTAAAGGCATGACATTTCCATACTTGTCACAAGCACACACTGATTCTGCCCTTGTCACTTCTGTGCTCACTCTTGT-1269
GGCTCTATCCTCCTCCTGCCCTTCCGCCTTCCACTCCTCCCTTGCACCCATCCTGCACACATCTCCCTGAAAACACACAGG-1377
CACATACACTCATATACATAGACACACATACACACCTCAATCTAGAAAGAACTTGCTTTGTACAGGGCTGAGATGGAGGAG-1458
AAAAAAATGCCCCCTTCAGAATGCATACCAAGGGGAAGGTGCTCGGTCACTGTGGGAGCAGGGAAAGGTGCCCCCACTCCC-1539
CGAGAGCCAGGGGAAGGAGTGGCTCTGGGCAGAGAGGGACACATAGCACTGGGGTGGCAGGTCCTTTTGAGGTGATGGGCC-1620
GGTTTTGTGAGATGAATTGTATCCCCCAAAAAGACAGGTACCTTCAATGTGACCTAATTGGGAAATAGAGTCTTTGCAGAT-1701
G(A)n                                                                           -1702
```

FIG. 18

MUTATIONS IN THE *KCNE1* GENE ENCODING HUMAN MINK WHICH CAUSE ARRHYTHMIA SUSCEPTIBILITY THEREBY ESTABLISHING *KCNE1* AS AN LQT GENE

CROSS REFERENCE TO RELATED APPLICATIONS

The present invention is a divisional application of Ser. No. 09/135,020, filed Aug. 17, 1998, which is a continuation-in-part of application Ser. No. 08/921,068 filed Aug. 29, 1997 now abandoned, which is a continuation-in-part of application Ser. No. 08/739,383 filed Oct. 29, 1996, now abandoned, which is related to application Ser. No. 60/019,014 filed Dec. 22, 1995, and the present invention is also related to provisional application Ser. No. 60/094,477 filed Jul. 29, 1998, all of which are incorporated herein by reference.

This application was made with Government support under Grant Nos. RO1 HL48074, and P50-HL52338-02 (SCOR), funded by the National Institutes of Health, Bethesda, Md. The federal government may have certain rights in this invention.

BACKGROUND OF THE INVENTION

The present invention is directed to genes and gene products associated with long QT syndrome (LQT) and to a process for the diagnosis of LQT. LQT is diagnosed in accordance with the present invention by analyzing the DNA sequence of the KVLQT1 or KCNE1 gene of an individual to be tested and comparing the respective DNA sequence to the known DNA sequence of a normal KVLQT1 or KCNE1 gene. Alternatively, the KVLQT1 or KCNE1 gene of an individual to be tested can be screened for mutations which cause LQT. Prediction of LQT will enable practitioners to prevent this disorder using existing medical therapy. This invention is further directed to the discovery that the KVLQT1 and KCNE1 (also known as minK) proteins coassemble to form a cardiac $I_{Ks}$ potassium channel. This knowledge can be used to coexpress these two proteins in a cell and such a transformed cell can be used for screening for drugs which will be useful in treating or preventing LQT. The invention is further directed to mutations in the human KCNE1 gene (which gene encodes human minK protein) which have been discovered in families with LQT.

The publications and other materials used herein to illuminate the background of the invention or provide additional details respecting the practice, are incorporated by reference, and for convenience are respectively grouped in the appended List of References.

Cardiac arrhythmias are a common cause of morbidity and mortality, accounting for approximately, 11% of all natural deaths (Kannel, 1987; Willich et al., 1987). In general, presymptomatic diagnosis and treatment of individuals with life-threatening ventricular tachyarrhythmias is poor, and in some cases medical management actually increases the risk of arrhythmia and death (Cardiac Arrhythmia Suppression Trial II Investigators, 1992). These factors make early detection of individuals at risk for cardiac arrhythmias and arrhythmia prevention high priorities.

Both genetic and acquired factors contribute to the risk of developing cardiac arrhythmias. Long QT syndrome (LQT) is an inherited cardiac arrhythmia that causes abrupt loss of consciousness, syncope, seizures and sudden death from ventricular tachyarrhythmias, specifically torsade de pointes and ventricular fibrillation (Ward, 1964; Romano, 1965; Schwartz et al., 1975; Moss et al., 1991). This disorder usually occurs in young, otherwise healthy individuals (Ward, 1964; Romano, 1965; Schwartz et al., 1975). Most LQT gene carriers manifest prolongation of the QT interval on electrocardiograms, a sign of abnormal cardiac repolarization (Vincent et al., 1992)). The clinical features of LQT result from episodic cardiac arrhythmias, specifically repolarization-related ventricular tachyarrhythmias like torsade de pointes, named for the characteristic undulating nature of the electrocardiogram in this arrhythmia and ventricular fibrillation (Schwartz et al., 1975; Moss and McDonald, 1971). Torsade de pointes may degenerate into ventricular fibrillation, a particularly lethal arrhythmia. Although LQT is not a common diagnosis, ventricular arrhythmias are very common; more than 300,000 United States citizens die suddenly every year (Kannel, et al., 1987; Willich et al., 1987) and, in many cases, the underlying mechanism may be aberrant cardiac repolarization. LQT, therefore, provides a unique opportunity to study life-threatening cardiac arrhythmias at the molecular level.

Both inherited and acquired forms of LQT have been defined. Acquired LQT and secondary arrhythmias can result from cardiac ischemia, bradycardia and metabolic abnormalities such as low serum potassium or calcium concentration (Zipes, 1987). LQT can also result from treatment with certain medications, including antibiotics, antihistamines, general anesthetics, and, most commonly, antiarrhythmic medications (Zipes, 1987). Inherited forms of LQT can result from mutations in at least five different genes. In previous studies, LQT loci were mapped to chromosome 11p15.5 (KVLQT1 or LQT1) (Keating et al., 1991a; Keating et al., 1991b), 7q35–36 (HERG or LQT2), 3p21–24 (SCN5A or LQT3) (Jiang et al., 1994). Of these, the most common cause of inherited LQT is KVLQT1. Our data indicate that mutations in this gene are responsible for more than 50% of inherited LQT. Recently, a fourth LQT locus (LQT4) was mapped to 4q25–27 (Schott et al., 1995). Also, KCNE1 (LQT5) has been associated with long QT syndrome (Splawski et al., 1997b; Duggal et al., 1998). These genes encode ion channels involved in generation of the cardiac action potential. Mutations can lead to channel dysfunction and delayed myocellular repolarization. Because of regional heterogeneity of channel expression with the myocardium, the aberrant cardiac repolarization creates a substrate for arrhythmia. KVLQT1 and KCNE1 are also expressed in the inner ear (Neyroud et al., 1997; Vetter et al., 1996). We and others demonstrated that homozygous or compound heterozygous mutations in each of these genes can cause deafness and the severe cardiac phenotype of the Jervell and Lange-Nielsen syndrome (Neyroud et al., 1997; Splawski et al., 1997a; Schultze-Bahr et al., 1997; Tyson et al., 1997). Loss of functional channels in the ear apparently disrupts the production of endolymph, leading to deafness.

Presymptomatic diagnosis of LQT is currently based on prolongation of the QT interval on electrocardiograms. QTc (QT interval corrected for heart rate; Bazzett, 1920) greater than 0.44 second has traditionally classified an individual as affected. Most LQT patients, however, are young, otherwise healthy individuals, who do not have electrocardiograms. Moreover, genetic studies have shown that QTc is neither sensitive nor specific (Vincent et al., 1992). The spectrum of QTc intervals for gene carriers and non-carriers overlaps, leading to misclassifications. Non-carriers can have prolonged QTc intervals and be diagnosed as affected. Conversely, some LQT gene carriers have QTc intervals of $\leq 0.44$ second but are still at increased risk for arrhythmia. Correct presymptomatic diagnosis is important for effective, gene-specific treatment of LQT.

Autosomal dominant and autosomal recessive forms of this disorder have been reported. Autosomal recessive LQT (also known as Jervell and Lange-Nielsen syndrome) has been associated with congenital neural deafness; this form of LQT is rare (Jervell and Lange-Nielsen, 1957). Autosomal dominant LQT (Romano-Ward syndrome) is more common, and is not associated with other phenotypic abnormalities (Romano et al., 1963; Ward, 1964). A disorder very similar to inherited LQT can also be acquired, usually as a result of pharmacologic therapy (Schwartz et al., 1975; Zipes, 1987).

The data have implications for the mechanism of arrhythmias in LQT. Two hypotheses for LQT have previously been proposed (Schwartz et al., 1994). One suggests that a predominance of left autonomic innervation causes abnormal cardiac repolarization and arrhythmias. This hypothesis is supported by the finding that arrhythmias can be induced in dogs by removal of the right stellate ganglion. In addition, anecdotal evidence suggests that some LQT patients are effectively treated by β-adrenergic blocking agents and by left stellate ganglionectomy (Schwartz et al., 1994). The second hypothesis for LQT-related arrhythmias suggests that mutations in cardiac-specific ion channel genes, or genes that modulate cardiac ion channels, cause delayed myocellular repolarization. Delayed myocellular repolarization could promote reactivation of L-type calcium channels, resulting in secondary depolarizations (January and Riddle, 1989). These secondary depolarizations are the likely cellular mechanism of torsade de pointes arrhythmias (Surawicz, 1989). This hypothesis is supported by the observation that pharmacologic block of potassium channels can induce QT prolongation and repolarization-related arrhythmias in humans and animal models (Antzelevitch and Sicouri, 1994). The discovery that one form of LQT results from mutations in a cardiac potassium channel gene supports the myocellular hypothesis.

In theory, mutations in a cardiac sodium channel gene could cause LQT. Voltage-gated sodium channels mediate rapid depolarization in ventricular myocytes, and also conduct a small current during the plateau phase of the action potential (Attwell et al., 1979). Subtle abnormalities of sodium channel function (e.g., delayed sodium channel inactivation or altered voltage-dependence of channel inactivation) could delay cardiac repolarization, leading to QT prolongation and arrhythmias. In 1992, Gellens and colleagues cloned and characterized a cardiac sodium channel gene, SCN5A (Gellens et al., 1992). The structure of this gene was similar to other, previously characterized sodium channels, encoding a large protein of 2016 amino acids. These channel proteins contain four homologous domains (DI–DIV). each of which contains six putative membrane spanning segments (S1–S6). SCN5A was recently mapped to chromosome 3p21, making it an excellent candidate gene for LQT3 (George et al., 1995), and this gene was then proved to be associated with LQT3 (Wang et al., 1995a).

In 1994, Warmke and Ganetzky identified a novel human cDNA, human ether a-go-go related gene (HERG, Warmke and Ganetzky 1994). HERG was localized to human chromosome 7 by PCR analysis of a somatic cell hybrid panel (Warmke and Ganetzky, 1994) making it a candidate for LQT2. It has predicted amino acid sequence homology to potassium channels. HERG was isolated from a hippocampal cDNA library by homology to the Drosophila ether a-go-go gene (eag), which encodes a calcium-modulated potassium channel (Bruggemann et al., 1993). HERG is not the human homolog of eag, however, sharing only ~50% amino acid sequence homology. HERG has been shown to be associated with LQT2 (Curran et al., 1995).

LQT1 was found to be linked with the gene KVLQT1 (Q. Wang et al., 1996). Sixteen families with mutations KVLQT1 were identified and characterized and it was shown that in all sixteen families there was complete linkage between LQT1 and KVLQT1. KVLQT1 was mapped to chromosome 11p15.5 making it a candidate gene for LQT1. KVLQT1 encodes a protein with structural characteristics of potassium channels, and expression of the gene as measured by Northern blot analysis demonstrated that KVLQT1 is most strongly expressed in the heart. One intragenic deletion and ten different missense mutations which cause LQT were identified in KVLQT1. These data define KVLQT1 as a novel cardiac potassium channel gene and show that mutations in this gene cause susceptibility to ventricular tachyarrhythmias and sudden death.

It was known that one component of the $I_{Ks}$ channel is minK, a 130 amino acid protein with a single putative transmembrane domain (Takumi et al., 1988; Goldstein and Miller, 1991; Hausdorff et al., 1991; Takumi et al., 1991; Busch et al., 1992; Wang and Goldstein, 1995; K W Wang et al., 1996). The size and structure of this protein made it unlikely that minK alone forms functional channels (Attali et al., 1993; Lesage et al., 1993). Evidence is presented that KVLQT1 and minK coassemble to form the cardiac $I_{Ks}$ potassium channel. This was published by Sanguinetti et al. (1996b). $I_{Ks}$ dysfunction is a cause of cardiac arrhythmia. It was later shown that mutations in KCNE1 (which encodes minK) also can result in LQT (Splawski et al., 1997b).

SUMMARY OF THE INVENTION

The present invention teaches the genomic structure of the LQT genes KVLQT1 and KCNE1. This includes a teaching of the intron/exon boundaries. Also disclosed are additional sequence data not previously reported for both genes as well as mutations in KVLQT1 and KCNE1 which are associated with LQT. Analysis of the KVLQT1 or KCNE1 gene will provide an early diagnosis of subjects with LQT. The diagnostic method comprises analyzing the DNA sequence of the KVLQT1 and/or KCNE1 gene of an individual to be tested and comparing it with the DNA sequence of the native, non-variant gene. In a second embodiment, the KVLQT1 or KCNE1 gene of an individual to be tested is screened for mutations which cause LQT. The ability to predict LQT will enable physicians to prevent the disease with medical therapy such as beta blocking agents.

It is further demonstrated that KVLQT1 and KCNE1 (minK) coassemble to form a cardiac $I_{Ks}$ potassium channel. $I_{Ks}$ dysfunction is a cause of cardiac arrhythmia. The knowledge that these two proteins coassemble to form the $I_{Ks}$ channel is useful for developing an assay to screen for drugs which are useful in treating or preventing LQT1. By coexpressing both genes in a cell such as an oocyte it is possible to screen for drugs which have an effect on the $I_{Ks}$ channel, both in its wild-type and in its mutated forms. This knowledge is also useful for the analysis of the KCNE1 gene for an early diagnosis of subjects with LQT. The diagnostic methods are performed as noted above for KVLQT1 and/or KCNE1.

Marker order (top to bottom) is: Tel-HRAS-D11S922-TH-D11S1318-D11S454-D11S860-D11S12-Cen. The accuracy of haplotypes was ensured using genotypes from additional chromosome 11p15.5 markers. Inferred genotypes are shown in brackets. Disease chromosomes are indicated by boxes and recombination events are indicated with solid horizontal lines. Recombination events affecting disease chromosomes occur in individuals: IV-22, IV-25, V-6, V-17, V-24, V-34, VI-13, VI-14 and VI-16. Recombination events occurring in non-disease chromosomes are not indicated. KVLQT1 is an SSCP conformer within KVLQT1 identified by primers 5 and 6; this conformer was only identified in K1532 and represents a disease-associated mutation (allele 2 is the mutant allele). Haplotype analyses indicate that KVLQT1 is located between flanking markers D11S922 and D11S454.

Figure 2:
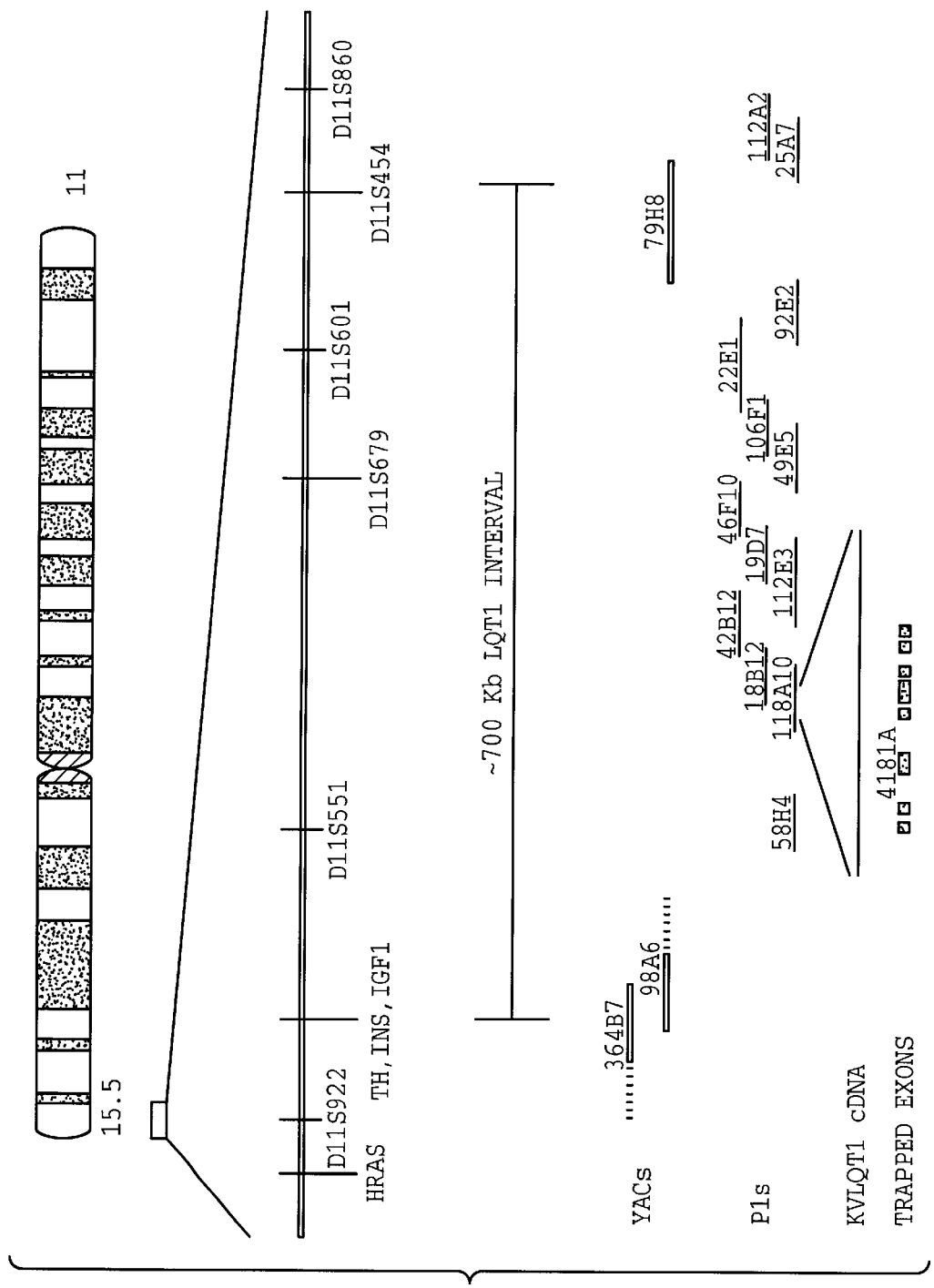

FIG. 2. Physical map of the LQT1 region. Ideogram of chromosome 11 indicates the approximate location of LQT1 (11p15.5). The location of polymorphic markers and some cosmids are indicated by vertical lines on the map. Refined genetic mapping places LQT1 between TH and D11S454. The distance between TH and D11S454 was estimated by pulsed field gel analyses as <700 kb. A physical map of the minimal set of overlapping YAC and P1 clones is shown. The locations of the KVLQT1 cDNA and trapped exons are indicated. Dashed lines in YACs indicate chimerism.

FIG. 3. Alignment of the S1–S6 region of KVLQT1 with Drosophila Shaker potassium channel, DMSHAKE1 (SHA) (Pongs et al., 1988). Identity (|) and similarity (:) are indicated. The 3 separate fragments of KVLQT1 are in order: SEQ ID NO:107, SEQ ID NO:108 and SEQ ID NO:109. The 3 separate fragments of DMSHAKE1 are in order: SEQ ID NO:110, SEQ ID NO:111 and SEQ ID NO:119.

Figure 4:
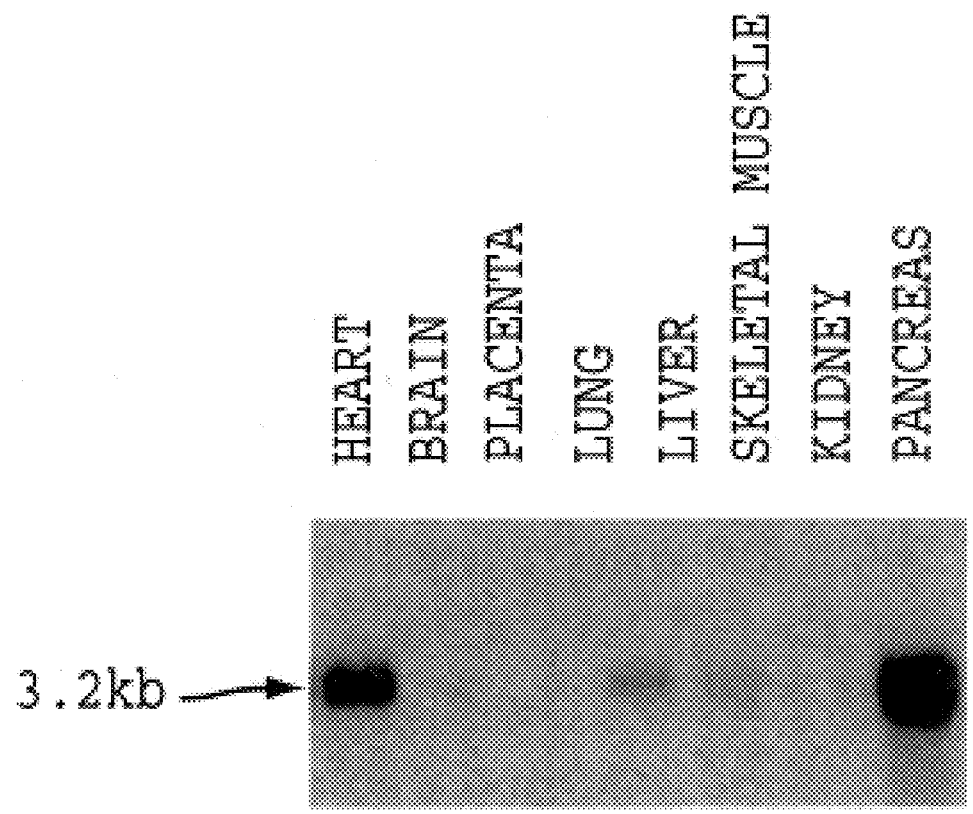

FIG. 4. Northern analysis indicating expression of KVLQT1 in human heart, placenta, lung, kidney and pancreas.

FIGS. 5A–5B. Genomic organization of KVLQT1 coding and 5' and 3' untranslated regions. Positions of the introns are indicated with arrowheads. The six putative transmembrane segments (S1 to S6) and the putative pore region (Pore) are underlined. The stop codon is denoted by an asterisk. The nucleotide sequence of FIGS. 5A–5B is SEQ ID NO:1. The amino acid sequence of FIGS. 5A–5B is SEQ ID NO:2.

Figure 6:
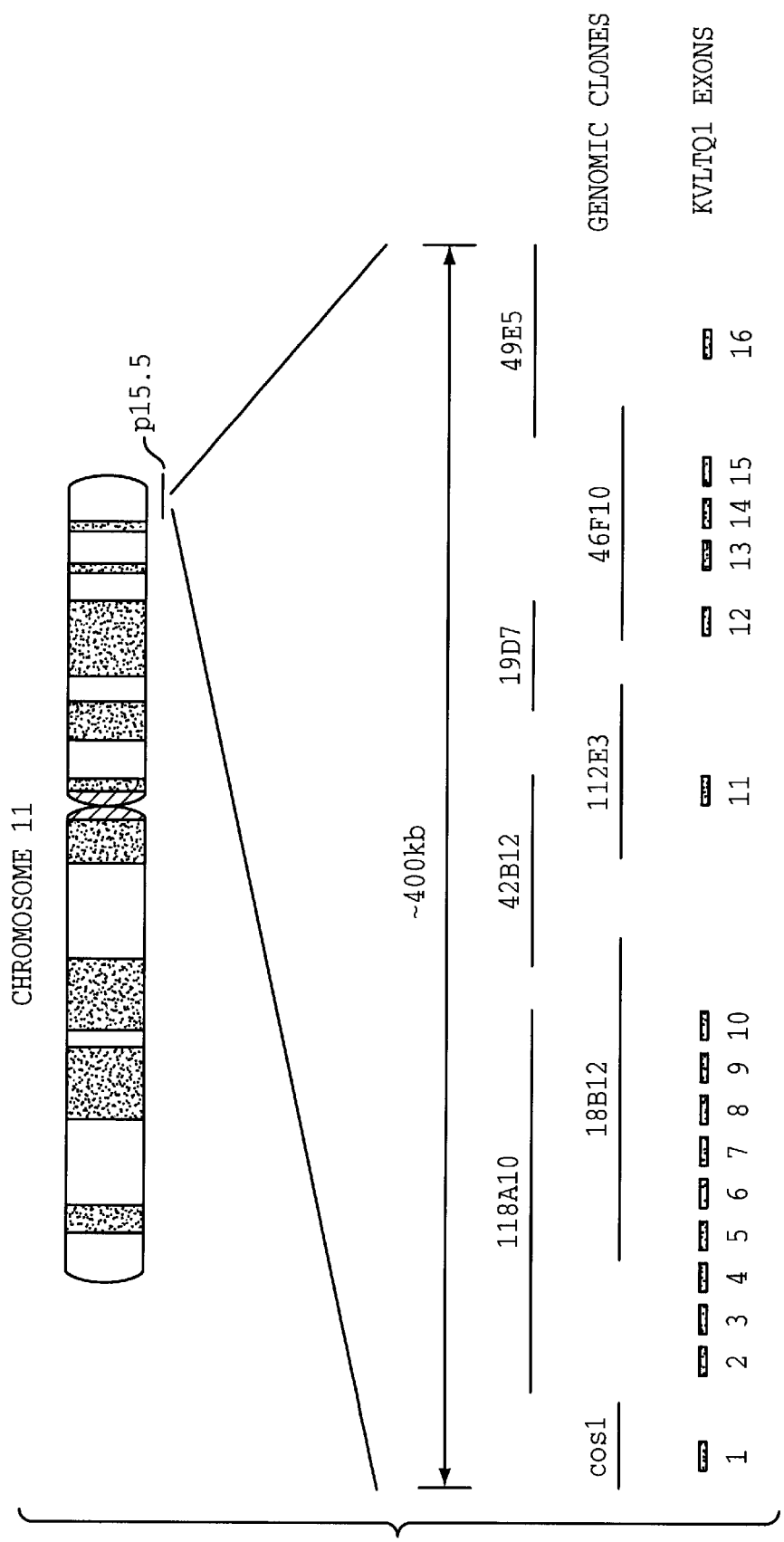

FIG. 6. Physical map and exon organization of KVLQT1. The genomic region of KVLQT1 encompasses approximately 400 kilobases. Physical map of the minimal contig of overlapping P1 clones and the cosmid containing exon 1 is shown. The location of KVLQT1 exons relative to genomic clones is indicated. Sizes of exons and distances are not drawn to scale.

FIG. 7A–7E. KVLQT1 and hminK coexpression in CHO cells induces a current nearly identical to cardiac $I_{Ks}$. A) KVLQT1 currents recorded during 1 sec depolarizing pulses to membrane potentials of –50 to +40 mV, applied from a holding potential of –80 mV. Tail currents were measured at –70 mV. B) Normalized isochronal activation curves for cells transfected with KVLQT1 (n=6; 1 sec pulses) or KVLQT1 and KCNE1 (n=7; 7.5 sec pulses). C–E) Currents recorded during 7.5 sec pulses to –40, –20, –10, 0, +20 and +40 mV in cells transfected with KCNE1 (C), KVLQT1 (D) or KVLQT1 and KCNE1 (E). Tail currents were measured at –70 mV in D, and at –50 mV in C and E. The amplitude of steady state KVLQT1 current at +40 mV was 0.37±0.14 nA (n=6). In cells cotransfected with KVLQT1 and KCNE1, time-dependent current during a 7.5-s pulse to +40 mV was 1.62±0.39 nA (n=7).

Figure 8B:
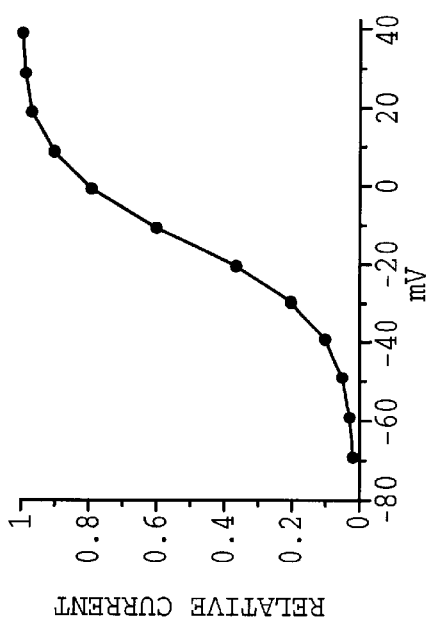
Figure 8C:
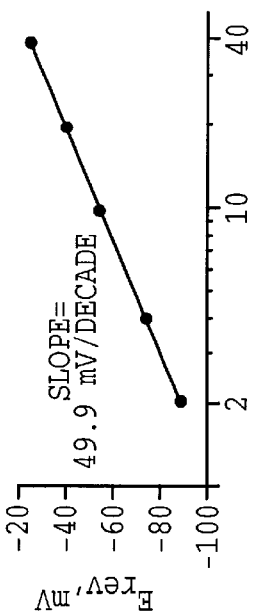
Figure 8A:
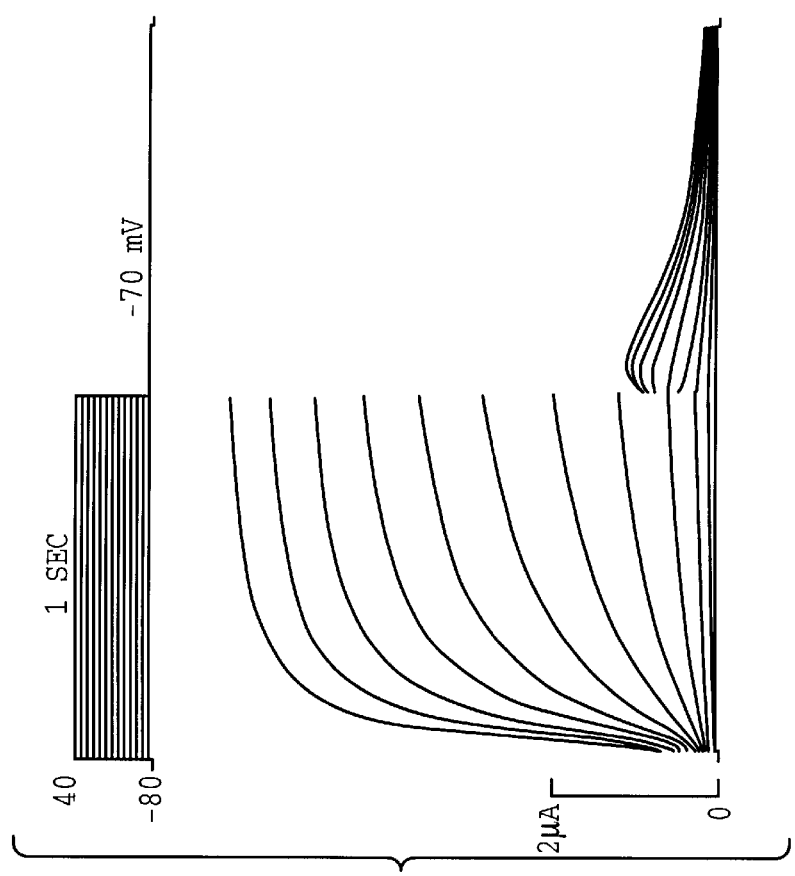

FIGS. 8A–8C. Expression of KVLQT1 in Xenopus oocytes. A) Currents recorded in an oocyte injected with 12.5 ng KVLQT1 cRNA. Pulses were applied in 10 mV increments from –70 to +40 mV. B) Isochronal (1s) activation curve for KVLQT1 current. The $V_{1/2}$ was –14.0±0.2 mV and the slope factor was 11.2±0.2 mV (n=9). C) The relationship of $E_{rev}$ versus log[$K^+$]$_e$ was fit with a linear function and had a slope of 49.9±0.4 mV (n=6–7 oocytes per point). Tail currents were measured at several voltages after 1.6 sec prepulses to +10 mV.

FIGS. 9A–9E. Coexpression of KVLQT1 and hminK suggests the presence of a KVLQT1 homologue in Xenopus oocytes. Currents were recorded at –40, –20, 0, +20 and +40 mV in oocytes injected with either 5.8 ng KVLQT1 (FIG. 9A), 1 ng KCNE1 (FIG. 9B), or co-injected with both cRNAs (FIG. 9C). FIG. 9D shows current-voltage relationships measured using 2 sec pulses for KVLQT1, and 7.5 sec pulses for hminK, or KVLQT1 and hminK (n=20 cells for each condition). For oocytes injected with 60 pg or 1 ng of KCNE1 cRNA, $I_{sK}$ at +40 mV was 2.11±0.12 μA and 2.20±0.18 μA. FIG. 9E shows normalized isochronal activation curves for oocytes injected with KCNE1 ($V_{1/2}$= 2.4±0.3 mV; slope=11.4±0.3 mV; n=16) or co-injected with KVLQT1 and KCNE1 cRNA ($V_{1/2}$=6.2±0.3 mV; slope= 12.3±0.2 mV; n=20).

FIG. 10. Comparison of a partial human and a partial Xenopus KVLQT1 amino acid sequence. Vertical lines indicate identical residues. The Xenopus amino acid sequence is SEQ ID NO:113 and the human amino acid sequence is SEQ ID NO:114.

Figures 11A, 11B:
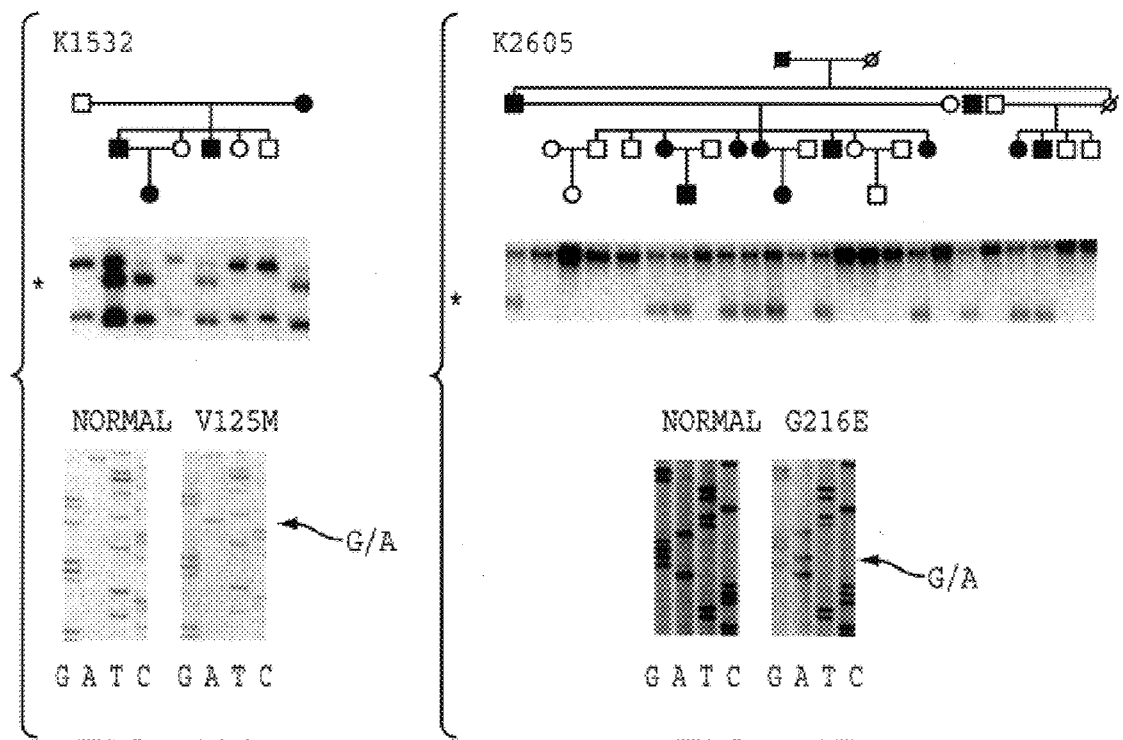
Figures 11C, 11D:
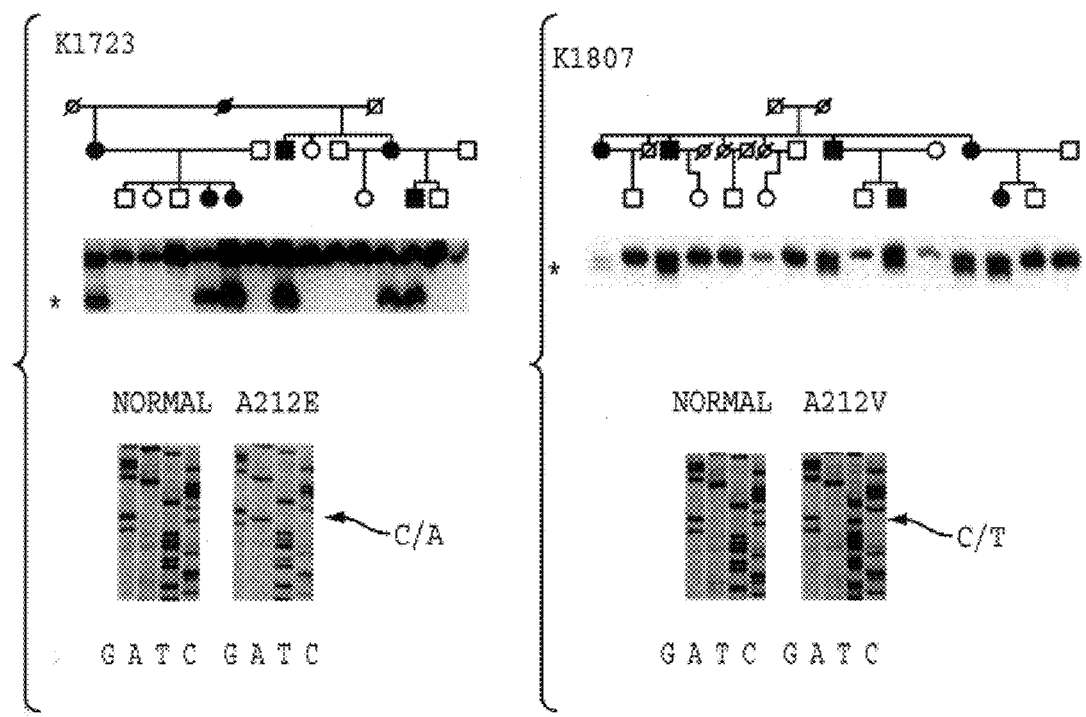

FIGS. 11A–11D. KVLQT1 missense mutations cosegregate with LQT in kindreds K1532 (FIG. 11A), K2605 (FIG. 11B), K1723 (FIG. 11C) and K1807 (FIG. 11D). The results of SSCP analyses with primer pair 5–6 (K1532), primer pair 9–10 (K1723, K1807), and primer pair 11–12 (K2605) are shown below each pedigree. Aberrant SSCP conformers (indicated by *) cosegregate with LQT in each kindred. For K1532, only eight of the 217 individuals are shown. Because aberrant SSCP conformers cosegregating with LQT in K161 and K162 were identical to the aberrant conformer defined in K1807, results for these kindreds are not shown. Results of DNA sequence analyses of the normal (left) and aberrant (right) conformers are shown below each pedigree.

Figure 12A:
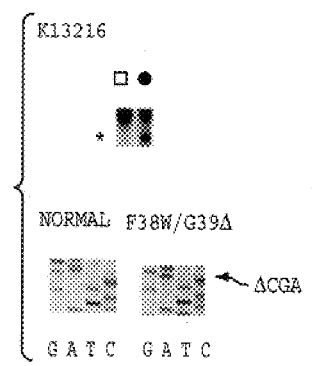
Figure 12B:
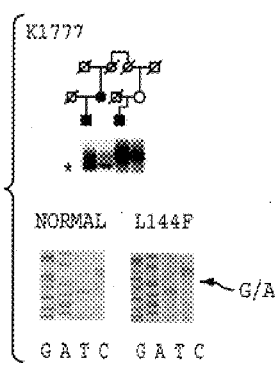
Figure 12C:
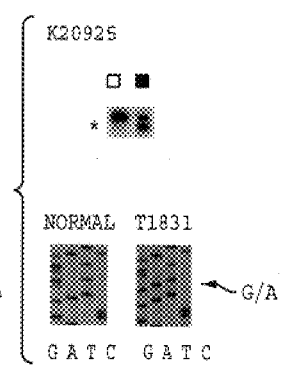
Figure 12D:
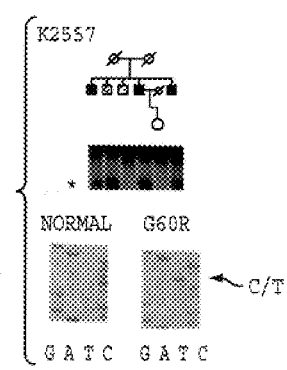
Figure 12E:
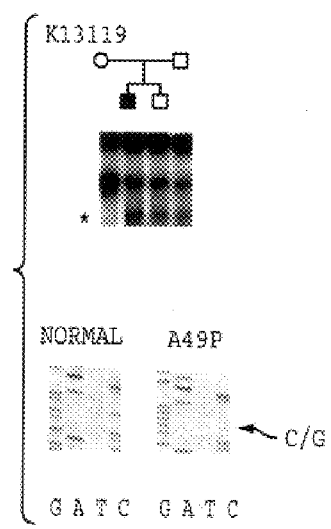
Figure 12F:
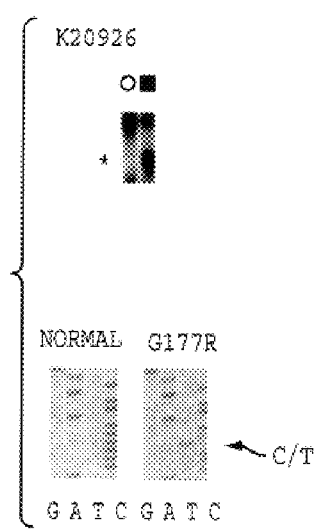
Figure 12G:
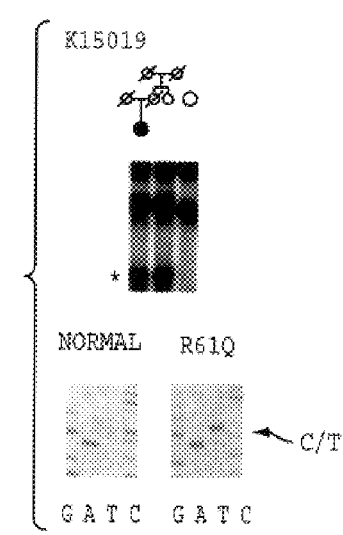
Figures 12H, 12I:
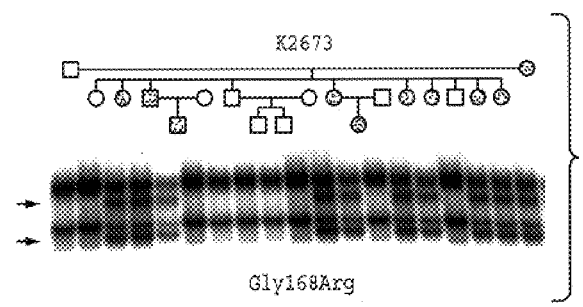
Figures 12J, 12K, 12L, 12M, 12N, 12O:
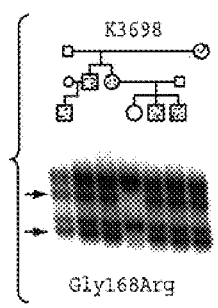

FIGS. 12A–12O. KVLQT1 intragenic deletions and missense mutations associated with LQT in kindreds K13216 (FIG. 12A), K1777 (FIG. 12B), K20925 (FIG. 12C), K2557 (FIG. 12D), K13119 (FIG. 12E), K20926 (FIG. 12F), K15019 (FIG. 12G), K2625 (FIG. 12H), K2673 (FIG. 12I), K3698 (FIG. 12J), K19187 (FIG. 12K), K22709 (FIG. 12L), K2762 (FIG. 12M), K3401 (FIG. 12N) and K2824 (FIG. 12O). Affected individuals are indicated by filled circles (females) and squares (males). Unaffected individuals are indicated with empty symbols and uncertain individuals are either gray or stippled. The results of SSCP analyses with printer pair 1–2 (K13216, K2557, K13119, K15019), primer pair 7–8 (K1777, K20926), and primer pair 9–10 (K20925) are should below each pedigree in FIGS. 12A–12G (see Table 5 for primer pairs). Because aberrant SSCP conformers cosegregating with LQT in K2050, K163 and K164 were identical to the aberrant conformers defined in K1723 and K1807, results for these kindreds are not shown. For FIGS. 12A–12G, results of DNA sequence analyses of the normal (left) and aberrant (right) conformers are shown below each pedigree and the sequences shown are on the antisense strand. For FIGS. 12H–12O the aberrant SSCP conformers are indicated by an arrow.

Figure 13A:
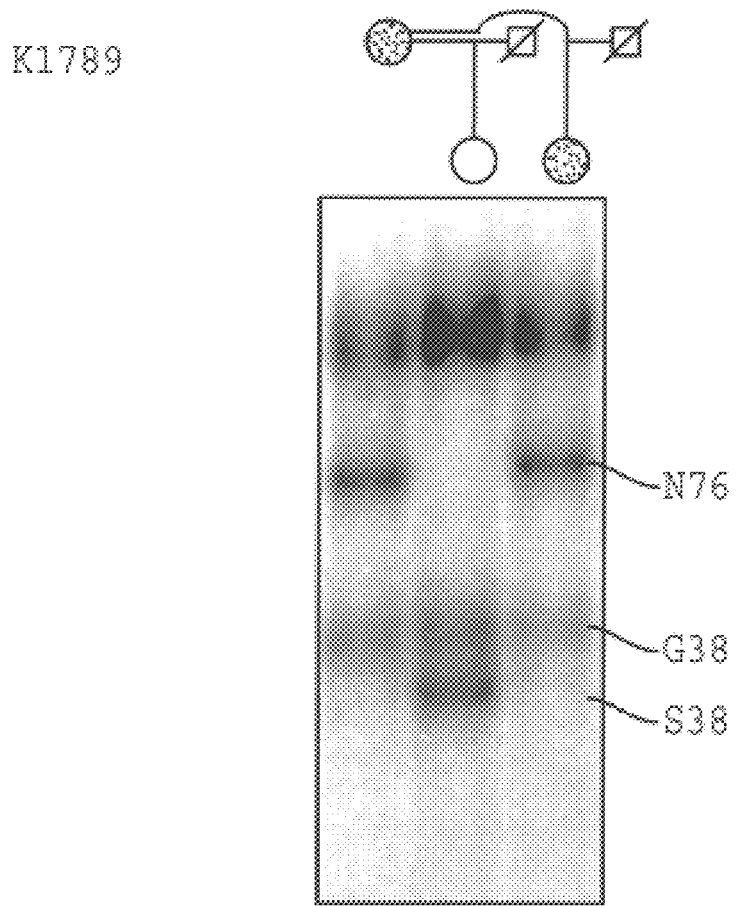
Figure 13B:
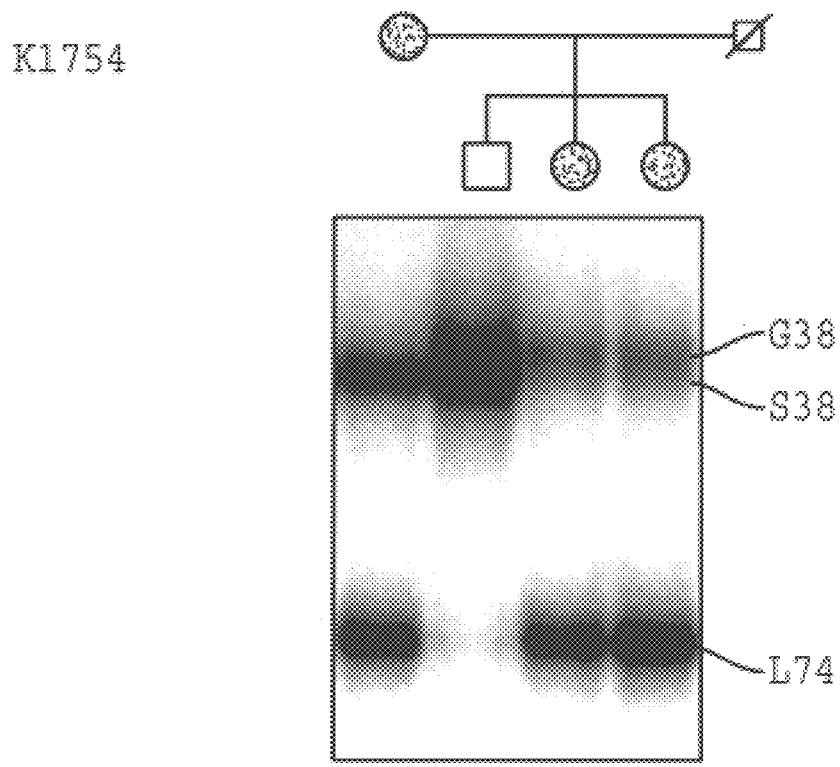
Figure 13C:
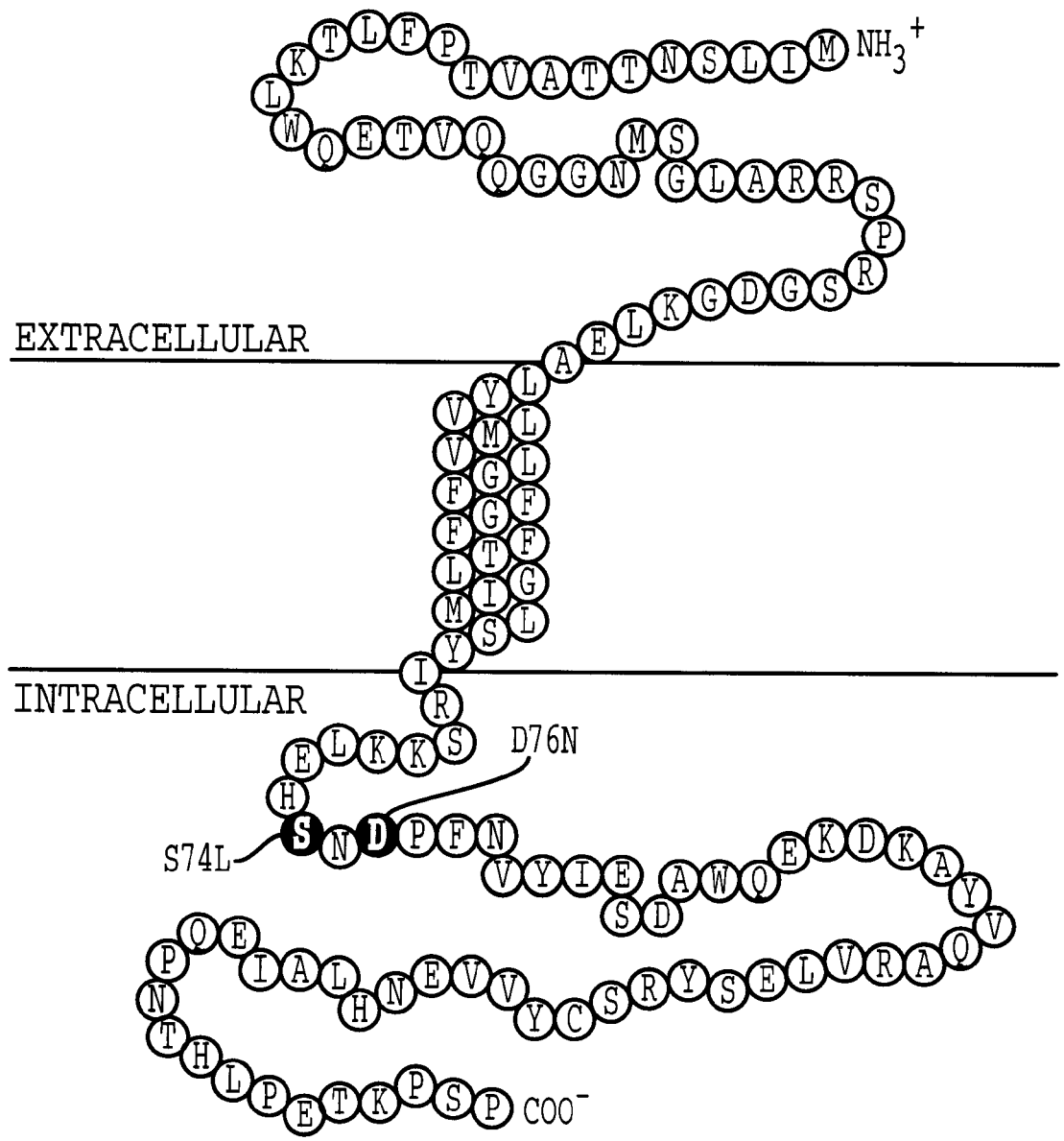

FIGS. 13A–13C. KCNE1 mutations associated with LQT. Pedigree structure for LQT kindreds 1789 (FIG. 13A) and 1754 (FIG. 13B). Affected individuals are indicated by filled circles (females) or squares (males). Unaffected individuals are indicated by open symbols. Deceased individuals are identified by a diagonal slash. Aberrant SSCP conformers that cosegregate with the disease are shown below each pedigree. A common polymorphism (G38S) that is not related to LQT is also detected by these primers. The effect of mutations on hminK protein sequence is indicated. FIG. 13C is a schematic representation of hminK protein showing the location of LQT-associated mutations.

Figure 14B:
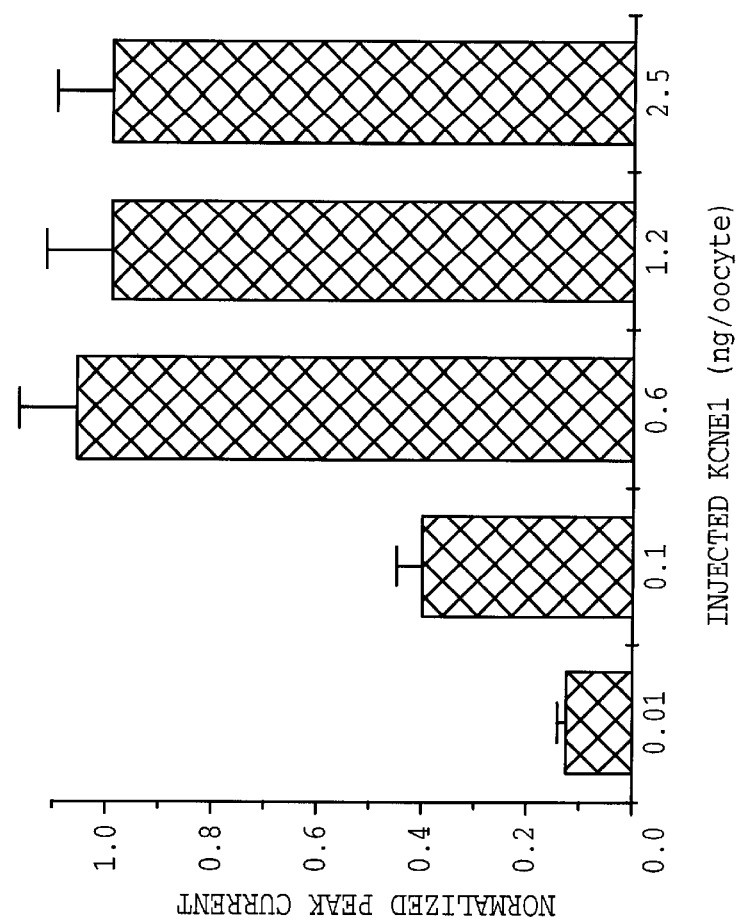
Figure 14A:
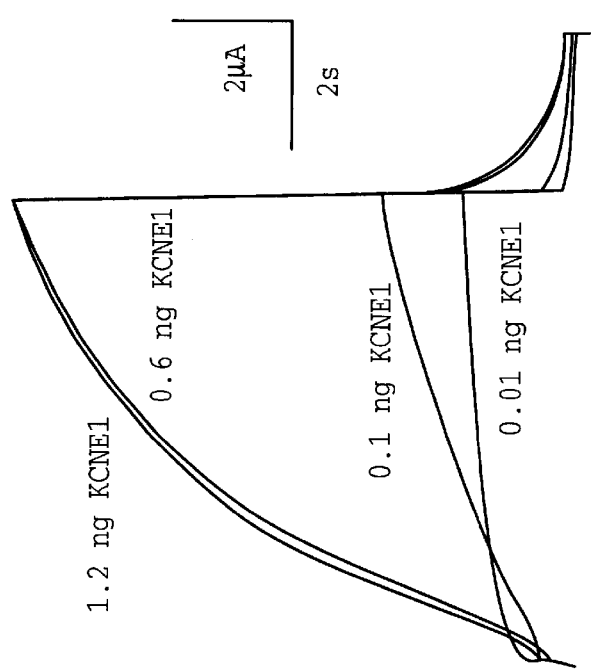

FIGS. 14A–14B. Magnitude of $I_{Ks}$ varies as a function of injected KCNE1 cRNA. A) Representative current tracings elicited by 7.5 second pulses to +40 mV following injection of oocytes with 6 ng/oocyte KVLQT1 and a variable amount of KCNE1 cRNA, as indicated. Note the presence of KvLQT1 current, and the absence of $I_{Ks}$ in the oocyte injected with 0.01 ng KCNE1. B) Current amplitude following a 7.5 second pulse to +40 mV was normalized to peak current obtained by injection of 1.2 ng KCNE1. Values represent mean±S.E.M. N=8 oocytes/group.

FIGS. 15A–15D. Functional effects of D76N KCNE1 mutation. A) $I_{Ks}$ was elicited by 7.5 second pulses from a holding potential of –80 mV to test potentials of –40 to +40 mV. Deactivating tail currents were elicited by returning membrane potential to –50 mV. B) Isochronal current-voltage relation of $I_{Ks-WT}$ (n=14) and $I_{Ks-D76N}$ (n=14), demonstrating dominant negative suppression of $I_{Ks}$ by D76N (p<0.0001). C) The voltage dependence of $I_{Ks-D76N}$ activation, using a 7.5 second test pulse, is shifted by +16 mV compared to $I_{Ks-WT}$. Smooth curves are best fits of normalized tail currents to a Boltzmann function ($V_{1/2}$= 10.8±0.8 mV, slope factor=12.1±0.3 mV for $I_{Ks-WT}$; for $I_{Ks-D76N}$ $V_{1/2}$=25.7±1.0 mV [p<0.0001, compared to $I_{Ks-WT}$], slope factor=12.0±0.2 mV; n=14). D) $I_{Ks-D76N}$ deactivates faster than $I_{Ks-WT}$. $I_{Ks}$ was activated by a 5 second pulse to +20 mV, and tail currents were measured at the indicated potentials. Tail currents were fit to a single exponential function. Inset shows normalized deactivating tail currents at –50 mV, after a voltage step to +20 mV.

FIGS. 16A–16D. Functional effects of S74L KCNE1 mutation. A) $I_{Ks-WT}$ and $I_{Ks-S74L}$ recorded during 7.5 second depolarizations to –40, –20, 0, +20 and +40 mV. Note the faster rate of deactivating $I_{Ks-S74L}$ tail currents compared to $I_{Ks-WT}$. B) Isochronal current-voltage relation for $I_{Ks-WT}$ and $I_{Ks-S74L}$ (n=15). C) Voltage dependence of $I_{Ks-S74L}$ activation is shifted by +19 mV relative to $I_{Ks-WT}$. Smooth curves are best fits of normalized tail currents to a Boltzmann function ($V_{1/2}$=13.7±0.6 mV, slope factor=16.0±0.3 mV for $I_{Ks-WT}$; for $I_{Ks-S74L}$ $V_{1/2}$=33.6±0.8 mV, slope factor= 13.3±mV [both p<0.0001 relative to $I_{Ks-WT}$]). D) $I_{Ks-S74L}$ deactivates faster than $I_{Ks-WT}$.

Figure 17:
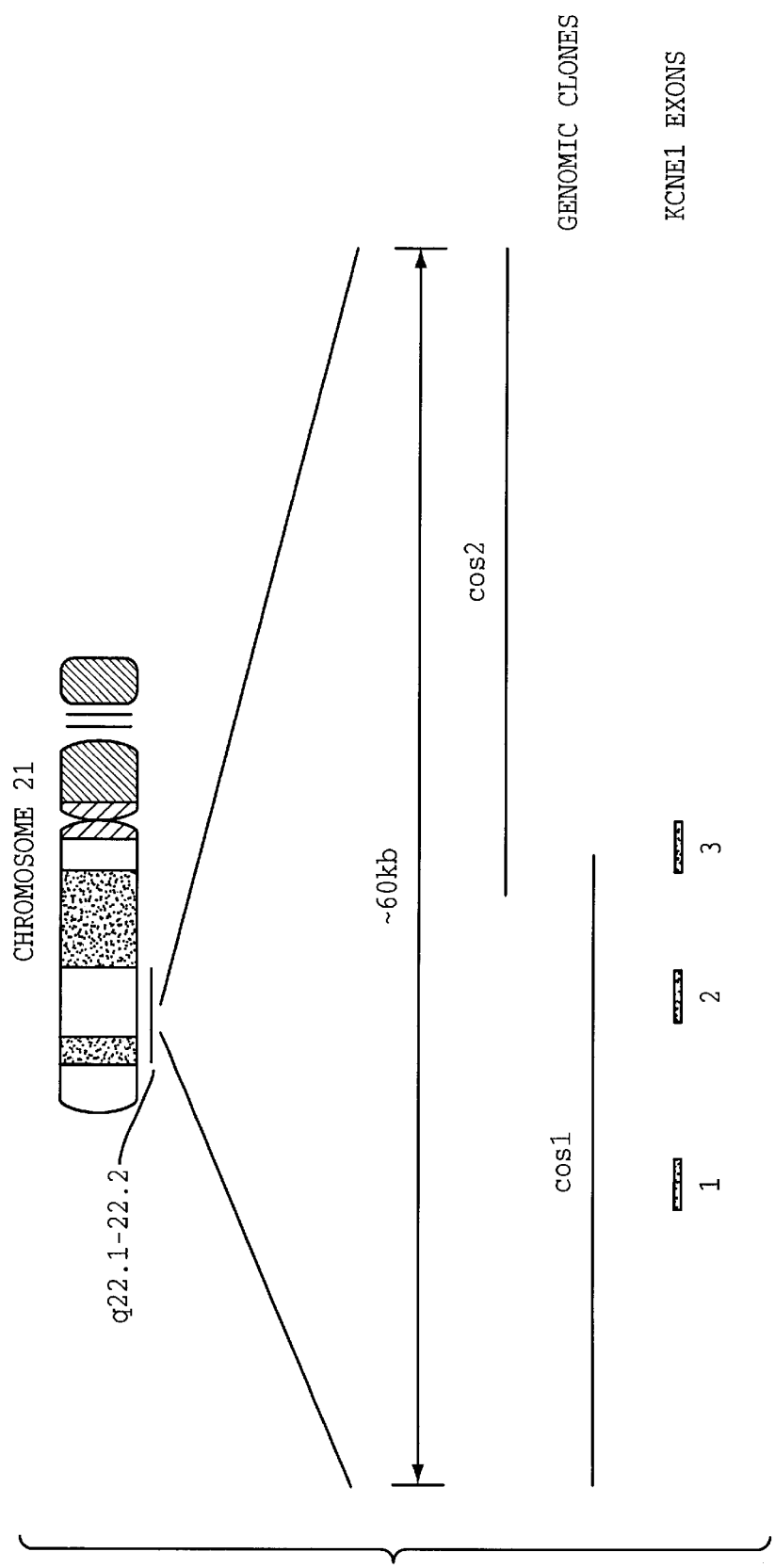

FIG. 17. Physical map and exon organization of KCNE1. The two cosmid clones spanning the entire KCNE1 transcript are shown. Cosmid 1 does not extend to the end of exon 3 and cosmid 2 does not include exons 1 and 2. Sizes of the exons and distances are not drawn to scale.

FIG. 18. Genomic organization of the KCNE1 coding and 5' and 3' untranslated regions. Positions of the introns are indicated with arrowheads. Note that both introns are within the 5'-untranslated region. The asterisk indicates the stop codon. The nucleotide sequence of FIG. 18 is SEQ ID NO:3. The amino acid sequence of FIG. 18 is SEQ ID NO:4.

BRIEF DESCRIPTION OF THE SEQUENCE LISTING

SEQ ID NO:1 is human KVLQT1 cDNA.
SEQ ID NO:2 is human KVLQT1 protein.
SEQ ID NO:3 is human KCNE1 cDNA.
SEQ ID NO:4 is human KCNE1 protein.
SEQ ID NOs:5–6 are hypothetical nucleic acids used to demonstrate calculation of homology.
SEQ ID NOs:7–8 are oligonucleotides used to capture and repair human KVLQT1 cDNA (see Example 4).
SEQ ID NOs:9–40 are the intron/exon boundaries of human KVLQT1 (Table 3).
SEQ ID NOs:41–74 are primers used to amplify KVLQT1 exons (Table 4).
SEQ ID NOs:75–86 are primers used to define KVLQT1 mutations (Table 5).
SEQ ID NOs:87–92 are primer pairs used to amplify genomic KCNE1.
SEQ ID NOs:93–94 are primers used to amplify KCNE1 cDNA.
SEQ ID NOs:95–100 are intron/exon boundaries of KCNE1 (Table 8).
SEQ ID NOs:101–106 are primers to amplify KCNE1 exons (Table 9).
SEQ ID NOs:107–109 are fragments of KVLQT1 shown in FIG. 3.
SEQ ID NOs:110–112 are fragments of DMSHAKE shown in FIG. 3.
SEQ ID NO: 113 is a partial Xenopus KVLQT1 shown in FIG. 10.
SEQ ID NO: 114 is a partial human KVLQT1 shown in FIG. 10.

DETAILED DESCRIPTION OF THE INVENTION

The present invention is directed to the determination of the genomic structure of KVLQT1 and KCNE1 and to molecular variants of these genes which cause or are involved in the pathogenesis of LQT. It is also directed to the determination that KVLQT1 and minK coassemble to form cardiac $I_{Ks}$ potassium channels. More specifically, the present invention relates to mutations in the KVLQT1 gene and also in the KCNE1 gene and their use in the diagnosis of LQT. The present invention is further directed to methods of screening humans for the presence of KVLQT1 and/or KCNE1 gene variants which cause LQT. Since LQT can now be detected earlier (i.e., before symptoms appear) and more definitively, better treatment options will be available in those individuals identified as having LQT. The present invention is also directed to methods for screening for drugs useful in treating or preventing LQT1.

The present invention provides methods of screening the KVLQT1 and/or KCNE1 gene to identify mutations. Such methods may further comprise the step of amplifying a portion of the KVLQT1 or KCNE1 gene, and may further include a step of providing a set of polynucleotides which are primers for amplification of said portion of the KVLQT1 or KCNE1 gene. The method is useful for identifying mutations for use in either diagnosis of LQT or prognosis of LQT.

The present invention further demonstrates that KCNE1 (encoding KCNE1 which is also referred to in the literature as minK) on chromosome 21 is also involved in LQT. The minK protein and KVLQT1 coassemble to form a K⁺ channel. The present invention thus provides methods of screening the KCNE1 gene to identify mutations. Such methods may further comprise the step of amplifying a portion of the KCNE1 gene, and may further include a step of providing a set of polynucleotides which are primers for amplification of said portion of the KCNE1 gene. The method is useful for identifying mutations for use in either diagnosis of LQT or prognosis of LQT.

Finally, the present invention is directed to a method for screening drug candidates to identity drugs useful for treating or preventing LQT. Drug screening is performed by coexpressing mutant KVLQT1 and/or KCNE1 genes in cells, such as oocytes, mammalian cells or transgenic animals, and assaying the effect of a drug candidate on the $I_{Ks}$ channel. The effect is compared to the $I_{Ks}$ channel activity of the wild-type KVLQT1 and KCNE1 genes.

Proof that the KVLQT1 or KCNE1 gene is involved in causing LQT is obtained by finding sequences in DNA extracted from affected kindred members which create abnormal KVLQT1 or KCNE1 gene products or abnormal levels of the gene products. Such LQT susceptibility alleles will co-segregate with the disease in large kindreds. They will also be present at a much higher frequency in non-kindred individuals with LQT than in individuals in the general population. The key is to find mutations which are serious enough to cause obvious disruption to the normal function of the gene product. These mutations can take a number of forms. The most severe forms would be frame shift mutations or large deletions which would cause the gene to code for an abnormal protein or one which would significantly alter protein expression. Less severe disruptive mutations would include small in-frame deletions and non-conservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

According to the diagnostic and prognostic method of the present invention, alteration of the wild-type KVLQT1 or KCNE1 gene is detected. In addition, the method can be performed by detecting the wild-type KVLQT1 or KCNE1 gene and confirming the lack of a cause of LQT as a result of this locus. "Alteration of a wild-type gene" encompasses all forms of mutations including deletions, insertions and point mutations in the coding and noncoding regions. Deletions may be of the entire gene or of only a portion of the gene. Point mutations may result in stop codons, frameshift mutations or amino acid substitutions. Somatic mutations are those which occur only in certain tissues and are not inherited in the germline. Germline mutations can be found in any of a body's tissues and are inherited. Point mutational events may occur in regulatory regions, such as in the promoter of the gene, leading to loss or diminution of expression of the mRNA. Point mutations may also abolish proper RNA processing, leading to loss of expression of the KVLQT1 or KCNE1 gene product, or to a decrease in mRNA stability or translation efficiency.

Useful diagnostic techniques include, but are not limited to fluorescent in situ hybridization (FISH), direct DNA sequencing, PFGE analysis, Southern blot analysis, single stranded conformation analysis (SSCA), RNase protection assay, allele-specific oligonucleotide (ASO), dot blot analysis and PCR-SSCP, as discussed in detail further below. Also useful is the recently developed technique of DNA microchip technology.

The presence of LQT may be ascertained by testing any tissue of a human for mutations of the KVLQT1 gene or the KCNE1 gene. For example, a person who has inherited a germline KVLQT1 or KCNE1 mutation would be prone to develop LQT. This can be determined by testing DNA from any tissue of the person's body. Most simply, blood can be drawn and DNA extracted from the cells of the blood. In addition, prenatal diagnosis can be accomplished by testing fetal cells, placental cells or amniotic cells for mutations of the KVLQT1 or KCNE1 gene. Alteration of a wild-type KVLQT1 or KCNE1 allele, whether, for example, by point mutation or deletion, can be detected by any of the means discussed herein.

There are several methods that can be used to detect DNA sequence variation. Direct DNA sequencing, either manual sequencing or automated fluorescent sequencing can detect sequence variation. Another approach is the single-stranded conformation polymorphism assay (SSCP) (Orita et al., 1989). This method does not detect all sequence changes, especially if the DNA fragment size is greater than 200 bp, but can be optimized to detect most DNA sequence variation. The reduced detection sensitivity is a disadvantage, but the increased throughput possible with SSCP makes it an attractive, viable alternative to direct sequencing for mutation detection on a research basis. The fragments which have shifted mobility on SSCP gels are then sequenced to determine the exact nature of the DNA sequence variation. Other approaches based on the detection of mismatches between the two complementary DNA strands include clamped denaturing gel electrophoresis (CDGE) (Sheffield et al., 1991), heteroduplex analysis (HA) (White et al., 1992) and chemical mismatch cleavage (CMC) (Grompe et al., 1989). None of the methods described above will detect large deletions, duplications or insertions, nor will they detect a regulatory mutation which affects transcription or translation of the protein. Other methods which might detect these classes of mutations such as a protein truncation assay or the asymmetric assay, detect only specific types of mutations and would not detect missense mutations. A review of currently available methods of detecting DNA sequence variation can be found in a recent review by Grompe (1993). Once a mutation is known, an allele specific detection approach such as allele specific oligonucleotide (ASO) hybridization can be utilized to rapidly screen large numbers of other samples for that same mutation. Such a technique can utilize probes which are labeled with gold nanoparticles to yield a visual color result (Elghanian et al., 1997).

A rapid preliminary analysis to detect polymorphisms in DNA sequences can be performed by looking at a series of Southern blots of DNA cut with one or more restriction enzymes, preferably with a large number of restriction enzymes. Each blot contains a series of normal individuals and a series of LQT cases. Southern blots displaying hybridizing fragments (differing in length from control DNA when probed with sequences near or including the KVLQT1 locus) indicate a possible mutation. If restriction enzymes which produce very large restriction fragments are used, then pulsed field gel electrophoresis (PFGE) is employed.

Detection of point mutations may be accomplished by molecular cloning of the KVLQT1 or KCNE1 alleles and sequencing the alleles using techniques well known in the art. Also, the gene or portions of the gene may be amplified, e.g., by PCR or other amplification technique, and the amplified gene or amplified portions of the gene may be sequenced.

There are six well known methods for a more complete, yet still indirect, test for confirming the presence of a susceptibility allele: 1) single stranded conformation analysis (SSCP) (Orita et al., 1989); 2) denaturing gradient gel electrophoresis (DGGE) (Wartell et al., 1990; Sheffield et al., 1989); 3) RNase protection assays (Finkelstein et al., 1990; Kinszler et al., 1991); 4) allele-specific oligonucleotides (ASOs) (Conner et al., 1983); 5) the use of proteins which recognize nucleotide mismatches, such as the E. coli mutS protein (Modrich, 1991); and 6) allele-specific PCR (Ruano and Kidd, 1989). For allele-specific PCR, primers are used which hybridize at their 3' ends to a particular KVLQT1 or KCNE1 mutation. If the particular mutation is not present, an amplification product is not observed. Amplification Refractory Mutation System (ARMS) can also be used, as disclosed in European Patent Application Publication No. 0332435 and in Newton et al., 1989. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Such a method is particularly useful for screening relatives of an affected individual for the presence of the mutation found in that individual. Other techniques for detecting insertions and deletions as known in the art can be used.

In the first three methods (SSCP, DGGE and RNase protection assay), a new electrophoretic band appears. SSCP detects a band which migrates differentially because the sequence change causes a difference in single-strand, intramolecular base pairing. RNase protection involves cleavage of the mutant polynucleotide into two or more smaller fragments. DGGE detects differences in migration rates of mutant sequences compared to wild-type sequences, using a denaturing gradient gel. In an allele-specific oligonucleotide assay, an oligonucleotide is designed which detects a specific sequence, and the assay is performed by detecting the presence or absence of a hybridization signal. In the mutS assay, the protein binds only to sequences that contain a nucleotide mismatch in a heteroduplex between mutant and wild-type sequences.

Mismatches, according to the present invention, are hybridized nucleic acid duplexes in which the two strands are not 100% complementary. Lack of total homology may be due to deletions, insertions, inversions or substitutions. Mismatch detection can be used to detect point mutations in the gene or in its mRNA product. While these techniques are less sensitive than sequencing, they are simpler to perform on a large number of samples. An example of a mismatch cleavage technique is the RNase protection method. In the practice of the present invention, the method involves the use of a labeled riboprobe which is complementary to the human wild-type KVLQT1 or KCNE1 gene coding sequence. The riboprobe and either mRNA or DNA isolated from the person are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full length duplex RNA for the riboprobe and the mRNA or DNA. The riboprobe need not be the full length of the mRNA or gene but can be a segment of either. If the riboprobe comprises only a segment of the mRNA or gene, it will be desirable to use a number of these probes to screen the whole mRNA sequence for mismatches.

In similar fashion, DNA probes can be used to detect mismatches, through enzymatic or chemical cleavage. See, e.g., Cotton el al., 1988; Shenk et al., 1975; Novack et al., 1986. Alternatively, mismatches call be detected by shifts in the electrophoretic mobility of mismatched duplexes relative to matched duplexes. See, e.g.. Cariello, 1988. With either riboprobes or DNA probes, the cellular mRNA or DNA which might contain a mutation can be amplified using PCR (see below) before hybridization. Changes in DNA of the KVLQT1 or KCNE1 gene can also be detected using Southern hybridization, especially if the changes are gross rearrangements, such as deletions and insertions.

DNA sequences of the KVLQT1 or KCNE1 gene which have been amplified by use of PCR may also be screened using allele-specific probes. These probes are nucleic acid oligomers, each of which contains a region of the gene sequence harboring a known mutation. For example, one oligomer may be about 30 nucleotides in length, corresponding to a portion of the gene sequence. By use of a battery of such allele-specific probes, PCR amplification products can be screened to identify the presence of a previously identified mutation in the grene. Hybridization of allele-specific probes with amplified KVLQT1 or KCNE1 sequences can be performed, for example, on a nylon filter. Hybridization to a particular probe under high stringency hybridization conditions indicates the presence of the same mutation in the tissue as in the allele-specific probe.

The newly developed technique of nucleic acid analysis via microchip technology is also applicable to the present invention. In this technique, literally thousands of distinct oligonucleotide probes are built up in an array on a silicon chip. Nucleic acid to be analyzed is fluorescence labeled and hybridized to the probes on the chip. It is also possible to study nucleic acid-protein interactions using these nucleic acid microchips. Using this technique one can determine the presence of mutations or even sequence the nucleic acid being analyzed or one can measure expression levels of a gene of interest. The method is one of parallel processing of many, even thousands, of probes at once and can tremendously increase the rate of analysis. Several papers have been published which use this technique. Some of these are Hacia et al., 1996; Shoemaker et al., 1996; Chee et al., 1996; Lockhart et al., 1996; DeRisi et al., 1996; Lipshutz et al., 1995. This method has already been used to screen people for mutations in the breast cancer gene BRCA1 (Hacia et al., 1996). This new technology has been reviewed in a news article in Chemical and Engineering News (Borman, 1996) and been the subject of an editorial (Editorial, Nature Genetics, 1996). Also see Fodor (1997).

The most definitive test for mutations in a candidate locus is to directly compare genomic KVLQT1 or KCNE1 sequences from patients with those from a control population. Alternatively, one could sequence messenger RNA after amplification, e.g., by PCR, thereby eliminating the necessity of determining the exon structure of the candidate gene.

Mutations from patients falling outside the coding region of KVLQT1 or KCNE1 can be detected by examining the non-coding regions, such as introns and regulatory sequences near or within the genes. An early indication that mutations in noncoding regions are important may come from Northern blot experiments that reveal messenger RNA molecules of abnormal size or abundance in patients as compared to control individuals.

Alteration of KVLQT1 or KCNE1 mRNA expression can be detected by any techniques known in the art. These include Northern blot analysis, PCR amplification and RNase protection. Diminished mRNA expression indicates an alteration of the wild-type gene. Alteration of wild-type genes can also be detected by screening for alteration of wild-type KVLQT1 or KCNE1 protein. For example, monoclonal antibodies immunoreactive with KVLQT1 or KCNE1 can be used to screen a tissue. Lack of cognate antigen would indicate a mutation. Antibodies specific for products of mutant alleles could also be used to detect mutant gene product. Such immunological assays can be done in any convenient formats known in the art. These include Western blots, immunohistochemical assays and ELISA assays. Any means for detecting an altered KVLQT1 or KCNE1 protein can be used to detect alteration of the wild-type KVLQT1 or KCNE1 gene. Functional assays, such as protein binding determinations, can be used. In addition, assays can be used which detect KVLQT1 or KCNE1 biochemical function. Finding a mutant KVLQT1 or KCNE1 gene product indicates alteration of a wild-type KVLQT1 or KCNE1 gene.

A mutant KVLQT1 or KCNE1 gene or gene product can also be detected in other human body samples, such as serum, stool, urine and sputum. The same techniques discussed above for detection of mutant genes or gene products in tissues can be applied to other body samples. By screening such body samples, a simple early diagnosis can be achieved for LQT.

The primer pairs of the present invention are useful for determination of the nucleotide sequence of a particular KVLQT1 or KCNE1 allele using PCR. The pairs of single-stranded DNA primers for KVLQT1 can be annealed to sequences within or surrounding the KVLQT1 gene on chromosome 11 in order to prime amplifting DNA synthesis of the gene itself. The pairs of single-stranded DNA primers for KCNE1 can be annealed to sequences within or surrounding the KCNE1 gene on chromosome 21 in order to prime amplifying DNA synthesis of the gene itself. A complete set of these primers allows synthesis of all of the nucleotides of the gene coding sequences i.e., the exons. The set of primers preferably allows synthesis of both intron and exon sequences. Allele-specific primers can also be used. Such primers anneal only to particular KVLQT1 or KCNE1 mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from KVLQT1 or KCNE1 sequence or sequences adjacent to KVLQT1 or KCNE1, except for the few nucleotides necessary to form a restriction enzyme site. Such enzymes and sites are well known in the art. The primers themselves can be synthesized using techniques which are well known in the art. Generally, the primers can be made using oligonucleotide synthesizing machines which are commercially available. Given the sequence of KVLQT1 and KCNE1, design of particular primers is well within the skill of the art. The present invention adds to this by presenting data on the intron/exon boundaries thereby allowing one to design primers to amplify and sequence all of the exonic regions completely.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the KVLQT1 or KCNE1 gene or mRNA using other techniques.

It has been discovered that individuals with the wild-type KVLQT1 or KCNE1 gene do not have LQT. However mutations which interfere with the function of the KVLQT1 or KCNE1 gene product are involved in the pathogenesis of LQT. Thus, the presence of an altered (or a mutant) KVLQT1 or KCNE1 gene which produces a protein having a loss of function, or altered function, directly causes LQT which increases the risk of cardiac arrhythmias. In order to detect a KVLQT1 or KCNE1 gene mutation, a biological sample is prepared and analyzed for a difference between the sequence of the allele being analyzed and the sequence of the wild-type allele. Mutant KVLQT1 or KCNE1 alleles can be initially identified by any of the techniques described above. The mutant alleles are then sequenced to identify the specific mutation of the particular mutant allele. Alternatively, mutant alleles can be initially identified by identifying mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

It has also been discovered that the KVLQT1 protein coassembles with the minK protein. Thus, mutations in KCNE1 (which encodes minK) which interfere in the function of the KCNE1 gene product are involved in the pathogenesis of LQT. Thus, the presence of an altered (or a mutant) KCNE1 gene which produces a protein having a loss of function, or altered function, directly causes LQT which increases the risk of cardiac arrhythmias. In order to detect a KCNE1 gene mutation, a biological sample is prepared and analyzed for a difference between the sequence of the allele being analyzed and the sequence of the wild-type allele. Mutant KCNE1 alleles can be initially identified by any of the techniques described above. The mutant alleles are then sequenced to identify the specific mutation of the particular mutant (altered) proteins, using conventional techniques. The mutant alleles are then sequenced to identify the specific mutation for each allele. The mutations, especially those which lead to an altered function of the protein, are then used for the diagnostic and prognostic methods of the present invention.

Definitions

The present invention employs the following definitions:

"Amplification of Polynucleotides" utilizes methods such as the polymerase chain reaction (PCR), ligation amplification (or ligase chain reaction, LCR) and amplification methods based on the use of Q-beta replicase. Also useful are strand displacement amplification (SDA), thermophilic SDA, and nucleic acid sequence based amplification (3SR or NASBA). These methods are well known and widely practiced in the art. See, e.g., U.S. Pat. Nos. 4,683,195 and 4,683,202 and Innis et al., 1990 (for PCR); Wu and Wallace, 1989 (for LCR); U.S. Pat. Nos. 5,270,184 and 5,455,166 and Walker et al., 1992 (for SDA); Spargo et al., 1996 (for thermophilic SDA) and U.S. Pat. No. 5,409,818, Fahy et al., 1991 and Compton, 1991 for 3SR and NASBA. Reagents and hardware for conducting PCR are commercially available. Primers useful to amplify sequences from the KVLQT1 or KCNE1 region are preferably complementary to, and hybridize specifically to sequences in the KVLQT1 or KCNE1 region or in regions that flank a target region therein. KVLQT1 or KCNE1 sequences generated by amplification may be sequenced directly. Alternatively, but less desirably, the amplified sequence(s) may be cloned prior to sequence analysis. A method for the direct cloning and sequence analysis of enzymatically amplified genomic segments has been described by Scharf et al., 1986.

"Analyte polynucleotide" and "analyte strand" refer to a single- or double-stranded polynucleotide which is suspected of containing a target sequence, and which may be present in a variety of types of samples, including biological samples.

"Antibodies." The present invention also provides polyclonal and/or monoclonal antibodies and fragments thereof, and immunologic binding equivalents thereof, which are capable of specifically binding to the KVLQT1 or KCNE1 polypeptide and fragments thereof or to polynucleotide sequences from the KVLQT1 or KCNE1 region. The term "antibody" is used both to refer to a homogeneous molecular entity, or a mixture such as a serum product made up of a plurality of different molecular entities. Polypeptides may be prepared synthetically in a peptide synthesizer and coupled to a carrier molecule (e.g., keyhole limpet hemocyanin) and injected over several months into rabbits. Rabbit sera is tested for immunoreactivity to the KVLQT1 or KCNE1 polypeptide or fragment. Monoclonal antibodies may be made by injecting mice with the protein polypeptides, fusion proteins or fragments thereof. Monoclonal antibodies will be screened by ELISA and tested for specific immunoreactivity with KVLQT1 or KCNE1 polypeptide or fragments thereof. See, Harlow and Lane, 1988. These antibodies will be useful in assays as well as pharmaceuticals.

Once a sufficient quantity of desired polypeptide has been obtained, it may be used for various purposes. A typical use is the production of antibodies specific for binding. These antibodies may be either polyclonal or monoclonal, and may be produced by in vitro or in vivo techniques well known in the art. For production of polyclonal antibodies, an appropriate target immune system, typically mouse or rabbit, is selected. Substantially purified antigen is presented to the immune system in a fashion determined by methods appropriate for the animal and by other parameters well known to immunologists. Typical sites for injection are in footpads, intramuscularly, intraperitoneally, or intradermally. Of course, other species may be substituted for mouse or rabbit. Polyclonal antibodies are then purified using techniques known in the art, adjusted for the desired specificity.

An immunological response is usually assayed with an immunoassay. Normally, such immunoassays involve some purification of a source of antigen, for example, that produced by the same cells and in the same fashion as the antigen. A variety of immunoassay methods are well known in the art. See, e.g., Harlow and Lane, 1988, or Goding, 1986.

Monoclonal antibodies with affinities of $10^{-8}$ $M^{-1}$ or preferably $10^{-9}$ to $10^{-10}$ $M^{-1}$ or stronger will typically be made by standard procedures as described, e.g., in Harlow and Lane, 1988 or Goding, 1986. Briefly, appropriate animals will be selected and the desired immunization protocol followed. After the appropriate period of time, the spleens of such animals are excised and individual spleen cells fused, typically, to immortalized myeloma cells under appropriate selection conditions. Thereafter, the cells are clonally separated and the supernatants of each clone tested for their production of an appropriate antibody specific for the desired region of the antigen.

Other suitable techniques involve in vitro exposure of lymphocytes to the antigenic polypeptides, or alternatively, to selection of libraries of antibodies in phage or similar vectors. See Huse et al., 1989. The polypeptides and antibodies of the present invention may be used with or without modification. Frequently, polypeptides and antibodies will be labeled by joining, either covalently or non-covalently, a substance which provides for a detectable signal. A wide variety of labels and conjugation techniques are known and are reported extensively in both the scientific and patent literature. Suitable labels include radionuclides, enzymes, substrates, cofactors, inhibitors, fluorescent agents, chemiluminiescent agents, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced (see U.S. Pat. No. 4,816,567).

"Binding partner" refers to a molecule capable of binding a ligand molecule with high specificity, as for example, an antigen and an antigen-specific antibody or an enzyme and its inhibitor. In general, the specific binding partners must bind with sufficient affinity to immobilize the analyte copy/complementary strand duplex (in the case of polynucleotide hybridization) under the isolation conditions. Specific binding partners are known in the art and include, for example, biotin and avidin or streptavidin, IgG and protein A, the numerous, known receptor-ligand couples, and complementary polynucleotide strands. In the case of complementary polynucleotide binding partners, the partners are normally at least about 15 bases in length, and may be at least 40 bases in length. It is well recognized by those of skill in the art that lengths shorter than 15 (e.g., 8 bases), between 15 and 40, and greater than 40 bases may also be used. The polynucleotides may be composed of DNA, RNA, or synthetic nucleotide analogs. Further binding partners can be identified using, e.g., the two-hybrid yeast screening assay as described herein.

A "biological sample" refers to a sample of tissue or fluid suspected of containing an analyte polynucleotide or polypeptide from an individual including, but not limited to, e.g., plasma, serum, spinal fluid, lymph fluid, the external sections of the skin, respiratory, intestinal, and genitourinary tracts, tears, saliva, blood cells, tumors, organs, tissue and samples of in vitro cell culture constituents.

"Encode". A polynucleotide is said to "encode" a polypeptide if, in its native state or when manipulated by methods well known to those skilled in the art, it can be transcribed and/or translated to produce the mRNA for and/or the polypeptide or a fragment thereof. The anti-sense strand is the complement of such a nucleic acid, and the encoding sequence can be deduced therefrom.

"Isolated" or "substantially pure". An "isolated" or "substantially pure" nucleic acid (e.g., an RNA, DNA or a mixed polymer) is one which is substantially separated from other cellular components which naturally accompany a native human sequence or protein, e.g., ribosomes, polymerases, many other human genome sequences and proteins. The term embraces a nucleic acid sequence or protein which has been removed from its naturally occurring environment, and includes recombinant or cloned DNA isolates and chemically synthesized analogs or analogs biologically synthesized by heterologous systems.

"KVLQT1 or KCNE1 Allele" refers, respectively, to normal alleles of the KVLQT1 or KCNE1 locus as well as alleles of KVLQT1 or KCNE1 carrying variations that cause LQT.

"KVLQT1 or KCNE1 Locus", "KVLQT1 or KCNE1 Gene", "KVLQT1 or KCNE1 Nucleic Acids" or "KVLQT1 or KCNE1 polynucleotide" each refer to polynucleotides, all of which are in the KVLQT1 or KCNE1 region, respectively, that are likely to be expressed in normal tissue, certain alleles of which result in LQT. The KVLQT1 or KCNE1 locus is intended to include coding sequences, intervening sequences and regulatory elements controlling transcription and/or translation. The KVLQT1 or KCNE1 locus is intended to include all allelic variations of the DNA sequence. The terms "KCNE1" and "minK" may be used interchangeably.

These terms, when applied to a nucleic acid, refer to a nucleic acid which encodes a human KVLQT1 or KCNE1 polypeptide, fragment, homolog or variant, including, e.g., protein fusions or deletions. The nucleic acids of the present invention will possess a sequence which is either derived from, or substantially similar to a natural KVLQT1- or KCNE1-encoding gene or one having substantial homology with a natural KVLQT1- or KCNE1-encoding gene or a portion thereof.

The KVLQT1 or KCNE1 gene or nucleic acid includes normal alleles of the KVLQT1 or KCNE1 gene, respectively, including silent alleles having no effect on the amino acid sequence of the KVLQT1 or KCNE1 polypeptide as well as alleles leading to amino acid sequence variants of the KVLQT1 or KCNE1 polypeptide that do not substantially affect its function. These terms also include alleles having one or more mutations which adversely affect the function of the KVLQT1 or KCNE1 polypeptide. A mutation may be a change in the KVLQT1 or KCNE1 nucleic acid sequence which produces a deleterious change in the amino acid sequence of the KVLQT1 or KCNE1 polypeptide, resulting in partial or complete loss of KVLQT1 or KCNE1 function, respectively, or may be a change in the nucleic acid sequence which results in the loss of effective KVLQT1 or KCNE1 expression or the production of aberrant forms of the KVLQT1 or KCNE1 polypeptide.

The KVLQT1 or KCNE1 nucleic acid may be that shown in SEQ ID NO:1 (KVLQT1) or SEQ ID NO:3 (KCNE1) or it may be an allele as described above or a variant or derivative differing from that shown by a chance which is one or more of addition, insertion, deletion and substitution of one or more nucleotides of the sequence shown. Changes to the nucleotide sequence may result in an amino acid change at the protein level, or not, as determined by the genetic code.

Thus, nucleic acid according to the present invention may include a sequence different from the sequence shown in SEQ ID NOs:1 and 3 yet encode a polypeptide with the same amino acid sequence as shown in SEQ ID NOs:2 (KVLQT1) and 4 (KCNE1). That is, nucleic acids of the present invention include sequences which are degenerate as a result of the genetic code. On the other hand, the encoded polypeptide may comprise an amino acid sequence which differs by one or more amino acid residues from the amino acid sequence shown in SEQ ID NOs:2 and 4. Nucleic acid encoding a polypeptide which is an amino acid sequence variant, derivative or allele of the amino acid sequence shown in SEQ ID NOs:2 and 4 is also provided by the present invention.

The KVLQT1 or KCNE1 gene, respectively, also refers to (a) any DNA sequence that (i) hybridizes to the complement of the DNA sequences that encode the amino acid sequence set forth in SEQ ID NO:2 or SEQ ID NO:4 under highly stringent conditions (Ausubel et al., 1992) and (ii) encodes a gene product functionally equivalent to KVLQT1 or KCNE1, or (b) any DNA sequence that (i) hybridizes to the complement of the DNA sequences that encode the amino acid sequence set forth in SEQ ID NO:2 or SEQ ID NO:4 under less stringent conditions, such as moderately stringent conditions (Ausubel et al., 1992) and (ii) encodes a gene product functionally equivalent to KVLQT1 or KCNE1. The invention also includes nucleic acid molecules that are the complements of the sequences described herein.

The polynucleotide compositions of this invention include RNA, cDNA, genomic DNA, synthetic forms, and mixed polymers, both sense and antisense strands, and may be chemically or biochemically modified or may contain non-natural or derivatized nucleotide bases, as will be readily appreciated by those skilled in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates. etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule.

The present invention provides recombinant nucleic acids comprising all or part of the KVLQT1 or KCNE1 region. The recombinant construct may be capable of replicating autonomously in a host cell. Alternatively, the recombinant construct may become integrated into the chromosomal DNA of the host cell. Such a recombinant polynucleotide comprises a polynucleotide of genomic, cDNA, semi-synthetic, or synthetic origin which, by virtue of its origin or manipulation, 1) is not associated with all or a portion of a polynucleotide with which it is associated in nature; 2) is linked to a polynucleotide other than that to which it is linked in nature; or 3) does not occur in nature. Where nucleic acid according to the invention includes RNA, reference to the sequence shown should be construed as reference to the RNA equivalent, with U substituted for T.

Therefore, recombinant nucleic acids comprising sequences otherwise not naturally occurring are provided by this invention. Although the wild-type sequence may be employed, it still often be altered, e.g., by deletion, substitution or insertion. cDNA or genomic libraries of various types may be screened as natural sources of the nucleic acids of the present invention, or such nucleic acids may be provided by amplification of sequences resident in genomic DNA or other natural sources, e.g., by PCR. The choice of cDNA libraries normally corresponds to a tissue source which is abundant in mRNA for the desired proteins. Phage libraries are normally preferred, but other types of libraries may be used. Clones of a library are spread onto plates, transferred to a substrate for screening, denatured and probed for the presence of desired sequences.

The DNA sequences used in this invention will usually comprise at least about five codons (15 nucleotides), more usually at least about 7–15 codons, and most preferably, at least about 35 codons. One or more introns may also be present. This number of nucleotides is usually about the minimal length required for a successful probe that would hybridize specifically with a KVLQT1- or KCNE1-encoding sequence. In this context, oligomers of as low as 8 nucleotides, more generally 8–17 nucleotides, can be used for probes, especially in connection with chip technology.

Techniques for nucleic acid manipulation are described generally, for example, in Sambrook et al., 1989 or Ausubel et al., 1992. Reagents useful in applying such techniques, such as restriction enzymes and the like, are widely known in the art and commercially available from such vendors as New England BioLabs, Boehringer Mannheim, Amersham, Promeg, U.S. Biochemicals, New England Nuclear, and a number of other sources. The recombinant nucleic acid sequences used to produce fusion proteins of the present invention may be derived from natural or synthetic sequences. Many natural gene sequences are obtainable from various cDNA or from genomic libraries using appropriate probes. See, GenBank, National Institutes of Health.

As used herein, a "portion" of the KVLQT1 or KCNE1 locus or region or allele is defined as having a minimal size of at least about eight nucleotides, or preferably about 15 nucleotides, or more preferably at least about 25 nucleotides, and may have a minimal size of at least about 40 nucleotides. This definition includes all sizes in the range of 8–40 nucleotides as well as greater than 40 nucleotides. Thus, this definition includes nucleic acids of 8, 12, 15, 20, 25, 40, 60, 80, 100, 200, 300, 400, 500 nucleotides, or nucleic acids having any number of nucleotides within these ranges of values (e.g., 9, 10, 11, 16, 23, 30, 38, 50, 72, 121, etc., nucleotides), or nucleic acids having more than 500 nucleotides. The present invention includes all novel nucleic acids having at least 8 nucleotides derived from SEQ ID NO:1 or SEQ ID NO:3, its complement or functionally equivalent nucleic acid sequences. The present invention does not include nucleic acids which exist in the prior art. That is, the present invention includes all nucleic acids having at least 8 nucleotides derived from SEQ ID NO:1 or SEQ ID NO:3 with the proviso that it does not include nucleic acids existing in the prior art.

"KVLQT1 or KCNE1 protein" or "KVLQT1 or KCNE1 polypeptide" refers to a protein or polypeptide encoded by the KVLQT1 or KCNE1 locus, variants or fragments thereof. The terms "KCNE1" and "minK" are used interchangeably. The term "polypeptide" refers to a polymer of amino acids and its equivalent and does not refer to a specific length of the product; thus, peptides, oligopeptides and proteins are included within the definition of a polypeptide. This term also does not refer to, or exclude modifications of the polypeptide, for example, glycosylations, acetylations, phosphorylations, and the like. Included within the definition are, for example, polypeptides containing one or more analogs of an amino acid (including, for example, unnatural amino acids, etc.), polypeptides with substituted linkages as well as other modifications known in the art, both naturally and non-naturally occurring. Ordinarily, such polypeptides will be at least about 50% homologous to the native KVLQT1 or KCNE1 sequence, preferably in excess of about 90%, and more preferably at least about 95% homologous. Also included are proteins encoded by DNA which hybridize under high or low stringency conditions, to KVLQT1- or KCNE1-encoding nucleic acids and closely related polypeptides or proteins retrieved by antisera to the KVLQT1 or KCNE1 protein(s).

The KVLQT1 or KCNE1 polypeptide may be that shown in SEQ ID NO:2 or SEQ ID NO:4 which may be in isolated and/or purified form, free or substantially free of material with which it is naturally associated. The polypeptide may, if produced by expression in a prokaryotic cell or produced synthetically, lack native post-translational processing, such as glycosylation. Alternatively, the present invention is also directed to polypeptides which are sequence variants, alleles or derivatives of the KVLQT1 or KCNE1 polypeptide. Such polypeptides may have an amino acid sequence which differs from that set forth in SEQ ID NO:2 or SEQ ID NO:4 by one or more of addition, substitution, deletion or insertion of one or more amino acids. Preferred such polypeptides have KVLQT1 or KCNE1 function.

Substitutional variants typically contain the exchange of one amino acid for another at one or more sites with the protein, and may be designed to modulate one or more properties of the polypeptide, such as stability against proteolytic cleavage, without the loss of other functions or properties. Amino acid substitutions may be made on the basis of similarity in polarity, charge, solubility, hydrophobicity, hydrophilicity, and/or the amphipathic nature of the residues involved. Preferred substitutions are ones which are conservative, that is, one amino acid is replaced with one of similar shape and charge. Conservative substitutions are well known in the art and typically include substitutions within the following groups: glycine, alanine; valine, isoleucine, leucine; aspartic acid, glutamic acid; asparagine, glutamine; serine, threonine; lysine, arginine; and tyrosine, phenylalanine.

Certain amino acids may be substituted for other amino acids in a protein structure without appreciable loss of interactive binding capacity with structures such as, for example, antigen-binding regions of antibodies or binding sites on substrate molecules or binding sites on proteins interacting with the KVLQT1 or KCNE1 polypeptide. Since it is the interactive capacity and nature of a protein which defines that protein's biological functional activity, certain amino acid substitutions can be made in a protein sequence, and its underlying DNA coding sequence, and nevertheless obtain a protein with like properties. In making such changes, the hydropathic index of amino acids may be considered. The importance of the hydrophobic amino acid index in conferring interactive biological function on a protein is generally understood in the art (Kyte and Doolittle, 1982). Alternatively, the substitution of like amino acids can be made effectively on the basis of hydrophilicity. The importance of hydrophilicity in conferring interactive biological function of a protein is generally understood in the art (U.S. Pat. No. 4,554,101). The use of the hydrophobic index or hydrophilicity in designing polypeptides is farther discussed in U.S. Pat. No. 5,691,198.

The length of polypeptide sequences compared for homology will generally be at least about 16 amino acids, usually at least about 20 residues, more usually at least about 24 residues, typically at least about 28 residues, and preferably more than about 35 residues.

"Operably linked" refers to a juxtaposition wherein the components so described are in a relationship permitting them to function in their intended manner. For instance, a promoter is operably linked to a coding sequence if the promoter affects its transcription or expression.

The term peptide mimetic or mimetic is intended to refer to a substance which has the essential biological activity of the KVLQT1 or KCNE1 polypeptide. A peptide mimetic may be a peptide-containing molecule that mimics elements of protein secondary structure (Johnson et al., 1993). The underlying rationale behind the use of peptide mimetics is that the peptide backbone of proteins exists chiefly to orient amino acid side chains in such a way as to facilitate molecular interactions, such as those of antibody and antigen, enzyme and substrate or scaffolding proteins. A peptide mimetic is designed to permit molecular interactions similar to the natural molecule. A mimetic may not be a peptide at all, but it will retain the essential biological activity of natural KVLQT1 or KCNE1 polypeptide.

"Probes". Polynucleotide polymorphisms associated with KVLQT1 or KCNE1 alleles which predispose to LQT are detected by hybridization with a polynucleotide probe which forms a stable hybrid with that of the target sequence, under stringent to moderately strigent hybridization and wash conditions. If it is expected that the probes will be perfectly complementary to the target sequence, high stringency conditions will be used. Hybridization stringency may be lessened if some mismatching is expected, for example, if variants are expected with the result that the probe will not be completely complementary. Conditions are chosen which rule out nonspecific/adventitious bindings, that is, which minimize noise. (It should be noted that throughout this disclosure, if it is simply stated that "stringent" conditions are used that is meant to be read as "high stringency" conditions are used.) Since such indications identify neutral DNA polymorphisms as well as mutations, these indications need further analysis to demonstrate detection of a KVLQT1 or KCNE1 susceptibility allele.

Probes for KVLQT1 or KCNE1 alleles may be derived from the sequences of the KVLQT1 or KCNE1 region, its cDNA, functionally equivalent sequences, or the complements thereof. The probes may be of any suitable length, which span all or a portion of the KVLQT1 or KCNE1 region, and which allow specific hybridization to the region. If the target sequence contains a sequence identical to that of the probe, the probes may be short, e.g., in the range of about 8–30 base pairs, since the hybrid will be relatively stable under even stringent conditions. If some degree of mismatch is expected with the probe, i.e., if it is suspected that the probe will hybridize to a variant region, a longer probe man be employed which hybridizes to the target sequence with the requisite specificity.

The probes will include an isolated polynucleotide attached to a label or reporter molecule and may be used to isolate other polynucleotide sequences, having sequence similarity by standard methods. For techniques for preparing and labeling probes see, e.g., Sambrook et al., 1989 or Ausubel et al., 1992. Other similar polynucleotides may be selected by using homologous polynucleotides. Alternatively, polynucleotides encoding these or similar polypeptides may be synthesized or selected by use of the redundancy in the genetic code. Various codon substitutions may be introduced, e.g., by silent chances (thereby producing various restriction sites) or to optimize expression for a particular system. Mutations may be introduced to modify the properties of the polypeptide, perhaps to change the polypeptide degradation or turnover rate.

Probes comprising synthetic oligonucleotides or other polynucleotides of the present invention may be derived from naturally occurring or recombinant single- or double-stranded polynucleotides, or be chemically synthesized. Probes man also be labeled by nick translation, Klenow fill-in reaction, or other methods known in the art.

Portions of the polynucleotide sequence having at least about eight nucleotides, usually at least about 15 nucleotides, and fewer than about 9 kb, usually fewer than about 1.0 kb, from a polynucleotide sequence encoding KVLQT1 or KCNE1 are preferred as probes. This definition therefore includes probes of sizes 8 nucleotides through 9000 nucleotides. Thus, this definition includes probes of 8, 12, 15, 20, 25, 40, 60, 80, 100, 200, 300, 400 or 500 nucleotides or probes having any number of nucleotides within these ranges of values (e.g., 9, 10, 11, 16, 23, 30, 38, 50, 72, 121, etc., nucleotides), or probes having more than 500 nucleotides. The probes may also be used to determine whether mRNA encoding KVLQT1 or KCNE1 is present in a cell or tissue. The present invention includes all novel probes having at least 8 nucleotides derived from SEQ ID NO:1 or SEQ ID NO:3, its complement or functionally equivalent nucleic acid sequences. The present invention does not include probes which exist in the prior art. That is, the present invention includes all probes having at least 8 nucleotides derived from SEQ ID NO:1 or SEQ ID NO:3 with the proviso that they do not include probes existing in the prior art.

Similar considerations and nucleotide lengths are also applicable to primers which may be used for the amplification of all or part of the KVLQT1 or KCNE1 gene. Thus, a definition for primers includes primers of 8, 12, 15, 20, 25, 40, 60, 80, 100, 200, 300, 400, 500 nucleotides, or primers having any number of nucleotides within these ranges of values (e.g., 9, 10, 11, 16, 23, 30, 38, 50, 72, 121, etc. nucleotides), or primers having more than 500 nucleotides, or any number of nucleotides between 500 and 9000. The primers may also be used to determine whether mRNA encoding KVLQT1 or KCNE1 is present in a cell or tissue. The present invention includes all novel primers having at least 8 nucleotides derived from the KVLQT1 or KCNE1 locus for amplifying the KVLQT1 or KCNE1 gene, its complement or functionally equivalent nucleic acid sequences. The present invention does not include primers which exist in the prior art. That is, the present invention includes all primers having at least 8 nucleotides with the proviso that it does not include primers existing in the prior art.

"Protein modifications or fragments" are provided by the present invention for KVLQT1 or KCNE1 polypeptides or fragments thereof which are substantially homologous to primary structural sequence but which include, e.g., in vivo or in nitro chemical and biochemical modifications or which incorporate unusual amino acids. Such modifications include, for example, acetylation, carboxylation, phosphorylation, glycosylation, ubiquitination, labeling, e.g., with radionuclides, and various enzymatic modifications, as will be readily appreciated by those well skilled in the art. A variety of methods for labeling polypeptides and of substituents or labels useful for such purposes are Xwell known in the art, and include radioactive isotopes such as $^{32}P$, ligands which bind to labeled antiligands (e.g., antibodies), fluorophores, chemiluminiescent agents enzymes, and antiligands which can serve as specific binding pair members for a labeled ligand. The choice of label depends on the sensitivity required, ease of conjugation with the primer, stability requirements, and available instrumentation. Methods of labeling polypeptides are we known in the art. See Sambrook et al., 1989 or Ausubel et al., 1992.

Besides substantially full-length polypeptides, the present invention provides for biologically active fragments of the polypeptides. Significant biological activities include ligand-binding, immunological activity and other biological activities characteristic of KVLQT1 or KCNE1 polypeptides. Immunological activities include both immunogenic function in a target immune system, as well as sharing of immunological epitopes for binding, serving as either a competitor or substitute antigen for an epitope of the KVLQT1 or KCNE1 protein. As used herein, "epitope" refers to an antigenic determinant of a polypeptide. An epitope could comprise three amino acids in a spatial conformation which is unique to the epitope. Generally, an epitope consists of at least five such amino acids, and more usually consists of at least 8–10 such amino acids. Methods of determining the spatial conformation of such amino acids are known in the art.

For immunological purposes, tandem-repeat polypeptide segments may be used as immunogens, thereby producing highly antigenic proteins. Alternatively, such polypeptides will serve as highly efficient competitors for specific binding. Production of antibodies specific for KVLQT1 or KCNE1 polypeptides or fragments thereof is described below.

The present invention also provides for fusion polypeptides, comprising KVLQT1 or KCNE1 polypeptides and fragments. Homologous polypeptides may be fusions between two or more KVLQT1 or KCNE1 polypeptide sequences or between the sequences of KVLQT1 or KCNE1 and a related protein. Likewise, heterologous fusions may be constructed which would exhibit a combination of properties or activities of the derivative proteins. For example, ligand-binding or other domains may be "swapped" between different new fusion polypeptides or fragments. Such homologous or heterologous fusion polypeptides may display, for example, altered strength or specificity of binding. Fusion partners include immunoglobulins, bacterial β-galactosidase, trpE, protein A, β-lactamase, alpha amylase, alcohol dehydrogenase and yeast alpha mating factor. See Godowski et al., 1988.

Fusion proteins will typically be made by either recombinant nucleic acid methods, as described below, or may be chemically synthesized. Techniques for the synthesis of polypeptides are described, for example, in Merrifield (1963).

"Protein purification" refers to various methods for the isolation of the KVLQT1 or KCNE1 polypeptides from other biological material, such as from cells transformed with recombinant nucleic acids encoding KVLQT1 or KCNE1, and are well known in the art. For example, such polypeptides may be purified by immunoaffinity chromatography employing, e.g., the antibodies provided by the present invention. Various methods of protein purification are well known in the art, and include those described in Deutscher, 1990 and Scopes, 1982.

The terms "isolated", "substantially pure", and "substantially homogeneous" are used interchangeably to describe a protein or polypeptide which has been separated from components which accompany it in its natural state. A monomeric protein is substantially pure when at least about 60 to 75% of a sample exhibits a single polypeptide sequence. A substantially pure protein will typically comprise about 60 to 90% W/W of a protein sample, more usually about 95%, and preferably will be over about 99% pure. Protein purity or homogeneity may be indicated by a number of means well known in the art, such as polyacrylamide gel electrophoresis of a protein sample, followed by visualizing a single polypeptide band upon staining the gel. For certain purposes, higher resolution may be provided by using HPLC or other means well known in the art which are utilized for purification.

A KVLQT1 or KCNE1 protein is substantially free of naturally associated components when it is separated from the native contaminants which accompany it in its natural state. Thus, a polypeptide which is chemically synthesized or synthesized in a cellular system different from the cell from which it naturally originates will be substantially free from its naturally associated components. A protein may also be rendered substantially free of naturally associated components by isolation, using protein purification techniques well known in the art.

A polypeptide produced as an expression product of an isolated and manipulated genetic sequence is an "isolated polypeptide", as used herein, even if expressed in a homologous cell type. Synthetically made forms or molecules expressed by heterologous cells are inherently isolated molecules.

"Recombinant nucleic acid" is a nucleic acid which is not naturally occurring, or which is made by the artificial combination of two otherwise separated segments of sequence. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions.

"Regulators sequences" refers to those sequences normally within 100 kb of the coding region of a locus, but they may also be more distant from the coding region, which affect the expression of the gene (including transcription of the gene, and translation, splicing, stability or the like of the messenger RNA).

"Substantial homology or similarity". A nucleic acid or fragment thereof is "substantially homologous" ("or substantially similar") to another if, when optimally aligned (with appropriate nucleotide insertions or deletions) with the other nucleic acid (or its complementary strand), there is nucleotide sequence identity in at least about 60% of the nucleotide bases, usually at least about 70%, more usually at least about 80%, preferably at least about 90%, and more preferably at least about 95–98% of the nucleotide bases.

To determine homology between two different nucleic acids, the percent homology is to be determined using the BLASTN program "BLAST 2 sequences". This program is available for public use from the National Center for Biotechnology Information (NCBI) over the Internet (http://www.ncbi.nlm.nih.gov/gorf/bl2.html) (Altschul et al., 1997). The parameters to be used are whatever combination of the following yields the highest calculated percent homology (as calculated below) with the default parameters shown in parentheses:

Program—blastn
Matrix—0 BLOSUM62
Reward for a match—0 or 1 (1)
Penalty for a mismatch—0, −1, −2 or −3 (−2)
Open gap penalty—0, 1, 2, 3, 4 or 5 (5)
Extension gap penalty—0 or 1 (1)
Gap x_dropoff—0 or 50 (50)
Expect—10

Along with a variety of other results, this program shows a percent identity across the complete strands or across regions of the two nucleic acids being matched. The program shows as part of the results an alignment and identity of the two strands being compared. If the strands are of equal length then the identity will be calculated across the complete length of the nucleic acids. If the strands are of unequal lengths, then the length of the shorter nucleic acid is to be used. If the nucleic acids are quite similar across a portion of their sequences but different across the rest of their sequences, the blastn program "BLAST 2 Sequences" will show an identity across only the similar portions, and these portions are reported individually. For purposes of determining homology herein, the percent homology refers to the shorter of the two sequences being compared. If any one region is shown in different alignments with differing percent identities, the alignments which yield the greatest homology are to be used. The averaging is to be performed as in this example of SEQ ID NOs:5 and 6.

5'-ACCGTAGCTACGTACGTATATAGAAAGGGC GCGATCGTCGTCGCGTATGACGACTTAGCATGC-3' (SEQ ID NO:5)

5'-ACCGGTAGCTACGTACGTTATTTAGAAAGGGGT GTGTGTGTGTGTGTAAACCGGGGTTTTCGGGAT CGTCCGTCGCGTATGACGACTTAGCCATGCACG GTATATCGTATTAGGACTAGCGATTGACTAG-3' (SEQ ID NO:6)

The program "BLAST 2 Sequences" shows differing alignments of these two nucleic acids depending upon the parameters which are selected. As examples, four sets of parameters were selected for comparing SEQ ID NOs:5 and 6 (gap x_dropoff was 50 for all cases), with the results shown in Table 1. It is to be noted that none of the sets of parameters selected as shown in Table 1 is necessarily the best set of parameters for comparing these sequences. The percent homology is calculated by multiplying for each region showing identity the fraction of bases of the shorter strand within a region times the percent identity for that region and adding all of these together. For example, using the first set of parameters shown in Table 1, SEQ ID NO:5 is the short sequence (63 bases), and two regions of identity are shown, the first encompassing bases 4–29 (26 bases) of SEQ ID NO:5 with 92% identity to SEQ ID NO:6 and the second encompassing bases 39–59 (21 bases) of SEQ ID NO:5 with 100% identity to SEQ ID NO:6. Bases 1–3, 30–38 and 60–63 (16 bases) are not shown as having any identity with SEQ ID NO:6. Percent homology is calculated as: (26/63)(92)+(21/63)(100)+(16/63)(0)=71.3% homology. The percents of homology calculated using each of the four sets of parameters shown are listed in Table 1. Several other combinations of parameters are possible, but they are not listed for the sake of brevity. It is seen that each set of parameters resulted in a different calculated percent homology. Because the result yielding the highest percent homology is to he used, based solely on these four sets of parameters one would state that SEQ ID NOs:5 and 6 have 87.1% homology. Again it is to be noted that use of other parameters may show an even higher homology for SEQ ID NOs:5 and 6, but for brevity not all the possible results are shown.

Alternatively, substantial homology or (similarity) exists when a nucleic acid or fragment thereof will hybridize to another nucleic acid (or a complementary strand thereof) under selective hybridization conditions, to a strand, or to its complement. Selectivity of hybridization exists

TABLE 1

| | Parameter Values | | | | | |
|---|---|---|---|---|---|---|
| Match | Mis-match | Open Gap | Extension Gap | Regions of identity (%) | | Hom-ology |
| 1 | −2 | 5 | 1 | 4–29 of 5 and 5–31 of 6 (92%) | 39–59 of 5 and 71–91 of 6 (100%) | 71.3 |
| 1 | −2 | 2 | 1 | 4–29 of 5 and 5–31 of 6 (92%) | 33–63 of 5 and 64–96 of 6 (93%) | 83.7 |
| 1 | −1 | 5 | 1 | — | 30–59 of 5 and 61–91 of 6 (93%) | 44.3 |
| 1 | −1 | 2 | 1 | 4–29 of 5 and 5–31 of 6 (92%) | 30–63 of 5 and 61–96 of 6 (91%) | 87.1 | when hybridization which is substantially more selective than total lack of specificity occurs. Typically, selective hybridization will occur when there is at least about 55% homology over a stretch of at least about 14 nucleotides, preferably at least about 65%, more preferably at least about 75%, and most preferably at least about 90%. See, Kanehisa, 1984. The length of homology comparison, as described, may be over longer stretches, and in certain embodiments will often be over a stretch of at least about nine nucleotides, usually at least about 20 nucleotides, more usually at least about 24 nucleotides, typically at least about 28 nucleotides, more typically at least about 32 nucleotides, and preferably at least about 36 or more nucleotides.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1000 mM, typically less than 500 mM, and preferably less than 200 mM. However, the combination of parameters is much more important than the measure of any single parameters. The stringency conditions are dependent on the length of the nucleic acid and the base composition of the nucleic acid and can be determined by techniques well known in the art. See, e.g., Wetmur and Davidson, 1968.

Probe sequences may also hybridize specifically to duplex DNA under certain conditions to form triplex or other higher order DNA complexes. The preparation of such probes and suitable hybridization conditions are well known in the art.

The terms "substantial homology" or "substantial identity", when referring to polypeptides, indicate that the polypeptide or protein in question exhibits at least about 30% identity with an entire naturally-occurring protein or a portion thereof, usually at least about 70% identity, more usually at least about 80% identity, preferably at least about 90% identity, and more preferably at least about 95% identity.

Homology, for polypeptides, is typically measured using sequence analysis software. See, e.g., the Sequence Analysis Software Package of the Genetics Computer Group, University of Wisconsin Biotechnology Center, 910 University Avenue, Madison, Wis. 53705. Protein analysis software matches similar sequences using measures of homology assigned to various substitutions, deletions and other modifications. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine.

"Substantially similar function" refers to the function of a modified nucleic acid or a modified protein, with reference to the wild-type KVLQT1 or KCNE1 nucleic acid or wild-type KVLQT1 or KCNE1 polypeptide. The modified polypeptide will be substantially homologous to the wild-type KVLQT1 or KCNE1 polypeptide and will have substantially the same function. The modified polypeptide may have an altered amino acid sequence and/or may contain modified amino acids. In addition to the similarity of function, the modified polypeptide may have other useful properties, such as a longer half-life. The similarity of function (activity) of the modified polypeptide may be substantially the same as the activity of the wild-type KVLQT1 or KCNE1 polypeptide. Alternatively, the similarity of function (activity) of the modified polypeptide may be higher than the activity of the wild-type KVLQT1 or KCNE1 polypeptide. The modified polypeptide is synthesized using conventional techniques, or is encoded by a modified nucleic acid and produced using conventional techniques. The modified nucleic acid is prepared by conventional techniques. A nucleic acid with a function substantially similar to the wild-type KVLQT1 or KCNE1 gene function produces the modified protein described above.

A polypeptide "fragment", "portion" or "segment" is a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids.

The polypeptides of the present invention, if soluble, may be coupled to a solid-phase support, e.g., nitrocellulose, nylon, column packing materials (e.g., Sepharose beads), magnetic beads, glass wool, plastic, metal, polymer gels, cells, or other substrates. Such supports may take the form, for example, of beads, wells, dipsticks, or membranes.

"Target region" refers to a region of the nucleic acid which is amplified and/or detected. The term "target sequence" refers to a sequence with which a probe or primer will form a stable hybrid under desired conditions.

The practice of the present invention employs, unless otherwise indicated, conventional techniques of chemistry, molecular biology, microbiology, recombinant DNA, genetics, and immunology. See, e.g., Maniatis et al., 1982; Sambrook et al., 1989; Ausubel et al., 1992; Glover, 1985: Anand, 1992; Guthrie and Fink, 1991. A general discussion of techniques and materials for human gene mapping, including mapping of human chromosome 1, is provided, e.g., in White and Lalouel, 1988.

Preparation of Recombinant or Chemically Synthesized Nucleic Acids; Vectors, Transformation, Host Cells Large amounts of the polynucleotides of the present invention may be produced by replication in a suitable host cell. Natural or synthetic polynucleotide fragments coding for a desired fragment still be incorporated into recombinant polynucleotide constructs, usually DNA constructs, capable of introduction into and replication in a prokaryotic or eukaryotic cell. Usually the polynucleotide constricts will be suitable for replication in a unicellular host, such as yeast or bacteria, but may also be intended for introduction to (with and without integration within the genome) cultured mammalian or plant or other eukaryotic cell lines. The purification of nucleic acids produced by the methods of the present invention are described, e.g., in Sambrook et al., 1989 or Ausubel et al., 1992.

The polynucleotides of the present invention may also be produced by chemical synthesis, e.g., by the phosphoramidite method described by Beaucage and Caruthers (1981) or the triester method according to Matteucci and Caruthers (1981) and may be performed on commercial, automated oligonucleotide synthesizers. A double-stranded fragment may be obtained from the single-stranded product of chemical synthesis either by synthesizing the complementary strand and annealing the strand together under appropriate conditions or by adding the complementary strand using DNA polymerase with an appropriate primer sequence.

Polynucleotide constructs prepared for introduction into a prokaryotic or elukaryotic host may comprise a replication system recognized by the host, including the intended polynucleotide fragment encoding the desired polypeptide, and will preferably also include transcription and translational initiation regulatory sequences operably linked to the polypeptide encoding segment. Expression vectors may include, for example, an origin of replication or autonomously replicating sequence (ARS) and expression control sequences, a promoter, an enhancer and necessary processing information sites, such as ribosome-binding sites, RNA splice sites, polyadenylation sites, transcriptional terminator sequences, and mRNA stabilizing sequences. Such vectors may be prepared by means of standard recombinant techniques well known in the art and discussed, for example. in Sambrook et al., 1989 or Ausubel et al., 1992.

An appropriate promoter and other necessary vector sequences will be selected so as to be functional in the host. and may include. When appropriate, those naturally associated with the KVLQT1 or KCNE1 gene. Examples of workable combinations of cell lines and expression vectors are described in Sambrook et al., 1989 or Ausubel et al., 1992; see also, e.g., Metzger et al., 1988. Many useful vectors are known in the art and may be obtained from such vendors as Stratagene, New England Biolabs, Promega Biotech, and others. Promoters such as the trp, lac and phage promoters, tRNA promoters and glycolytic enzyme promoters may be used in prokaryotic hosts. Useful yeast promoters include promoter regions for metallothionein, 3-phosphoglycerate kinase or other glycolytic enzymes such as enolase or glyceraldehyde-3-phosphate dehydrogenase, enzymes responsible for maltose and galactose utilization, and others. Vectors and promoters suitable for use in yeast expression are further described in Hitzeman et al., EP 73,675A. Appropriate non-native mammalian promoters might include the early and late promoters from SV40 (Fiers et al., 1978) or promoters derived from murine Molony leukemia virus, mouse tumor virus, avian sarcoma viruses, adenovirus II, bovine papilloma virus or polyoma. Insect promoters may be derived from baculovirus. In addition, the construct may be joined to an amplifiable gene (e.g., DHFR) so that multiple copies of the gene may be made. For appropriate enhancer and other expression control sequences, see also *Enhancers and Eukaryotic Gene Expression,* Cold Spring Harbor Press, Cold Spring Harbor, N.Y. (1983). See also, e.g.. U.S. Pat. Nos. 5,691,198; 5,735, 500; 5,747,469 and 5,436,146.

While such expression vectors may replicate autonomously, they may also replicate by being inserted into the genome of the host cell, by methods well known in the art.

Expression and cloning vectors will likely contain a selectable marker, a gene encoding a protein necessary for survival or growth of a host cell transformed with the vector. The presence of this gene ensures growth of only those host cells which express the inserts. Typical selection genes encode proteins that a) confer resistance to antibiotics or other toxic substances, e.g. ampicillin, neomycin, methotrexate, etc., b) complement auxotrophic deficiencies, or c) supply critical nutrients not available from complex media, e.g., the gene encoding D-alanine racemase for Bacilli. The choice of the proper selectable marker will depend on the host cell, and appropriate markers for different hosts are well known in the art.

The vectors containing the nucleic acids of interest can be transcribed it vitro, and the resulting RNA introduced into the host cell by well-known methods, e.g., by injection (see, Kubo et al., 1988), or the vectors can be introduced directly into host cells by methods well known in the art, which vary depending on the type of cellular host, including electroporation; transfection employing calcium chloride, rubidium chloride calcium phosphate, DEAE-dextran, or other substances; microprojectile bombardment; lipofection; infection (where the vector is an infectious agent, such as a retroviral genome); and other methods. See generally, Sambrook et al., 1989 and Ausubel et al., 1992. The introduction of the polynucleotides into the host cell by any method known in the art, including, inter alia, those described above, will be referred to herein as "transformation." The cells into which have been introduced nucleic acids described above are meant to also include the progeny of such cells.

Large quantities of the nucleic acids and polypeptides of the present invention may be prepared by expressing the KVLQT1 or KCNE1 nucleic acid or portions thereof in vectors or other expression vehicles in compatible prokaryotic or eukaryotic host cells. The most commonly used prokaryotic hosts are strains of *Escherichia coli,* although other prokaryotes, such as *Bacillus subtilis* or Pseudomonas may also be used.

Mammalian or other eukaryotic host cells, such as those of yeast, filamentous fungi, plant, insect, or amphibian or avian species, may also be useful for production of the proteins of the present invention. Propagation of mammalian cells in culture is per se well known. See, Jakoby and Pastan (eds.)(1979). Examples of commonly used manmmalian host cell lines are VERO and HeLa cells, Chinese hamster ovary (CHO) cells, and WI38, BHK, and COS cell lines, although it will be appreciated by the skilled practitioner that other cell lines may be appropriate, e.g., to provide higher expression, desirable glycosylation patterns, or other features. An example of a commonly used insect cell line is SF9.

Clones are selected by using markers depending on1 the mode of the vector construction. The marker may be on the same or a different DNA molecule, preferably the same DNA molecule. In prokaryotic hosts, the transformant may be selected, e.g., by resistance to ampicillin, tetracycline or other antibiotics. Production of a particular product based on temperature sensitivity may also serve as an appropriate marker.

Prokaryotic or eukaryotic cells transformed with the polynucleotides of the present invention will be useful not only for the production of the nucleic acids and polypeptides of the present invention, but also, for example, in studying the characteristics of KVLQT1 or KCNE1 polypeptides.

The probes and primers based on the KVLQT1 or KCNE1 gene sequence disclosed herein are used to identify homologous KVLQT1 or KCNE1 gene sequences and proteins in other species. These gene sequences and proteins are used in the diagnostic/prognostic, therapeutic and drug screening methods described herein for the species from which they have been isolated.

Methods of Use: Drug Screening

The invention is particularly useful for screening compounds by using KVLQT1 and KCNE1 proteins in transformed cells, transfected oocytes or transgenic animals. Since mutations in either the KVLQT1 or KCNE1 protein can alter the functioning of the cardiac $I_{Ks}$ potassium channel, candidate drugs are screened for effects on the channel using cells containing either a normal KVLQT1 or KCNE1 protein and a mutant KCNE1 or KVLQT1 protein, respectively, or a mutant KVLQT1 and a mutant KCNE1 protein. The drug is added to the cells in culture or administered to a transgenic animal and the effect on the induced current of the $I_{Ks}$ potassium channel is compared to the induced current of a cell or animal containing the wild-type KVLQT1 and minK. Drug candidates which alter the induced current to a more normal level are useful for treating or preventing LQT.

This invention is particularly useful for screening compounds by using the KVLQT1 or KCNE1 polypeptide or binding fragment thereof in any of a variety of drug screening techniques.

The KVLQT1 or KCNE1 polypeptide or fragment employed in such a test may either be free in solution, affixed to a solid support, or borne on a cell surface. One method of drug screening utilizes eucaryotic or procaryotic host cells which are stably transformed with recombinant polynucleotides expressing the polypeptide or fragment, preferably in competitive binding assays. Such cells, either in viable or fixed form, can be used for standard binding assays. One may measure, for example, for the formation of complexes between a KVLQT1 or KCNE1 polypeptide or fragment and the agent being tested, or examine the degree to which the formation of a complex between a KVLQT1 or KCNE1 polypeptide or fragment and a known ligand is interfered with by the agent being tested.

Thus, the present invention provides methods of screening for drugs comprising contacting such an agent with a KVLQT1 or KCNE1 polypeptide or fragment thereof and assaying (i) for the presence of a complex between the agent and the KVLQT1 or KCNE1 polypeptide or fragment, or (ii) for the presence of a complex between the KVLQT1 or KCNE1 polypeptide or fragment and a ligand, by methods well known in the art. In such competitive binding assays the KVLQT1 or KCNE1 polypeptide or fragment is typically labeled. Free KVLQT1 or KCNE1 polypeptide or fragment is separated from that present in a protein:protein complex, and the amount of free (i.e.. uncomplexed) label is a measure of the binding of the agent being tested to KVLQT1 or KCNE1 or its interference with KVLQT1 or KCNE1:ligand binding, respectively. One may also measure the amount of bound, rather than free, KVLQT1 or KCNE1. It is also possible to label the ligand rather than the KVLQT1 or KCNE1 and to measure the amount of ligand binding to KVLQT1 or KCNE1 in the presence and in the absence of the drug being tested.

Another technique for drug screening provides high throughput screening for compounds having suitable binding affinity to the KVLQT1 or KCNE1 polypeptides and is described in detail in Geysen (published PCT application WO 84/03564). Briefly stated, large numbers of different small peptide test compounds are synthesized on a solid substrate, such as plastic pins or some other surface. The peptide test compounds are reacted with KVLQT1 or KCNE1 polypeptide and washed. Bound KVLQT1 or KCNE1 polypeptide is then detected by methods well known in the art.

Purified KVLQT1 or KCNE1 can be coated directly onto plates for use in the aforementioned drug screening techniques. However, non-neutralizing antibodies to the polypeptide can be used to capture antibodies to immobilize the KVLQT1 or KCNE1 polypeptide on the solid phase.

This invention also contemplates the use of competitive drug screening assays in which neutralizing antibodies capable of specifically binding the KVLQT1 or KCNE1 polypeptide compete with a test compound for binding to the KVLQT1 or KCNE1 polypeptide or fragments thereof. In this manner, the antibodies can be used to detect the presence of any peptide which shares one or more antigenic determinants of the KVLQT1 or KCNE1 polypeptide.

The above screening methods are not limited to assays employing only KVLQT1 or KCNE1 but are also applicable to studying KVLQT1 or KCNE1-protein complexes. The effect of drugs on the activity of this complex is analyzed.

In accordance with these methods, the following assays are examples of assays which can be used for screening for drug candidates.

A mutant KVLQT1 or KCNE1 (per se or as part of a fusion protein) is mixed with a wild-type protein (per se or as part of a fusion protein) to which wild-type KVLQT1 or KCNE1 binds. This mixing is performed in both the presence of a drug and the absence of the drug, and the amount of binding of the mutant KVLQT1 or KCNE1 with the wild-type protein is measured. If the amount of the binding is more in the presence of said drug than in the absence of said drug, the drug is a drug candidate for treating LQT resulting from a mutation in KVLQT1 or KCNE1.

A wild-type KVLQT1 or KCNE1(per se or as part of a fusion protein) is mixed with a wild-type protein (per se or as part of a fusion protein) to which wild-type KVLQT1 or KCNE1 binds. This mixing is performed in both the presence of a drug and the absence of the drug, and the amount of binding of the wild-type KVLQT1 or KCNE1 with the wild-type protein is measured. If the the amount of the binding is more in the presence of said drug than in the absence of said drug, the drug is a drug candidate for treating LQT resulting from a mutation in KVLQT1 or KCNE1.

A mutant protein, which as a wild-type protein binds to KVLQT1 or KCNE1 (per se or as part of a fusion protein) is mixed with a wild-type KVLQT1 or KCNE1 (per se or as part of a fusion protein). This mixing is preformed in both the presence of a drug and the absence of the drug, and the amount of binding of the mutant protein with the wild-type KVLQT1 or KCNE1 is measured. If the amount of the binding is more in the presence of said drug than in the absence of said drug, the drug is a drug candidate for treating LQT resulting from a mutation in the gene encoding the protein.

The polypeptide of the invention may also be used for screening compounds developed as a result of combinatorial library technology. Combinatorial library technology provides an efficient way of testing a potential vast number of different substances for ability to modulate activity of a polypeptide. Such libraries and their use are known in the art. The use of peptide libraries is preferred. See, for example, WO 97/02048.

Briefly, a method of screening for a substance which modulates activity of a polypeptide may include contacting one or more test substances with the polypeptide in a suitable reaction medium, testing the activity of the treated polypeptide and comparing that activity with the activity of the polypeptide in comparable reaction medium untreated with the test substance or substances. A difference in activity between the treated and untreated polypeptides is indicative of a modulating effect of the relevant test substance or substances.

Prior to or as well as being screened for modulation of activity, test substances may be screened for ability to interact with the polypeptide, e.g., in a yeast two-hybrid system (e.g., Bartel et al., 1993; Fields and Song, 1989; Chevray and Nathans, 1992; Lee et al., 1995). This system may be used as a coarse screen prior to testing a substance for actual ability to modulate activity of the polypeptide. Alternatively, the screen could be used to screen test substances for binding to an KVLQT1 or KCNE1 specific binding partner, or to find mimetics of the KVLQT1 or KCNE1 polypeptide.

Following identification of a substance which modulates or affects polypeptide activity the substance may be investigated further. Furthermore, it may be manufactured and/or used in preparation, i.e., manufacture or formulation, or a composition such as a medicament, pharmaceutical composition or drug. These may be administered to individuals.

Thus, the present invention extends in various aspects not only to a substance identified using a nucleic acid molecule as a modulator of polypeptide activity, in accordance with what is disclosed herein, but also a pharmaceutical composition, medicament, drug or other composition comprising such a substance, a method comprising administration of such a composition comprising such a substance, a method comprising administration of such a composition to a patient, e.g., for treatment (which may include preventative treatment) of LQT, use of such a substance in the manufacture of a composition for administration, e.g., for treatment of LQT, and a method of making a pharmaceutical composition comprising admixing such a substance with a pharmaceutically acceptable excipient, vehicle or carrier, and optionally other ingredients.

A substance identified as a modulator of polypeptide function may be peptide or non-peptide in nature, Non-peptide "small molecules" are often preferred for many in vivo pharmaceutical uses. Accordingly, a mimetic or mimic of the substance (particularly if a peptide) may be designed for pharmaceutical use.

The designing of mimetics to a known pharmaceutically active compound is a known approach to the development of pharmaceuticals based on a "lead" compound. This might be desirable where the active compound is difficult or expensive to synthesize or where it is unsuitable for a particular method of administration, e.g., pure peptides are unsuitable active agents for oral compositions as they tend to be quickly degraded by protease in the alimentary canal. Mimetic design, synthesis and testing is generally used to avoid randomly screening large numbers of molecules for a target property.

There are several steps commonly taken in the design of a mimetic from a compound having a given target property. First the particular parts of the compound that are critical and/or important in determining the target property are determined. In the case of a peptide, this can be done by systematically varying the amino acid residues in the peptide, e.g., by substituting each residue in turn. Alanine scans of peptide are commonly used to refine such peptide motifs. These parts or residues constituting the active region of the compound are known as its "pharmacophore".

Once the pharmacophore has been found, its structure is modeled according to its physical properties, e.g., stereochemistry, bonding, size and/or charge, using data from a range of sources. e.g., spectroscopic techniques, x-ray diffraction data and NMR. Computational analysis, similarity mapping (which models the charge and/or volume of a pharmacophore, rather than the bonding between atoms) and other techniques can be used in this modeling process.

In a variant of this approach, the three-dimensional structure of the ligand and its binding partner are modeled. This can be especially useful where the ligand and/or binding partner change conformation on binding, allowing the model to take account of this in the design of the mimetic.

A template molecule is then selected onto which chemical groups which mimic the pharmacophore can be grafted. The template molecule and the chemical groups grafted onto it can conveniently be selected so that the mimetic is easy to synthesize, is likely to be pharmacologically acceptable, and does not degrade in vivo, while retaining the biological activity of the lead compound. Alternatively, where the mimetic is peptide-based, further stability can be achieved by cycling the peptide, increasing its rigidity. The mimetic or mimetics found by this approach can then be screened to see whether they have the target property, or to what extent they exhibit it. Further optimization or modification can then be carried out to arrive at one or more final mimetics for in vivo or clinical testings Methods of Use: Nucleic Acid Diagnosis and Diagnostic Kits In order to detect the presence of a KVLQT1 or KCNE1 allele predisposing an individual to LQT, a biological sample such as blood is prepared and analyzed for the presence or absence of susceptibility alleles of KVLQT1 or KCNE1. In order to detect the presence of LQT or as a prognostic indicator, a biological sample is prepared and analyzed for the presence or absence of mutant alleles of KVLQT1 or KCNE1. Results of these tests and interpretive information are returned to the health care provider for communication to the tested individual. Such diagnoses may be performed by diagnostic laboratories, or, alternatively, diagnostic kits are manufactured and sold to health care providers or to private individuals for self-diagnosis.

Initially, the screening method involves amplification of the relevant KVLQT1 or KCNE1 sequences. In another preferred embodiment of the invention, the screening method involves a non-PCR based strategy. Such screening methods include two-step label amplification methodologies that are well known in the art. Both PCR and non-PCR based screening strategies can detect target sequences with a high level of sensitivity.

The most popular method used today is target amplification. Here, the target nucleic acid sequence is amplified with polymerases. One particularly preferred method using polymerase-driven amplification is the polymerase chain reaction (PCR). The polymerase chain reaction and other polymerase-driven amplification assays can achieve over a million-fold increase in copy number through the use of polymerase-driven amplification cycles. Once amplified, the resulting nucleic acid can be sequenced or used as a substrate for DNA probes.

When the probes are used to detect the presence of the target sequences the biological sample to be analyzed, such as blood or serum, may be treated, if desired, to extract the nucleic acids. The sample nucleic acid may be prepared in various ways to facilitate detection of the target sequence, e.g., denaturation, restriction digestion, electrophoresis or dot blotting. The targeted region of the analyte nucleic acid usually must be at least partially single-stranded to form hybrids with the targeting sequence of the probe. If the sequence is naturally single-stranded, denaturation will not be required. However, if the sequence is double-stranded, the sequence will probably need to be denatured. Denaturation can be carried out by various techniques known in the art.

Analyte nucleic acid and probe are incubated under conditions which promote stable hybrid formation of the target sequence in the probe with the putative targeted sequence in the analyte. The region of the probes which is used to bind to the analyte can be made completely complementary to the targeted region of human chromosome 11 for KVLQT1 or chromosome 21 for KCNE1. Therefore, high stringency conditions are desirable in order to prevent false positives. However, conditions of high stringency are used only if the probes are complementary to regions of the chromosome which are unique in the genome. The stringency of hybridization is determined by a number of factors during hybridization and during the washing procedure, including temperature, ionic strength, base composition, probe length, and concentration of formamide. These factors are outlined in, for example, Maniatis et al., 1982 and Sambrook et al., 1989. Under certain circumstances, the formation of higher order hybrids, such as triplexes, quadraplexes, etc., may be desired to provide the means of detecting target sequences.

Detection, if any, of the resulting hybrid is usually accomplished by the use of labeled probes. Alternatively, the probe may be unlabeled, but may be detectable by specific binding with a ligand which is labeled, either directly or indirectly. Suitable labels, and methods for labeling probes and ligands are known in the art, and include, for example, radioactive labels which may be incorporated by known methods (e.g.. nick translation, random priming or kinasing), biotin, fluorescent groups, chemiluminescent groups (e.g., dioxetanes, particularly triggered dioxetanes). enzymes, antibodies, gold nanoparticles and the like. Variations of this basic scheme are known in the art, and include those variations that facilitate separation of the hybrids to be detected from extraneous materials and/or that amplify the signal from the labeled moiety. A number of these variations are reviewed in, e.g., Matthews and Kricka, 1988; Landegren et al., 1988; Mifflin, 1989: U.S. Pat. No. 4,868,105; and in EPO Publication No. 225,807.

As noted above, non-PCR based screening assays are also contemplated in this invention. This procedure hybridizes a nucleic acid probe (or an analog such as a methyl phosphonate backbone replacing the normal phosphodiester), to the low level DNA target. This probe may have an enzyme covalently linked to the probe, such that the covalent linkage does not interfere with the specificity of the hybridization. This enzyme-probe-conjugate-target nucleic acid complex can then be isolated away from the free probe enzyme conjugate and a substrate is added for enzyme detection. Enzymatic activity is observed as a change in color development or luminescent output resulting in a $10^3$–$10^6$ increase in sensitivity. For an example relating to the preparation of oligodeoxynucleotide-alkaline phosphatase conjugates and their use as hybridization probes, see Jablonski et al. (1986).

Two-step label amplification methodologies are known in the art. These assays work on the principle that a small ligand (such as digoxigenin, biotin, or the like) is attached to a nucleic acid probe capable of specifically binding KVLQT1. Allele specific probes are also contemplated within the scope of this example and exemplary allele specific probes include probes encompassing the predisposing mutations of this patent application.

In one example, the small ligand attached to the nucleic acid probe is specifically recognized by an antibody-enzyme conjugate. In one embodiment of this example, digoxigenin is attached to the nucleic acid probe. Hybridization is detected by an antibody-alkaline phosphatase conjugate which turns over a chemiluminescent substrate. For methods for labeling nucleic acid probes according to this embodiment see Martin et al., 1990. In a second example, the small ligand is recognized by a second ligand-enzyme conjugate that is capable of specifically complexing to the first ligand. A well known embodiment of this example is the biotin-avidin type of interactions. For methods for labeling nucleic acid probes and their use in biotin-avidin based assays see Rigby et al., 1977 and Nguyen et al., 1992.

It is also contemplated within the scope of this invention that the nucleic acid probe assays of this invention will employ a cocktail of nucleic acid probes capable of detecting KVLQT1 or KCNE1. Thus, in one example to detect the presence of KVLQT1 or KCNE1 in a cell sample, more than one probe complementary to the gene is employed and in particular the number of different probes is alternatively two, three, or five different nucleic acid probe sequences. In another example, to detect the presence of mutations in the KVLQT1 or KCNE1 gene sequence in a patient, more than one probe complementary to these genes is employed where the cocktail includes probes capable of binding to the allele-specific mutations identified in populations of patients with alterations in KVLQT1 or KCNE1. In this embodiment, any number of probes can be used, and will preferably include probes corresponding to the major gene mutations identified as predisposing an individual to LQT.

Methods of Use: Peptide Diagnosis and Diagnostic Kits

The presence of LQT can also be detected on the basis of the alteration of wild-type KVLQT1 or KCNE1 polypeptide. Such alterations can be determined by sequence analysis in accordance with conventional techniques. More preferably, antibodies (polyclonal or monoclonal) are used to detect differences in, or the absence of KVLQT1 or KCNE1 peptides. Techniques for raising and purifying antibodies are well known in the art and any such techniques may be chosen to achieve the preparations claimed in this invention. In a preferred embodiment of the invention, antibodies will immunoprecipitate KVLQT1 or KCNE1 proteins from solution as well as react with these proteins on Western or immunoblots of polyacrylamide gels. In another preferred embodiment, antibodies will detect KVLQT1 or KCNE1 proteins in paraffin or frozen tissue sections, using immunocytochemical techniques.

Preferred embodiments relating to methods for detecting KVLQT1 or KCNE1 or their mutations include enzyme linked immunosorbent assays (ELISA), radioimmunoassays (RIA), immunoradiometric assays (IRMA) and immunoenzymatic assays (IEMA), including sandwich assays using monoclonal and/or polyclonal antibodies. Exemplary sandwich assays are described by David et al., in U.S. Pat. Nos. 4,376,110 and 4,486.530, hereby incorporated by reference.

Methods of Use: Rational Drug Design

The goal of rational drug design is to produce structural analogs of biologically active polypeptides of interest or of small molecules with which they interact (e.g., agonists, antagonists, inhibitors) in order to fashion drugs which are, for example, more active or stable forms of the polypeptide, or which, e.g., enhance or interfere with the function of a polypeptide in vivo. See, e.g., Hodgson, 1991. In one approach, one first determines the three-dimensional structure of a protein of interest (e.g., KVLQT1 or KCNE1 polypeptide) by x-ray crystallography, by computer modeling or most typically, by a combination of approaches. Less often, useful information regarding the structure of a polypeptide may be gained by modeling based on the structure of homologous proteins. An example of rational drug design is the development of HIV protease inhibitors (Erickson et al., 1990). In addition, peptides (e.g., KVLQT1 or KCNE1 polypeptide) are analyzed by an alanine scan (Wells, 1991). In this technique, an amino acid residue is replaced by Ala, and its effect on the peptide's activity is determined. Each of the amino acid residues of the peptide is analyzed in this manner to determine the important regions of the peptide.

It is also possible to isolate a target-specific antibody, selected by a functional assay, and then to solve its crystal structure. In principle, this approach yields a pharmacore upon which subsequent drug design can be based. It is possible to bypass protein crystallography altogether by generating anti-idiotypic antibodies (anti-ids) to a functional, pharmacologically active antibody. As a mirror image of a mirror image, the binding site of the anti-ids would be expected to be an analog of the original receptor. The anti-id could then be used to identify and isolate peptides from banks of chemically or biologically produced banks of peptides. Selected peptides would then act as the pharmacore.

Thus, one may design drugs which have, e.g., improved KVLQT1 or KCNE1 polypeptide activity or stability or which act as inhibitors, agonists, antagonists, etc. of KVLQT1 or KCNE1 polypeptide activity. By virtue of the availability of cloned KVLQT1 or KCNE1 sequences, sufficient amounts of the KVLQT1 or KCNE1 polypeptide may be made available to perform such analytical studies as x-ray crystallography. In addition, the knowledge of the KVLQT1 or KCNE1 protein sequences provided herein will guide those employing computer modeling techniques in place of, or in addition to x-ray crystallography.

Methods of Use: Gene Therapy

According to the present invention, a method is also provided of supplying wild-type KVLQT1 or KCNE1 function to a cell which carries a mutant KVLQT1 or KCNE1 allele, respectively. Supplying such a function should allow normal functioning of the recipient cells. The wild-type gene or a part of the gene may be introduced into the cell in a vector such that the gene remains extrachromosomal. In such a situation, the gene will be expressed by the cell from the extrachromosomal location. More preferred is the situation where the wild-type gene or a part thereof is introduced into the mutant cell in such a way that it recombines with the endogenous mutant gene present in the cell. Such recombination requires a double recombination event which results in the correction of the gene mutation. Vectors for introduction of genes both for recombination and for extrachromosomal maintenance are known in the art, and any suitable vector may be used. Methods for introducing DNA into cells such as electroporation, calcium phosphate co-precipitation and viral transduction are known in the art, and the choice of method is within the competence of the practitioner.

As generally discussed above, the KVLQT1 or KCNE1 gene or fragment, where applicable, may be employed in gene therapy methods in order to increase the amount of the expression products of such gene in cells. It may also be useful to increase the level of expression of a given LQT gene even in those heart cells in which the mutant gene is expressed at a "normal" level, but the gene product is not fully functional.

Gene therapy would be carried out according to generally accepted methods, for example, as described by Friedman (1991) or Culver (1996). Cells from a patient would be first analyzed by the diagnostic methods described above, to ascertain the production of KVLQT1 or KCNE1 polypeptide in the cells. A virus or plasmid vector (see further details below), containing a copy of the KVLQT1 or KCNE1 gene linked to expression control elements and capable of replicating inside the cells, is prepared. The vector may be capable of replicating inside the cells. Alternatively, the vector may be replication deficient and is replicated in helper cells for use in gene therapy. Suitable vectors are known, such as disclosed in U.S. Pat. No. 5,252,479 and PCT published application WO 93/07282 and U.S. Pat. Nos. 5,691,198; 5,747,469; 5,436,146 and 5,753,500. The vector is then injected into the patient. If the transfected gene is not permanently incorporated into the genome of each of the targeted cells, the treatment may have to be repeated periodically.

Gene transfer systems known in the art may be useful in the practice of the gene therapy methods of the present invention. These include viral and nonviral transfer methods. A number of viruses have been used as gene transfer vectors or as the basis for repairing gene transfer vectors, including papovaviruses (e.g., SV40, Madzak et al., 1992), adenovirus (Berkner, 1992; Berkner et al., 1988; Gorziglia and Kapikian, 1992; Quantin et al., 1992; Rosenfeld et al., 1992; Wilkinson and Akrigg, 1992; Stratford-Perricaudet et al., 1990; Schneider et al., 1998), vaccinia virus (Moss, 1992; Moss, 1996), adeno-associated virus (Muzyczka, 1992; Ohi et al., 1990; Russell and Hirata, 1998), herpesviruses including HSV and EBV (Margolskee, 1992; Johnson et al., 1992; Fink et al., 1992; Breakefield and Geller, 1987; Freese et al., 1990; Fink et al., 1996), lentiviruses (Naldini et al., 1996), Sindbis and Semliki Forest virus (Berglund et al., 1993), and retroviruses of avian (Bandyopadhyay and Temin, 1984; Petropoulos et al., 1992), murine (Miller, 1992; Miller et al., 1985; Sorge et al., 1984; Mann and Baltimore, 1985; Miller et al., 1988), and human origin (Shimada et al., 1991; Helseth et al., 1990; Page et al., 1990; Buchschacher and Panganiban, 1992). Most human gene therapy protocols have been based on disabled murine retroviruses, although adenovirus and adeno-associated virus are also being used.

Nonviral gene transfer methods known in the art include chemical techniques such as calcium phosphate coprecipitation (Graham and van der Eb, 1973; Pellicer et al., 1980); mechanical techniques, for example microinjection (Anderson et al., 1980; Gordon et al., 1980; Brinster et al., 1981; Costantini and Lacy, 1981); membrane fusion-mediated transfer via liposomes (Felgner et al., 1987; Wang and Huang, 1989; Kaneda et al., 1989; Stewart et al., 1992; Nabel et al., 1990; Lim et al., 1991); and direct DNA uptake and receptor-mediated DNA transfer (Wolff et al., 1990; Wu et al., 1991; Zenke et al., 1990; Wu et al., 1989; Wolff et al., 1991; Wagner et al., 1990; Wagner et al., 1991; Cotten et al., 1990; Curiel et al., 1992; Curiel et al., 1991). Viral-mediated gene transfer can be combined with direct in vivo gene transfer using liposome delivery, allowing one to direct the viral vectors to the tumor cells and not into the surrounding nondividing cells. Alternatively, the retroviral vector producer cell line can be injected into tumors (Culver et al., 1992). Injection of producer cells would then provide a continuous source of vector particles. This technique has been approved for use in humans with inoperable brain tumors.

In an approach which combines biological and physical gene transfer methods, plasmid DNA of any size is combined with a polylysine-conjugated antibody specific to the adenovirus hexon protein, and the resulting complex is bound to an adenovirus vector. The trimolecular complex is then used to infect cells. The adenovirus vector permits efficient binding, internalization, and degradation of the endosome before the coupled DNA is damaged. For other techniques for the delivery of adenovirus based vectors see Schneider et al. (I 998) and U.S. Pat. Nos. 5,691,198; 5,747,469; 5,436,146 and 5,753,500.

Liposome/DNA complexes have been shown to be capable of mediating direct in vivo gene transfer. While in standard liposome preparations the gene transfer process is nonspecific, localized in vivo uptake and expression have been reported in tumor deposits, for example, following direct in situ administration (Nabel, 1992).

Expression vectors in the context of gene therapy are meant to include those constructs containing sequences sufficient to express a polynucleotide that has been cloned therein. In viral expression vectors, the construct contains viral sequences sufficient to support packaging of the construct. If the polynucleotide encodes KVLQT1 or KCNE1, expression will produce KVLQT1 or KCNE1. If the polynucleotide encodes an antisense polynucleotide or a ribozyme, expression will produce the antisense polynucleotide or ribozyme. Thus in this context, expression does not require that a protein product be synthesized. In addition to the polynucleotide cloned into the expression vector, the vector also contains a promoter functional in eukaryotic cells. The cloned polynucleotide sequence is under control of this promoter. Suitable eukaryotic promoters include those described above. The expression vector may also include sequences, such as selectable markers and other sequences described herein.

Gene transfer techniques which target DNA directly to heart tissue is preferred. Receptor-mediated gene transfer, for example, is accomplished by the conjugation of DNA (usually in the form of covalently closed supercoiled plasmid) to a protein ligand via polylysine. Ligands are chosen on the basis of the presence of the corresponding ligand receptors on the cell surface of the target cell/tissue type. These ligand-DNA conjugates can be injected directly into the blood if desired and are directed to the target tissue where receptor binding and internalization of the DNA-protein complex occurs. To overcome the problem of intracellular destruction of DNA, coinfection with adenovirus can be included to disrupt endosome function.

The therapy is as follow: patients who carry a KVLQT1 or KCNE1 susceptibility allele are treated with a gene delivery vehicle such that some or all of their heart precursor cells receive at least one additional copy of a functional normal KVLQT1 or KCNE1 allele. In this step, the treated individuals have reduced risk of LQT to the extent that the effect of the susceptible allele has been countered by the presence of the normal allele.

Methods of Use: Peptide Therapy

Peptides which have KVLQT1 or KCNE1 activity can be supplied to cells which carry a mutant or missing KVLQT1 or KCNE1 allele. Protein can be produced by expression of the cDNA sequence in bacteria, for example, using known expression vectors. Alternatively, KVLQT1 or KCNE1 polypeptide can be extracted from KVLQT1- or KCNE1-producing mammalian cells. In addition, the techniques of synthetic chemistry can be employed to synthesize KVLQT1 or KCNE1 protein. Any of such techniques can provide the preparation of the present invention which comprises the KVLQT1 or KCNE1 protein. The preparation is substantially free of other human proteins. This is most readily accomplished by synthesis in a microorganism or in vitro.

Active KVLQT1 or KCNE1 molecules can be introduced into cells by microinjection or by use of liposomes, for example. Alternatively, some active molecules may be taken up by cells. actively or by diffusion. Supply of molecules with KVLQT1 or KCNE1 activity should lead to partial reversal of LQT. Other molecules with KVLQT1 or KCNE1 activity (for example, peptides, drugs or organic compounds) may also be used to effect such a reversal. Modified polypeptides having substantially similar function are also used for peptide therapy.

Methods of Use: Transformed Hosts

Animals for testing therapeutic agents can be selected after mutagenesis of whole animals or after treatment of germline cells or zygotes. Such treatments include insertion of mutant KVLQT1 and/or KCNE1 alleles, usually from a second animal species, as well as insertion of disrupted homologous genes. Alternatively, the endogenous KVLQT1 or KCNE1 gene of the animals may be disrupted by insertion or deletion mutation or other genetic alterations using conventional techniques (Capecchi. 1989; Valancius and Smithies, 1991; lHasty et al., 1991; Shinkai et al., 1992; Mombaerts et al., 1992 Philpott et al., 1992 Snouwaert et al., 1992; Donehower et al., 1992). After test substances have been administered to the animals, the presence of LQT must be assessed. If the test substance prevents or suppresses the appearance of LQT, then the test substance is a candidate therapeutic agent for treatment of LQT. These animal models provide an extremely important testing vehicle for potential therapeutic products.

Two strategies had been utilized herein to idenitify LQT genes, a candidate gene approach and positional cloning. Positional information is now available for three LQT loci with LQT1 having been mapped to chromosome 11p15.5 (Keating et al., 1991a; Keating et al., 1991b), LQT2 to 7q35–36 and LQT3 to 3p21–24 (Jiang et al., 1994). The present invention has also identified minK, on chromosome 21, as an LQT gene. The candidate gene approach relies on likely mechanistic hypotheses based on physiology. Although little is known about the physiology of LQT, the disorder is associated with prolongation of the QT interval on electrocardiograms, a sign of abnormal cardiac repolarization. This association suggests that genes encoding ion channels, or their modulators, are reasonable candidates for LQT. This hypothesis is now supported by the discovery that chromosome 7-linked LQT results from mutations in HERG, a putative cardiac potassium channel gene. A neuroendocrine calcium channel gene (CACN1A2; Chin et al., 1991: Seino et al., 1992) and a gene encoding a GTP-binding protein that modulates potassium channels (GNAI2; Weinstein et al., 1988; Magovcevic et al., 1992) became candidates for LQT3 based on their chromosomal locaton. Subsequent linkage analyses, however, have excluded these genes. It has now been shown that LQT3 is associated faith SCN5A (Wang et al., 1995a). Despite considerable effort, however, a candidate gene approach to chromosome 11-linked LQT has not been successful. Two potassium channel genes (KCNA4 and KCNC1) were mapped to the short arm of chromosome 11 (Wymore et al., 1994), but both were excluded as candidates for LQT1 by linkage analyses (Russell et al., 1995; the present study). All other previously characterized cardiac potassium, chloride, sodium and calcium channel genes were similarly excluded based on their chromosomal locations. The present study has used positional cloning and mutational analyses to identify LQT1.

The present invention has used genotypic analyses to show that KVLQT1 is tightly linked to LQT1 in 16 unrelated families (details provided in the Examples). KVLQT1 is a putative cardiac potassium channel gene and causes the chromosome 11-linked form of LQT. Genetic analyses suggested that KVLQT1 encodes a voltage-gated potassium channel with functional importance in cardiac repolarization and it is now shown that KVLQT1 coassembles with KCNE1 to form a cardiac $I_{Ks}$ potassium channel. If correct, the mechanism of chromosome 11-linked LQT probably involves reduced repolarizing KVLQT1 current. Since potassium channels with six transmembrane domains are thought to be formed from homo- or hetero-tetrameters (MacKinnion, 1991; MacKinnon et al., 1 993; Covarrubias et al., 1991), it is possible that LQT-associated mutations of KVLQT1 act through a dominant-negative mechanism. The type and location of KVLQT1 mutations described here are consistent with this hypothesis. The resultant suppression of potassium channel function, in turn, would likely lead to abnormal cardiac repolarization and increased risk of ventricular tachyarrhythmias. The mutations identified in HERG, and the biophysics of potassium channel alpha subunits, suggest that chromosome 7-linked LQT results from dominant-negative mutations and a resultant reduction in functional channels. In chromosome 3-linked LQT, by contrast, the LQT-associated deletions identified in SCN5A are likely to result in functional cardiac sodium channels with altered properties, such as delayed inactivation or altered voltage-dependence of channel inactivation. Delayed sodium channel inactivation would increase inward sodium current, depolarizing the membrane. This effect is similar to the altered membrane potential expected from HERG mutations where outward potassium current is decreased. It is unlikely that more deleterious mutations of SCN5A would cause LQT. A reduction of the total number of cardiac sodium channels, for example, would be expected to reduce action potential duration, a phenotype opposite that of LQT.

Presymptomatic diagnosis of LQT has depended on identification of QT prolongation on electrocardiograms. Unfortunately, electrocardiograms are rarely performed in young, healthy individuals. In addition, many LQT gene carriers have relatively normal QT intervals, and the first sign of disease can be a fatal cardiac arrhythmia (Vincent et al., 1992). Now that more LQT genes (KVLQT1 and KCNE1) have been identified and have been associated with LQT, genetic testing for this disorder can be contemplated. This will require continued mutational analyses and identification of additional LQT genes. With more detailed phenotypic analyses, phenotypic differences between the varied forms of LQT may be discovered. These differences may be useful for diagnosis and treatment.

The identification of the association between the KVLQT1 and KCNE1 gene mutations and LQT permits the early presymptomatic screening of individuals to identify those at risk for developing LQT. To identify such individuals, the KVLQT1 and/or KCNE1 alleles are screened for mutations either directly or after cloning the alleles. The alleles are tested for the presence of nucleic acid sequence differences from the normal allele using any suitable technique, including but not limited to, one of the following methods: fluorescent in situ hybridization (FISH), direct DNA sequencing, PFGE analysis, Southern blot analysis, single stranded conformation analysis (SSCP), linkage analysis, RNase protection assay, allele specific oligonucleotide (ASO), dot blot analysis and PCR-SSCP analysis. Also useful is the recently developed technique of DNA microchip technology. For example, either (1) the nucleotide sequence of both the cloned alleles and normal KVLQT1 or KCNE1 gene or appropriate fragment (coding sequence or genomic sequence) are determined and then compared, or (2) the RNA transcripts of the KVLQT1 or KCNE1 gene or gene fragment are hybridized to single stranded whole genomic DNA from an individual to be tested, and the resulting heteroduplex is treated with Ribonuclease A (RNase A) and run on a denaturing gel to detect the location of any mismatches. Two of these methods can be carried out according to the following procedures.

The alleles of the KVLQT1 or KCNE1 gene in an individual to be tested are cloned using conventional techniques. For example, a blood sample is obtained from the individual. The genomic DNA isolated from the cells in this sample is partially digested to an average fragment size of approximately 20 kb. Fragments in the range from 18–21 kb are isolated. The resulting fragments are ligated into an appropriate vector. The sequences of the clones are then determined and compared to the normal KVLQT1 or KCNE1 gene.

Alternatively, polymerase chain reactions (PCRs) are performed with primer pairs for the 5' region or the exons of the KVLQT1 or KCNE1 gene. PCRs can also be performed with primer pairs based on any sequence of the normal KVLQT1 or KCNE1 gene. For example, primer pairs for one of the introns can be prepared and utilized. Finally, RT-PCR can also be performed on the mRNA. The amplified products are then analyzed by single stranded conformation polymorphisms (SSCP) using conventional techniques to identify any differences and these are then sequenced and compared to the normal gene sequence.

Individuals can he quickly screened for common KVLQT1 or KCNE1 gene variants by amplifying the individual's DNA using suitable primer pairs and analyzing the amplified product, e.g., by dot-blot hybridization using allele-specific oligonucleotide probes.

The second method employs RNase A to assist in the detection of differences between the normal KVLQT1 or KCNE1 gene and defective genes. This comparison is performed in steps using small (~500 bp) restriction fragments of the KVLQT1 or KCNE1 gene as the probe. First, the KVLQT1 or KCNE1 gene is digested with a restriction enzyme(s) that cuts the gene sequence into fragments of approximately 500 bp. These fragments are separated on an electrophoresis gel, purified from the gel and cloned individually, in both orientations, into an SP6 vector (e.g., pSP64 or pSP65). The SP6-based plasmids containing, inserts of the KVLQT1 or KCNE1 gene fragments are transcribed in vitro using the SP6 transcription system, well known in the art in the presence of $[\alpha\text{-}^{32}\text{P}]\text{GTP}$, generating radiolabeled RNA transcripts of both strands of the gene.

Individually, these RNA transcripts are used to form heteroduplexes with the allelic DNA using conventional techniques. Mismatches that occur in the RNA:DNA heteroduplex, owing to sequence differences between the KVLQT1 or KCNE1 fragment and the KVLQT1 or KCNE1 allele subclone from the individual, result in cleavage in the RNA strand when treated with RNase A. Such mismatches can be the result of point mutations or small deletions in the individual's allele. Cleavage of the RNA strand yields two or more small RNA fragments, which run faster on the denaturing gel than the RNA probe itself.

Any differences which are found, will identify an individual as having a molecular variant of the KVLQT1 or KCNE1 gene and the consequent presence of long QT syndrome. These variants can take a number of forms. The most severe forms would be frame shift mutations or large deletions which would cause the gene to code for an abnormal protein or one which would significantly alter protein expression. Less severe disruptive mutations would include small in-frame deletions and nonconservative base pair substitutions which would have a significant effect on the protein produced, such as changes to or from a cysteine residue, from a basic to an acidic amino acid or vice versa, from a hydrophobic to hydrophilic amino acid or vice versa, or other mutations which would affect secondary or tertiary protein structure. Silent mutations or those resulting in conservative amino acid substitutions would not generally be expected to disrupt protein function.

Genetic testing will enable practitioners to identify individuals at risk for LQT at, or even before, birth. Presymptomatic diagnosis of LQT will enable prevention of these disorders. Existing medical therapies, including beta adrenergic blocking agents, may prevent and delay the onset of problems associated with the disease. Finally, this invention changes our understanding of the cause and treatment of common heart disease like cardiac arrhythmias which account for 11% of all natural deaths. Existing diagnosis has focused on measuring the QT interval from electrocardiograms. This method is not a fully accurate indicator of the presence of long QT syndrome. The present invention is a more accurate indicator of the presence of the disease. Genetic testing and improved mechanistic understanding of LQT provide the opportunity for prevention of life-threatening arrhythmias through rational therapies. It is possible, for example. that potassium channel opening agents will reduce the risk of arrhythmias in patients with KVLQT1 or KCNE1 mutations; sodium channel blocking agents, by contrast, may be a more effective treatment for patients with mutations that alter the function of SCN5A. Finally, these studies may provide insight into mechanisms underlying common arrhythmias, as these arrhythmias are often associated with abnormal cardiac repolarization and may result from a combination of inherited and acquired factors.

Pharmaceutical Compositions and Routes of Administration

The KVLQT1 and KCNE1 polypeptides, antibodies, peptides and nucleic acids of the present invention can be formulated in pharmaceutical compositions, which are prepared according to conventional pharmaceutical compounding techniques. See, for example, *Remington's Pharmaceutical Sciences,* 18th Ed. (1990, Mack Publishing Co., Easton, Pa.). The composition may contain the active agent or pharmaceutically acceptable salts of the active agent. These compositions may comprise, in addition to one of the active substances, a pharmaceutically acceptable excipient, carrier, buffer, stabilizer or other materials well known in the art. Such materials should be non-toxic and should not interfere with the efficacy of the active ingredient. The carrier may take a wide variety of forms depending on the form of preparation desired for administration, e.g., intravenous, oral, intrathecal, epineural or parenteral.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed. such as, for example, water, glycols, oils, alcohols, flavoring agents, preservatives, coloring agents, suspending agents, and the like in the case of oral liquid preparations (such as, for example, suspensions, elixirs and solutions); or carriers Such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agent is preferably administered in a therapeutically effective amount. The actual amount administered, and the rate and time-course of administration, will depend on the nature and severity of the condition being treated. Prescription of treatment, e.g. decisions on dosage, timing, etc., is within the responsibility of general practitioners or specialists, and typically takes account of the disorder to be treated, the condition of the individual patient, the site of delivery, the method of administration and other factors known to practitioners. Examples of techniques and protocols can be found in *Remington's Pharmaceutical Sciences.*

Alternatively, targeting therapies may be used to deliver the active agent more specifically to certain types of cell, by the use of targeting systems such as antibodies or cell specific ligands. Targeting may be desirable for a variety of reasons, e.g. if the agent is unacceptably toxic, or if it would otherwise require too high a dosage, or if it would not otherwise be able to enter the target cells.

Instead of administering these agents directly, they could be produced in the target cell, e.g. in a viral vector such as described above or in a cell based delivery system such as described in U.S. Pat. No. 5,550,050 and published PCT application Nos. WO 92/19195, WO 94/25503, WO 95/01203, WO 95/05452, WO 96/02286, WO 96/02646, WO 96/40871, WO 96/40959 and WO 97/12635, designed for implantation in a patient. The vector could be targeted to the specific cells to be treated, or it could contain regulatory elements which are more tissue specific to the target cells. The cell based delivery system is designed to be implanted in a patient's body at the desired target site and contains a coding sequence for the active agent. Alternatively, the agent could be administered in a precursor form for conversion to the active form by an activating agent produced in, or targeted to, the cells to be treated. See for example, EP 425,73A and WO 901/07936.

The present invention is further detailed in the following Examples, which are offered by way of illustration and are not intended to limit the invention in any manner. Standard techniques well known in the art or the techniques specifically described below are utilized.

EXAMPLE 1

Methods for Phenotypic Evaluation

For these studies, six large LQT kindreds (K1532, K1723, K2605, K1807, K161 and K162) as well as some small kindreds and sporadic cases were studied. LQT patients were identified from medical clinics throughout North America and Europe. Two factors were considered from phenotyping: 1) historical data (the presence of syncope, the number of syncopal episodes, the presence of seizures, the age of onset of symptoms, and the occurrence of sudden death); and 2) the QT interval on electrocardiograms corrected for heart rate ($QT_c$) (Bazzett, 1920). To avoid misclassifying individuals, the same conservative approach to phenotypic assignment that was successful in previous studies was used (Keating et al., 1991a; Keating et al., 1991b; Jiang et al., 1994). Informed consent was obtained from each individual, or their guardians, in accordance with local institutional review board guidelines. Phenotypic data were interpreted without knowledge of genotype. Symptomatic individuals with a corrected QT interval ($QT_c$) of 0.45 seconds or greater and asymptomatic individuals with a $QT_c$ of 0.47 seconds or greater were classified as affected. Asymptomatic individuals with a $QT_c$ of 0.41 seconds or less were classified as unaffected. Asymptomatic individuals with $QT_c$ between 0.41 and 0.47 seconds and symptomatic individuals with $QT_c$ of 0.44 seconds or less were classified as uncertain.

EXAMPLE 2

Genotyping and Linkage Analysis

Genomic DNA was prepared from peripheral blood lymphocytes or cell lines derived from Epstein-Barr virus transformed lymphocytes using standard procedures (Anderson and Gusella, 1984). For genotypic analyses, four small tandem repeat (STR) polymorphisms were used that were previously mapped to chromosome 11p15.5: D11S922, TH, D11S1318 and D11S860 (Gyapay et al., 1994). Genotyping of RFLP markers (HRAS1, D11S454 and D11S12) was performed as previously described (Keating et al., 1991a).

Pair-wise linkage analysis was performed using MLINK in LINKAGE v5.1 (Lathrop et al., 1985). Assumed values of 0.90 for penetrance and 0.001 for LQT gene frequency were used. Gene frequency was assumed to be equal between males and females. Male and female recombination frequencies were considered to be equal. STR allele frequencies were 1/n where n=number of observed alleles. Although the maximum LOD score for D11s454 was identified at a recombination fraction of 0, the presence of one non-obligate recombinant (individual VI-14, FIG. 1) places this LQT gene telomeric of D11S454.

EXAMPLE 3

Physical Mapping

Primers were designed based on sequences from TH-INS-IGFII and D11S454 loci and used to identify and isolate clones from CEPH YAC libraries using the PCR based technique (Green and Olson, 1990; Kwiatkowski et al., 1990). YAC terminal sequences were determined by inverse PCR as described (Ochman et al., 1988) and used as STSs.

P1 clones were isolated using single copy probes from previously identified cosmids cosQW22 (this study), cCI11-469 (D11S679), cCI11-385 (D11S551), cCI11-565 (D11S601), cCI11-237 (D11S454) (Tanigami et al., 1992; Tokino et al., 1991; Sternberg, 1990). Newly isolated P1s were mapped to chromosome 11p15 by FISH or Southern analyses. End-specific riboprobes were generated from newly isolated P1s and used to identify additional adjacent clones (Riboprobe Gemini Core System Kit; Promega). DNA for P1 and cosmid clones was prepared using alkaline lysis plasmid isolation and purified by equilibrium centrifugation in CsCl-ethidium bromide gradients as described (Sambrook et al., 1989). P1 insert end sequences were determined by cycle sequencing as described (Wang and Keating, 1994). STSs were generated based on these insert end sequences. Overlap between P1s and cosmids was calculated by summing the restriction fragments in common.

EXAMPLE 4

Isolation and Characterization of KVLQT1 Clones

An adult human cardiac cDNA library (Stratagene) was plated, and $1 \times 10^6$ plaques were screened using trapped exon 4181A as the probe. Sequences of trapped exon 4181A were used to design oligonucleotide probes for cDNA library screening. The GENETRAPPER™ cDNA Positive Selection System was used to screen $1 \times 10^{11}$ clones from a human heart cDNA library (Life technologies, Inc.). The sequences of the capture and repair oligonucleotides were 5'-CAGATCCTGAGGATGCT-3' (SEQ ID NO:7) and 5'-GTACCTGGCTGAGAAGG-3' (SEQ ID NO:8).

Composite cDNA sequences for KVLQT1 were obtained by end sequencing of overlapping cDNA clones and by primer walking. Sequencing was performed either automatically, using Pharmacia A.L.F. automated sequencers, or manually, using a Sequenase Version 2.0 DNA Sequencing Kit (United States Biochemical, Inc.). Database analyses and sequence analyses were carried out using the GCG software package, IG software package, and the BLAST network service from the National Center for Biotechnology Information.

The partial genomic structure (from transmembrane domain S2 to S6) of KVLQT1 was determined by cycle sequencing of P1 18B12 as described (Wang and Keating, 1994). Primers were designed based on KVLQT1 cDNA sequence and used for cycle sequencing.

EXAMPLE 5

Mutation Analyses

SSCP was carried out as previously described (Wang et al., 1995a; Wang et al., 1995b). Normal and aberrant SSCP products were isolated sequenced directly as described (Wang and Keating, 1994) or subcloned into pBluescript (SK+; Stratagene) using the T-vector method (Marchuk et al., 1991). When the latter method was used, several clones were sequenced by the dideoxy chain termination method using Sequenase™ Version 2.0 (United States Biochemicals, Inc.).

EXAMPLE 6

Northern Analyses

A multiple tissue Northern filter (Human MTN blot 1, Clontech) was probed with a $^{32}$P-labeled KVLQT1 cDNA probe as previously described (Curran et al., 1995)

EXAMPLE 7

Refined Genetic and Physical Localization of LQT1

Figure 1A:
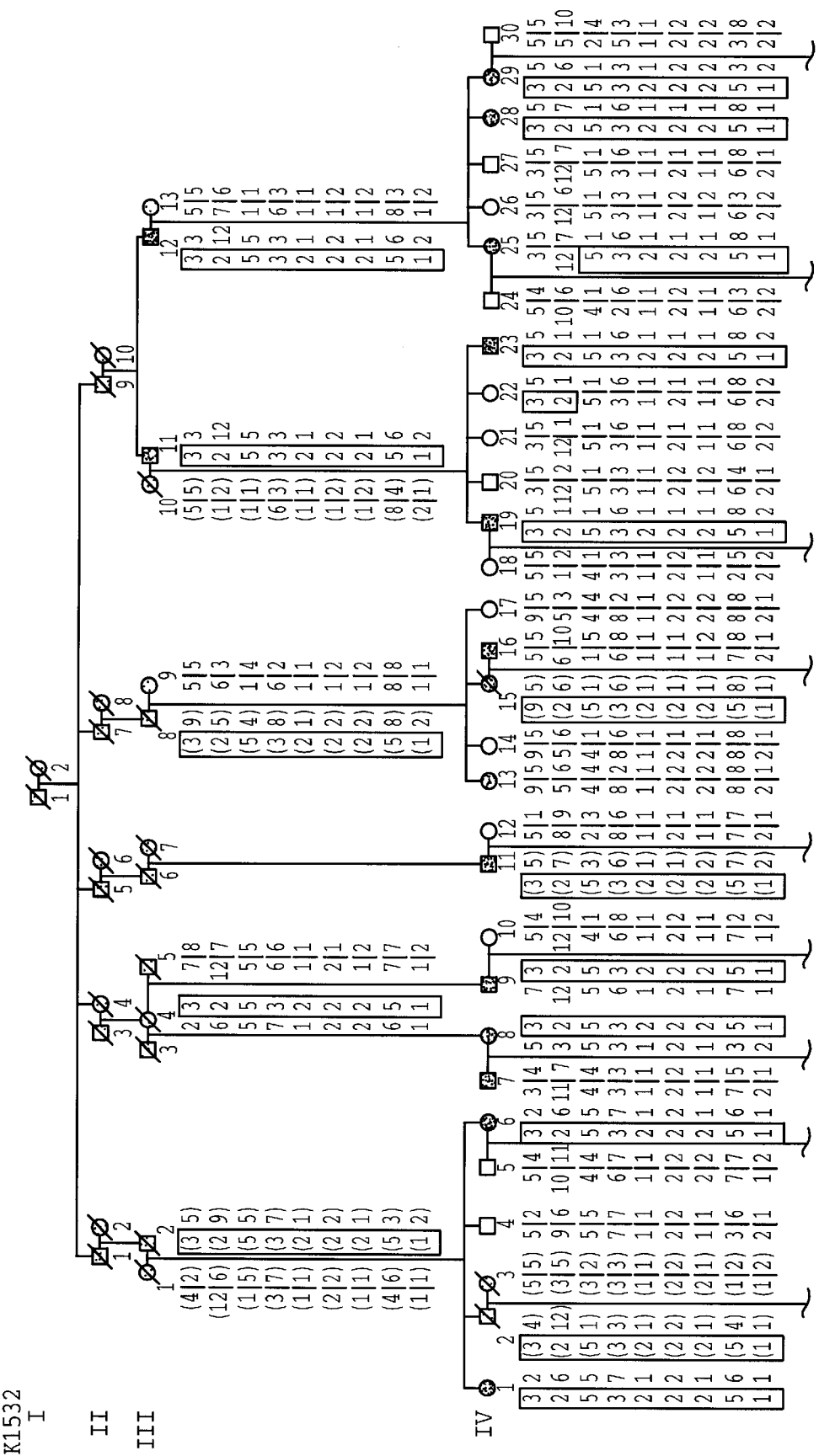
FIG. 1. Pedigree structure for a portion of LQT kindred 1532. Affected individuals are shown as filled circles (females) or squares (males), unaffected individuals as empty symbols and individuals with equivocal phenotypes are stippled. Genotypes for chromosome 11 markers are indicated beneath each symbol and are shown as haplotypes.
Figure 1B:
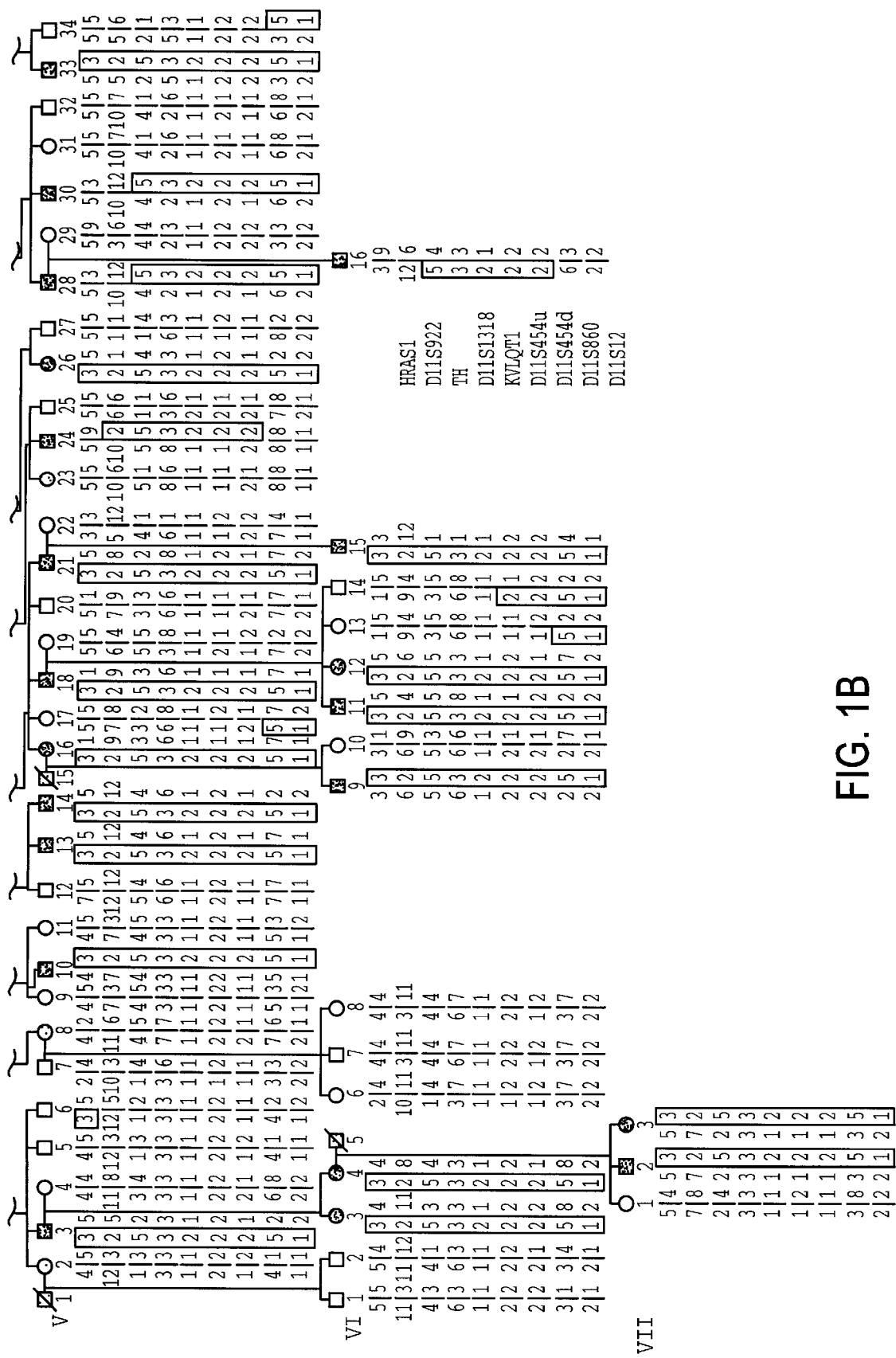

The precise location of LQT1 was determined by genotypic analyses in kindred 1532 (K1532), a large Utah family of northern European descent (FIG. 1). This kindred had been used in the initial study linking the first LQT gene, LQT1, to chromosome 11p15.5 (Keating et al., 1991a; Keating et al., 1991b). Additional family members were identified and phenotyped for a total sample size of 217 individuals. Phenotypic determination was performed as previously described (Keating et al., 1991a; Keating et al., 1991b; Jiang et al., 1994). Preliminary genotypic analyses using markers at HRAS, TH, D11S454, and D11S12 included all ascertained members of K1532. These experiments identified informative branches of this family. Additional genotypic analyses were performed using three highly polymorphic markers from chromosome 11p15.5: D11S922, D11S1318, and D11S860 (Gyapay et al., 1994). Genotypes and pairwise LOD scores for each marker are shown in FIG. 1 and Table 2. Of these markers, TH and D11S1318 were completely linked. Recombination was identified with all other markers tested, including HRAS, but in each case a statistically significant positive LOD score (+3 or greater) was identified. These data indicate that LQT1 is completely linked to TH and D11S$_{1318}$ in this kindred and that the disease gene is located centromeric of HRAS.

To refine localization of LQT1, haplotype analyses of K1532 were performed (see FIG. 1). Nine chromosomes bearing informative recombination events were identified. Telomeric recombination events were observed in unaffected individual IV-22 (between D11S922 and TH), affected individual IV-25 (between D11S922 and TH), unaffected individual V-6 (between HRAS and D11S922), and affected individual V-24 (between HRAS and D11S922). Centromeric recombination events were identified in unaffected individual VI-17 (between D11S860 and D11S454), affected individual V-24 (between D11S860 and D11S454), unaffected individual V-34 (between D11S860 and D11S454), unaffected individual VI-13 (between D11S860 and D11S454), unaffected individual VI-14 (between D11S1454 and D11S1318), and affected individual VI-16 (between D11S860 and D11S454). These data indicate that LQT1 is located between D11S922 and D11S454. Together with recent studies placing LQT1 centromeric of TH (Russell et al., 1995), these data place LQT1 in the interval between TH and D11S454.

TABLE 2

Pairwise LOD Scores Between LQT1 and 11p15.5 Markers

| | Recombination Fraction (θ) | | | | | | | |
|---|---|---|---|---|---|---|---|---|
| | 0.0 | 0.001 | 0.01 | 0.05 | 0.1 | 0.2 | $Z_{max}$* | $θ_{max}$† |
| HRAS | 9.67 | 9.94 | 10.50 | 10.38 | 9.62 | 7.57 | 10.59 | 0.021 |
| D11S922 | 10.05 | 13.05 | 13.85 | 13.59 | 12.59 | 10.01 | 13.92 | 0.019 |
| TH | 11.01 | 10.99 | 10.82 | 10.06 | 9.07 | 6.96 | 11.01 | 0.0 |
| D11S1318 | 10.30 | 10.29 | 10.13 | 9.40 | 8.47 | 6.50 | 10.30 | 0.0 |
| KVLQT1 | 14.19 | 14.17 | 13.94 | 12.89 | 11.54 | 8.68 | 14.19 | 0.0 |
| D11S454 | 11.06 | 11.05 | 10.89 | 10.16 | 9.17 | 7.01 | 11.06 | 0.0 |
| D11S860 | 5.77 | 6.92 | 8.32 | 9.14 | 8.92 | 7.46 | 9.15 | 0.058 |
| D11S12 | 1.50 | 2.26 | 3.12 | 3.46 | 3.27 | 2.49 | 3.46 | 0.047 |

LOD scores were computed with the assumption of 90% penetrance and gene frequency of 0.001 (Lathrop et al. 1985).
*$Z_{max}$ indicates maximum LOD score.
†$θ_{max}$ indicates estimated recombination fraction at $Z_{max}$.

The size of the region containing LQT1 was estimated using pulsed-field gel analyses with genomic probes from chromosome 11P15.5. Probes from TH, D11S551 and D11S454 hybridized to a 700 kb Mlu I restriction fragment (FIG. 2). These data suggested that the region containing LQT1 is less than 700 kb. Physical representation of this region was achieved by screening yeast artificial chromosome (YAC) and P1 libraries with probes from the region (Tanigami et al., 1992; Tokino et al., 1991). The order of these clones was confirmed using fluorescent in situ hybridization (FISH) analyses as: telomere-TH-D11S551-D11S679-D11S601-D11S454-centromere. The clones identified in initial experiments were then used for identification of adjacent overlapping clones. The minimum set of clones from the LQT1 interval is shown in FIG. 2.

EXAMPLE 8

Identification and Characterization of KVLQT1

Exon amplification with clones from the physical map was performed to identify candidate genes for LQT1. Exon trapping was performed using pSPL3B (Burn et al., 1995) on genomic P1 clones as previously described (Buckler et al., 1991; Church et al. 1994). A minimum of 128 trapped exons from each P1 clone were initially characterized by sizing the PCR products. From these, 400 clones were further analyzed by dideoxy sequencing using an A.L.F. automated sequencer (Pharmacia). DNA sequence and database analyses revealed eight possible exons with predicted amino acid sequence similarity to ion channels. The highest similarity was obtained for a 238 base pair trapped exon (4181A) with 53% similarity to potassium channel proteins from multiple species, including similarity to a portion of a putative pore region PCR analyses were used to map 4181A to the short arm of chromosome 11 and to two P1s from the physical map (118A10, 18B12). These data suggested that 4181A was part of a potassium channel gene on chromosome 11p15.5.

Two different cDNA library screening methods were used to determine if trapped exon 4181A was part of a gene. Traditional plaque filter hybridization with an adult human cardiac cDNA library led to the identification of a single positive clone. A variation of cDNA selection was used to screen a second cardiac cDNA library (the GENETRAPPER™ cDNA Positive Selection System, Life Technologies, Inc.), and twelve independent clones were recovered. DNA sequence analyses revealed complete alignment with sequences derived from 4181A and the other trapped exons described above. The longest open reading frame spanned 1654 base pairs. Two consensus polyadenylation signals were identified upstream of the poly(A) tail in the 3' untranslated region. The complete cDNA was not obtained at this stage of the study The partial cDNA predicted a protein with structural characteristics of potassium channels. Hydropathy analyses suggested a topology of six major hydrophobic regions that may represent membrane-spanning α-helices. These regions share sequence similarity with potassium channel transmembrane domains S1–S6. A comparison of the predicted amino acid sequence derived from the identified gene and the Shaker (SHA) potassium channel (Pongs et al., 1988) is shown in FIG. 3. In the region containing S1–S6, the amino acid sequence identity was 30% and similarity was 59%. The sequence located 3' of S1–S6 did not have significant similarity to any known protein. Because this gene has high similarity to voltage-gated potassium channel genes and became a strong candidate for LQT1, it was named KVLQT1.

Northern blot analyses were used to determine the tissue distribution of KVLQT1 mRNA. KVLQT1 cDNA probes detected a 3.2 kb transcript in human pancreas, heart, kidney, lung, and placenta, but not in skeletal muscle, liver, or brain (FIG. 4). The heart showed highest levels of KVLQT1 mRNA. The Northern analyses were performed using a multiple tissue Northern filter (Human MTN blot 1, Clontech) as described by Curran et al., 1995

EXAMPLE 9

Characterization of the Complete KVLQT1 cDNA

The studies described above resulted in the cloning and characterization of an incomplete cDNA for KVLQT1. The sequence of this incomplete cDNA predicted a protein with six hydrophobic membrane-spanning α-helices (S1–S6) and a typical $K^+$ channel pore signature sequence (Heginbotham et al., 1994). However, this cDNA appeared to be missing the amino terminal domain and did not functionally express. To define the complete sequence of KVLQT1, several cDNA libraries were screened and a new clone was isolated. A cDNA probe containing exons 3 through 6 was used to isolate three full length KVLQT1 cDNA clones from an adult heart cDNA library prepared in the laboratory using SuperScript Choice system (GIBCO BRL). The complete cDNA sequence and the encoded protein are shown in FIG. 5A–5B.

EXAMPLE 10

Genomic Structure of KVLQT1

The genomic DNA of KVLQT1 was examined and the exon/intron boundaries determined for all exons.
A. Isolation of cDNA Clones A cDNA probe containing exons 3 through 6 was used to isolate three full length KVLQT1 cDNA clones from an adult heart cDNA library prepared in the laboratory using SuperScript Choice system (GIBCO BRL).
B. Isolation of Genomic Clones KVLQT1 P1 clones were isolated as described (Wang et al., 1996). The cosmid containing exon 1 was isolated screening a human genomic cosmid library (Stratagene) with a cDNA probe from exon 1.
C. Exon/Intron Boundary Determination All genomic clones were sequenced using primers designed to the cDNA sequences. The KVLQT1 P1 clones were cycle sequenced using ThermoSequenase (Amersham Life Science). The KVLQT1 cosmids were sequenced by the dideoxy chain termination method on an Applied Biosystems model 373A DNA sequencer. The exact exon/intron boundaries were determined by comparison of cDNA, genomic sequences, and known splice site consensus sequences.

D. Design of PCR Primers and PCR Reaction Conditions

Primers to amplify exons of the two genes were designed empirically or using OLIGO 4.0 (NBI). Amplification conditions were:

(1) 94° C. for 3 minutes followed by 30 cycles of 94° C. for 10 seconds, 58° C. for 20 seconds and 72° C. for 20 seconds and a 5 minute extension at 72° C.

(2) same as conditions in (1) except that the reactions had final concentrations of 10% glycerol and 4% formamide and were overlaid with mineral oil.

(3) 94° C. for 3 minutes followed by 5 cycles of 94° C. for 10 seconds, 64° C. for 20 seconds and 72° C. for 20 seconds and 30 cycles of 94° C. for 10 seconds, 62° C. for 20 seconds and 72° C. for 20 seconds and a 5 minute extension at 72° C.

E. KVLQT1 Genomic Structure and Primer Sets

Full length cDNA clones were isolated from an adult heart cDNA library. A 5'-cDNA probe generated from one of these clones was used to isolate cos1, a genomic cosmid clone containing exon 1. P1 genomic clones encompassing the rest of the KVLQT1 cDNA were previously isolated (Wang et al., 1996). These genomic clones span approximately 400 kb on chromosome 11p15.5 (FIG. 6). To determine the exon structure and exon/intron boundaries, cos1 and P1 clones 118A10, 112E3, 46F10 and 49E5 were sequenced using primers designed to the cDNA. Comparison of the genomic and cDNA sequences of KVLQT1 revealed the presence of 16 exons (FIGS. 5A–5B and Table 3). Exon size ranged from 47 bp (exon 14) to 1122 bp (exon 16). All intronic sequences contained the invariant GT and AG at the donor and acceptor splice sites, respectively (Table 3). One pair of PCR primers was designed for each of intron sequences flanking, exons 2 through 16 and two pairs of primers with overlapping products were designed for exon 1 due to its large size (Table 4). These primers can be used to screen all KVLQT1 exons.

EXAMPLE 11

Characterization of KVLQT1 Function

To define the function of KVLQT1, Chinese hamster ovary (CHO) cells were transfected with the complete cDNA described above in Example 9. The KVLQT1 cDNA was subcloned into pCEP4 (In Vitrogen). CHO cells were cultured in Ham's F-12 medium and transiently transfected using Lipofectaminie (Gibco BRL). Cells were transfected for 18 hours in 35 mm dishes containing 6 µL lipofectamine, 0.5 µg green fluorescent protein (pGreen Lantern-1, Gibco BRL), and 1.5 µg of KVLQT1 in pCEP4. Fluorescent cells were voltage-clamped using an Axopatch 200 patch clamp amplifier (Axon Instruments) 48 to 78 hours after transfection. The bathing solution contained, in mM: 142 NaCl, 2 KCl, 1.2 $MgCl_2$, 1.8 $CaCl_2$, 11.1 glucose, 5.5 HEPES buffer (pH 7.4, 22–25° C.). The pipette solution contained, in mM: 110 potassium glutamate, 20 KCl, 1.0 $MgCl_2$, 5 EGTA, 5 $K_2ATP$, 10 HEPES (pH 7.3). Data acquisition and analyses were done using pCLAMP6 (Axon Instruments). The voltage dependence of current activation was determined by fitting the relationship between tail currents (determined by extrapolation of deactivating phase of current to the end of the test pulse) and test potential with a Boltzmann function. Tail currents were normalized relative to the largest value for each oocyte.

TABLE 3

Intron/Exon Boundaries in KVLQT1

| Exon No. | intron/EXON[a] | EXON (total bases) | EXON/intron[a] |
|---|---|---|---|
| 1 | 5'UTR...ATGGCCGCGG (9) | 386+ | ACTTCGCCGTgtgagtatcg (10) |
| 2 | tgtcttgcagCTTCCTCATC (11) | 91 | CTTCTGGATGgtacgtagca (12) |
| 3 | gtccctgcagGAGATCGTGC (13) | 127 | TCCATCATCGgtgagtcatg (14) |
| 4 | cactccacagACCTCATCGT (15) | 79 | GGGCCATCAGgtgcgtctgt (16) |
| 5 | tccttcgcagGGGCATCCGC (17) | 97 | CCACCGCCAGgtgggtggcc (18) |
| 6 | tctggcctagGAGCTGATAA (19) | 141 | GTGGGGGGTGgtaagtcgga (20) |
| 7 | ctccctgcagGTCACAGTCA (21) | 111 | GCTCCCAGCGgtaggtgccc (22) |
| 8 | tccttcccagGGGATTCTTG (23) | 96 | ACTCATTCAGgtgcggtgcc (24) |
| 9 | cccacctcagACCGCATGGA (25) | 123 | GTCTGTGGTGgtgagtagcc (26) |
| 10 | ttttttttagGTAAAGAAAA (27) | 142 | GACAGTTCTGgtgagaaccc (28) |
| 11 | ttctcctcagTAAGGAAGAG (29) | 121 | ACATCTCACAgtgagtgcct (30) |
| 12 | tccactgcagGCTGCGGGAA (31) | 76 | GAAATTCCAGgtaagccctg (32) |
| 13 | tgtcccgcagCAAGCGCGGA (33) | 95 | TGCAGAGGAGgtgggcacgg (34) |
| 14 | ttctctccagGCTGGACCAG (35) | 47 | TCCGTCTCAGgtgggttct (36) |
| 15 | tcccccatagAAAAGAGCAA (37) | 62 | AGAAGACAAGgtaggctcac (38) |
| 16 | gtcccgcagGTGACGCAGC (39) | 237+ | GGGGTCCTGA...3'UTR (40) |

[a] SEQ ID NO is shown in parentheses following each sequence.

TABLE 4

Primers Used to Amplify KVLQT1 Exons

| Exon No. | Forward Primer[a] | Reverse Primer[a] | Size | C[b] |
|---|---|---|---|---|
| 1 | CTCGCCTTCGCTGCAGCTC (41) | GCGCGGGTCTAGGCTCACC (42) | 334 | 2 |
| 1 | CGCCGCGCCCCAGTTGC (43) | CAGAGCTCCCCCACACCAG (44) | 224 | 2 |
| 2 | ATGGGCAGAGGCCGTGATGCTGAC (45) | ATCCAGCCATGCCCTCAGATGC (46) | 165 | 3 |
| 3 | GTTCAAACAGGTTGCAGGGTCTGA (47) | CTTCCTGGTCTGGAAACCTGG (48) | 256 | 3 |
| 4 | CTCTTCCCTGGGGCCCTGGC (49) | TGCGGGGAGCTTGTGGCACAG (50) | 170 | 3 |
| 5 | TCAGCCCCACACCATCTCCTTC (51) | CTGGGCCCCTACCCTAACCC (52) | 154 | 3 |
| 6 | TCCTGGAGCCCGACACTGTGT (53) | TGTCCTGCCCACTCCTCAGCCT (54) | 238 | 2 |
| 7 | TGGCTGACCACTGTCCCTCT (55) | CCCCAGGACCCCAGCTGTCCAA (56) | 195 | 3 |
| 8 | GCTGGCAGTGGCCTGTGTGGA (57) | AACAGTGACCAAAATGACAGTGAC (58) | 191 | 3 |
| 9 | TGGCTCAGCAGGTGACAGC (59) | TGGTGGCAGGTGGGCTACT (60) | 185 | 1 |
| 10 | GCCTGGCAGACGATGTCCA (61) | CAACTGCCTGAGGGGTTCT (62) | 216 | 1 |
| 11 | CTGTCCCCACACTTTCTCCT (63) | TGAGCTCCAGTCCCCTCCAG (64) | 195 | 1 |
| 12 | TGGCCACTCACAATCTCCT (65) | GCCTTGACACCCTCCACTA (66) | 222 | 1 |
| 13 | GGCACAGGGAGGAGAAGTG (67) | CGGCACCGCTGATCATGCA (68) | 216 | 1 |

TABLE 4-continued

Primers Used to Amplify KVLQT1 Exons

| Exon No. | Forward Primer[a] | Reverse Primer[a] | Size | C[b] |
|---|---|---|---|---|
| 14 | CCAGGGCCAGGTGTGACTG (69) | TGGGCCCAGAGTAACTGACA (70) | 119 | 2 |
| 15 | GGCCCTGATTTGGGTGTTTTA (71) | GGACGCTAACCAGAACCAC (72) | 135 | 2 |
| 16 | CACCACTGACTCTCTCGTCT (73) | CCATCCCCAGCCCCATC (74) | 297 | 2 |

[a]SEQ ID NO is shown in parentheses following each sequence.
[b]Conditions of the PCR as described in Example 10D.

A voltage-dependent, outward K$^+$ current was observed after membrane depolarization to potentials above −60 mV (FIG. 7A). This current reached a steady state within 1 second at +40 mV. Activation of the current was preceded by a brief delay, and repolarization to −70 mV elicited a tail current with an initial increase in amplitude (a hook) before deactivation. Similar tail current hooks where previously observed for HERG K$^+$ channels, and were attributed to recovery of channels from inactivation at a rate easter than deactivation (Sanguinetti et al., 1995; Smith et al., 1996: Spector et al., 1996). The activation curve for KVLQT1 current was half-maximal ($V_{1/2}$) at −11.6±0.6 mV, and had a slope factor of 12.6±0.5 mV (n=6; FIG. 7B).

The biophysical properties of KVLQT1 were unlike other known cardiac K$^+$ currents. It was hypothesized that KVLQT1 might coassemble with another subunit to form a known cardiac channel. The slowly activating delayed rectifier K$^+$ current, $I_{Ks}$, modulates repolarization of cardiac action potentials. Despite intensive study, the molecular structure of the $I_{Ks}$ channel is not understood. Physiological data suggest that one component of the $I_{Ks}$ channel is minK (Goldstein and Miller, 1991; Hausdorff et al., 1991; Takumi et al., 1991; Busch et al., 1992; Wang and Goldstein, 1995; Wang et al., 1996), a 130 amino acid protein with a single putative transmembrane domain (Takumi et al., 1988). The size and structure of this protein, however, have led to doubt that minK alone forms functional channels (Attali et al., 1993; Lesage et al., 1993).

To test this hypothesis, CHO cells where cotransfected with KVLQT1 and human KCNE1 cDNAs. A KCNe1 cDNA was subcloned in pCEP4 (In Vitrogen) and transfection was performed as described above for KVLQT1 alone. For the cotransfection of KVLQT1 and KCNE1, 0.75 µg of each cDNA was used. As reported previously (Lesage et al., 1993), transfection of CHO cells with KCNE1 alone did not induce detectable current (n=10, FIG. 7C). Cotransfection of KCNE1 with KVLQT1 induced a slowly activating delayed-rectifier current that was much larger than the current in cells transfected with KVLQT1 alone (FIGS. 7D and 7E). The slow activation of current in cotransfected CHO cells was preceded by a delay that lasted several hundred msec, indicating that no significant homomeric KVLQT1 channel current was present. Current did not saturate during long depolarizing pulses, and required a three-exponential function to best describe the initial delay and two phases of current activation. During a 30 sec depolarizing pulse to +40 mV, current was activated with time constants of 0.68±0.18, 1.48±0.16. and 8.0±0.6 sec (n=4). The isochronal (7.5 sec) activation curve for current had a $V_{1/2}$ of 7.5±0.9 mV, and a slope factor of 16.5±0.8 mV (n=7; FIG. 9B). By comparison, the $V_{1/2}$ and slope of the activation curve for human cardiac $I_{Ks}$ are 9.4 mV and 11.8 mV (Li et al., 1996).

Like KVLQT1 and hminK coexpressed in CHO cells, activation of cardiac $I_{Ks}$ is extremely slow and was best described by a three-exponential function (Balser et al., 1990; Sanguinetti and Jurkiewicz, 1990). Quinidine (50 µM) blocked tail currents in cotransfected CHO cells by 30±8% (n=5), similar to its effect (40–50% block) on $I_{Ks}$ in isolated myocytes (Balser et al, 1991). Thus, coexpression of KVLQT1 and hminK in CHO cells induced a K$^+$ current with biophysical properties nearly identical to cardiac $I_{Ks}$.

To characterize the properties of hminK and KVLQT1 further, these channels were expressed separately and together in Xenopus oocytes. Xenopus laevis oocytes were isolated and injected with cRNA as described by Sanguinetti et al. (1995). KVLQT1 cDNA was subcloned into pSP64 (Promega). KCNE1 cDNA was a gift from R. Swanson. Roughly equimolar concentrations of KVLQT1 cRNA (5.8 ng per oocyte) and KCNE1 (1 ng per oocyte) cRNA were used for the co-injection experiments. The bathing solution contained, in mM: 98 NaCl, 2 KCl, 2 MgCl$_2$, 0.1 CaCl$_2$, and 5 HEPES (pH 7.6, 22–25° C.). For reversal-potential experiments, osmolarity was maintained by equimolar substitution of external NaCl for KCl. Currents were recorded using standard two-microelectrode voltage clamp techniques 3 days after injection of oocytes with cRNA (Sanguinetti et al., 1995). Currents were filtered at 0.5 kHz and digitized at 2 kHz. Data are presented as mean±s.e.m.

Oocytes injected with KVLQT1 complementary RNA expressed a rapidly activating outward K$^{31}$ current with a voltage dependence of activation nearly identical to CHO cells transfected with KVLQT1 cDNA (FIGS. 8A and 8B). The K$^+$ selectivity of KVLQT1 channels was determined by measuring the reversal potential ($E_{rev}$) of tail currents in different concentrations of extracellular K ($[K^+]_e$). The slope of the relationship between $E_{rev}$ and $\log[K^+]_e$ was 49.9±0.4 mV (n=7; FIG. 8C), significantly less than predicted by the Nernst equation (58 mV) for a perfectly selective K$^+$ channel. Co-injection of oocytes with KVLQT1 and KCNE1 cRNA induced a current similar to I$^{Ks}$ (FIG. 9C). The slope of the relationship between $E_{rev}$ and $\log[K^+]_e$, for co-injected oocytes was 49.9±4 mV (n=6), similar to KVLQT1 alone and to guinea pig cardiac I$^{Ks}$ (49 mV) (Matsuura et al., 1987). The isochronal (7.5 sec) activation curve for co-injected oocytes had a $V_{1/2}$ of 6.2 mV and a slope of 12.3 mV (FIG. 9E), similar to cardiac $I_{Ks}$.

EXAMPLE 12

Identification of a KVLQT1 Gene in Xenopus

By contrast with CHO cells, KCNE1 was able to undergo functional expression in Xenopus oocytes (FIG. 9B). The induced current ($I_{sK}$) was smaller than the current induced in co-injected oocytes, but the kinetics and voltage dependence of activation were similar (FIGS. 9A–E). Two observations have led to the hypothesis that $I_{sK}$ in Xenopus oocytes results from channels formed by coassembly of minK with an unidentified, constitutively expressed subunit. First, the magnitude of $I_{sK}$ saturates after injection of very small amounts of KCNE1 cRNA (FIG. 9D), suggesting that an endogenous component of limited quantity is required for functional expression (Wang and Goldstein, 1995; Cui et al., 1994). Second, heterologous expression of minK in mammalian cells does not induce detectable current (Lesage et al., 1993) (FIG. 7C). suggesting that minK is not sufficient to form functional channels. It was hypothesized that this unidentified subunit might be a homologue of KVLQT1. To test this hypothesis, a Xenopus oocyte cDNA library (Clontech) was screened with a KVLQT1 cDNA clone spanning the S3–S5 domains. A 1.6 kb partial clone (XKVLQT1, FIG. 10A) was isolated. XKVLQT1 is 88% identical at the amino acid level with the corresponding region of KVLQT1. (FIG. 10A). These data suggest that $I_{sK}$ results from the coassembly of the XKVLQT1 and minK proteins.

It was concluded that KVLQT1 and hminK coassemble to form the cardiac $I_{Ks}$ channel. Two delayed-rectifier K$^+$ currents, $I_{Kr}$ and $I_{Ks}$ modulate action-potential duration in cardiac myocytes (Li et al., 1996; Sanguinetti and Jurkiewicz, 1990). Previous studies have implicated dysfunction of $I_{Kr}$ channels in long QT syndrome (Sanguinetti et al., 1995; Curran et al., 1995; Sanguinetti et al., 1996a). The observation that KVLQT1 mutations also cause this disorder (Wang et al., 1996), and the discovery that KVLQT1 forms part of the $I_{Ks}$ channel, indicate that dysfunction of both cardiac delayed-rectifier K$^+$ channels contribute to risk of sudden death from cardiac arrhythmia.

EXAMPLE 13

Cosegregation of KVLQT1 Missense Mutations with LQT in Six Large Families

To test the hypothesis that KVLQT1 is LQT1, single-strand conformational polymorphism (SSCP) analyses where used to screen for functional mutations in affected members of K1532, the largest LQT family that showed linkage to chromosome 11. SSCP was carried out as previously described (Wang et al., 1995a, Wang et al., 1995b). Normal and aberrant SSCP products were isolated and sequenced directly as described (Wang and Keating, 1994) or subcloned into pBluescript (SK$^+$) (Stratagene) using the T-vector method (Marchuk et al., 1991). When the latter method was used, several clones were sequenced by the dideoxy chain termination method using Sequenase™ Version 2.0 (United States Biochemicals, Inc.). Analyses were focused on the region between S2 and S6 since these regions might be important for KVLQT1 function. We designed oligonucleotide primers based on cDNA sequences and used these primers for cycle sequencing reactions with the KVLQT1-containing, P1, 18B12 (Wang and Keating, 1994). These experiments defined intronic sequences flanking exons encoding S2–S6. Additional primers were then generated from these intronic sequences and used for SSCP analyses (Table 5).

SSCP analyses identified an anomalous conformer in the 70 affected members of K1532 (FIG. 11A). This aberrant conformer was not observed in the 147 unaffected members of this kindred or in genomic DNA from more than 200 unrelated control individuals. The two-point LOD score for linkage between this anomaly and LQT was 14.19 at a recombination fraction of 0(Table 2). No recombination was observed between KVLQT1 and LQT1, indicating that these loci are completely linked. DNA sequence analyses of the normal and aberrant SSCP conformers revealed a single base substitution, a G to A transition, at the first nucleotide of codon Val-125 (FIG. 11A and Table 6). This mutation results in a valine to methionine substitution in the predicted intracellular domain between S4 and S5.

To further test the hypothesis that mutations in KVQT1 cause LQT, DNA samples from affected members of five additional large LQT kindreds were studied. Linkage analyses with polymorphic markers from this region had shown that the disease phenotype was linked to chromosome 11 in these families. Aberrant SSCP conformers were identified in affected members of K2605, K1723, K1807 (FIGS. 11B–D), K161 and K162. The SSCP anomalies identified in K161 and K162 were identical to that observed in K1807. The aberrant SSCP conformer was not seen in unaffected members of these kindreds or in DNA samples from more than 200 unrelated control individuals. The normal and aberrant conformers identified in each family were sequenced. The nucleotide changer coding effect, and location of each mutation are summarized in Table 6.

TABLE 5

PCR Primers Used to Define KVLQT1 Mutations

| Primer | Sequence | Region Amplified | SEQ ID NO: |
|---|---|---|---|
| 1 | GAGATCGTGCTGGTGGTGTTCT | S2–S3 | 75 |
| 2 | CTTCCTGGTCTGGAAACCTGG | | 76 |
| 3 | CTCTTCCCTGGGGCCCTGGC | S3–S4 | 77 |
| 4 | TGCGGGGGAGCTTGTGGCACAG | | 78 |
| 5 | GGGCATCCGCTTCCTGCAGA | S4 | 79 |
| 6 | CTGGGCCCCTACCCTAACCC | | 80 |
| 7 | TCCTGGAGCCCGAACTGTGTGT | S5-Pore | 81 |
| 8 | TGTCCTGCCCACTCCTCAGCCT | | 82 |
| 9 | CCCCAGGACCCCAGCTGTCCAA | Pore-S6 | 83 |
| 10 | AGGCTGACCACTGTCCCTCT | | 84 |
| 11 | GCTGGCAGTGGCCTGTGTGGA | S6 | 85 |
| 12 | AACAGTGACCAAAATGACAGTGAC | | 86 |

TABLE 6

Summary of KVLQT1 Mutations

| Codon | Nucleotide change | Coding effect | Mutation | Region | Kindred | No. of affected |
|---|---|---|---|---|---|---|
| 167–168 | ΔTCG | Deletion | F167W/ G168Δ | S2 | K13216 | 1 |
| 178 | GCC to CCC | Missense | A178P | S2–S3 | K13119 | 1 |
| 189 | GGG to AGG | Missense | G189R | S2–S3 | K2557 | 3 |
| 190 | CGG to CAG | Missense | R190Q | S2–S3 | K15019 | 2 |
| 254 | GTG to ATG | Missense | V254M | S4–S5 | K1532 | 70 |
| 273 | CTC to TTC | Missense | L273F | S5 | K1777 | 2 |
| 306 | GGG to AGG | Missense | G306R | Pore | K20926 | 1 |
| 312 | ACC to ATC | Missense | T3121 | Pore | K20925 | 1 |
| 341 | GCG to GAG | Missense | A341E | S6 | K1723 | 6 |
| 341 | GCG to GAG | Missense | A341E | S6 | K2050 | 2 |
| 341 | GCG to GTG | Missense | A341V | S6 | K1807 | 6 |
| 341 | GCG to GTG | Missense | A341V | S6 | K161 | 18 |
| 341 | GCG to GTG | Missense | A341V | S6 | K162 | 18 |
| 341 | GCG to GTG | Missense | A341V | S6 | K163 | 3 |
| 341 | GCG to GTG | Missense | A341V | S6 | K164 | 2 |
| 345 | GGG to GAG | Missense | G345E | S6 | K2605 | 11 |
| 168 | GGG to AGG | Missense | G168R | S2 | K2625 | — |
| 168 | GGG to AGG | Missense | G168R | S2 | K2673 | — |
| 168 | GGG to AGG | Missense | G168R | S2 | K3698 | — |
| 314 | GGC to AGC | Missense | G314S | Pore | K19187 | — |
| 315 | TAT to TGT | Missense | Y315C | Pore | K22709 | — |
| 318 | AAG to AAC | Missense | K318N | Pore | K2762 | — |
| 353 | CTG to CCG | Missense | L353P | S6 | K340 | — |
| 366 | CGG to TGG | Missense | R366W | C-terminus | K2824 | — |

EXAMPLE 14

A KVLQT1 Intragenic Deletion and Fifteen Missense Mutations Associated with LQT in Small Families and Sporadic Cases To identify additional LQT-associated mutations in KVLQT1, further SSCP analyses were performed for small kindreds and sporadic cases. SSCP revealed an aberrant conformer in kindred 13216 (FIG. 12A). Analyses of more than 200 unrelated control individuals failed to show this anomaly. This aberrant conformer was cloned and sequenced, revealing a three base pair deletion encompassing codons 38 and 39. This mutation results in a phenylalanine to tryptophan substitution and deletion of a glycine in the putative S2 domain (Table 6).

Aberrant SSCP conformers were identified in affected members of additional kindreds. An aberrant SSCP conformer identified in K2050 was identical to that in K1723, and aberrant conformers identified in K161, K162, K163 and K164 were identical to that observed in K1807. Also kindreds 2625, 2673 and 3698 had the identical mutation. None of the aberrant conformers was identified in DNA samples from more than 200 control individuals. In each case, the normal and aberrant conformers were sequenced. These data are shown in FIG. 12A–O and summarized in Table 6. In total, KVLQT1 mutations associated with LQT in 24 families or sporadic cases were identified. providing strong molecular genetic evidence that mutations in KVLQT1 cause the chromosome 11-linked form of LQT.

EXAMPLE 15

KCNE1 Variations which Result in LQT

Separate studies on different individuals were performed in finding variants of minK. These studies were performed using the following methods.

A. Phenotypic Analyses

Individuals were phenotypically characterized based on the QT interval corrected for heart rate. Individuals were characterized as affected if QTc≧0.46 second. Individuals were assigned as unaffected if QTc≦0.42 second. Informed consent was obtained from all individuals or their guardians in accordance with local institutional review board guidelines. Phenotypic data were interpreted without knowledge of genotype.

B. Mutation Analyses

Genomic samples were amplified by PCR using the following primer pairs:

MINK1F-5'-CTGCAGCAGTGGAACCTTAATG-3' (SEQ ID NO:87) and
MINK1R-5'-GTTCGAGTGCTCCAGCTTCTTG-3' (SEQ ID NO:88);
MINK2F-5'-AGGGCATCATGCTGAGCTACAT--3' (SEQ ID NO:89) and
MINK2R-5'-TTTAGCCAGTGGTGGGGTTCA-3' (SEQ ID NO:90);
MINK3F-5'-GTTCAGCAGGGTGGCAACAT-3' (SEQ ID NO:91) and
MINK3R-5'-GCCAGATGGTTTTCAACGACA-3' (SEQ ID NO:92).

PCR products were used in SSCP analysis as described (K W Wang et al. 1996). PCR was completed with 75 ng DNA in a volume of 10 μL using a Perkin-Elmer Cetus 9600 thermocycler. Amplification conditions were 94° C. for 3 minutes followed by 30 cycles of 94° C. for 10 seconds. 58° C. for 20 seconds, 72° C. for 20 seconds and a 5 minute extension at 72° C. Reactions were diluted with 40 μL of 0.1% SDS/10 mM EDTA and with 30 μL of 95% formamide load dye. The mixture was denatured at 94° C. for 5 minutes and placed on ice. Three microliters of each sample were separated on 5% and 10% non-denaturing polyacrylamide gels (acrylamide:bisacrylamide 49:1) at 4° C. and on 0.5× and 1× MDE (mutation detection enhancement) gels (FMC BioProdutcts) at room temperature. Electrophoreses on the 5% and 10% gels were completed at 40 W for 3–5 hours;

electrophoreses on 0.5× and 1×MDE gels were completed overnight, respectively, at 350 V and 600 V. Gels were dried on 3 MM filter paper and exposed to film for 18 hours at −70° C.

SSCP bands were cut out of the gel and eluted in 100μL double distilled water at 65° C. for 30 minutes. Ten microliters of eluted DNA was reamplified using the original printer pair. Products were separated on 1% low melting temperature agarose gels (FMC) phenol-chloroform extracted and ethanol precipitated. DNA was sequenced in both directions by the dideoxy chain termination method on an Applied Biosystems model 373A DNA sequencer.

C. Functional Expression

KCNE1 cDNA expression constructs were amplified by PCR from total human DNA and cloned in pSP64 transcription vector (Promega) using, the following primers:

MINKF-5'-CAGTGGAAGCTTAATGCCCAGGATGATC-3' (SEG ID NO:93) and
MINKR-5'-CAGGAGGATCCAGTTTAGCCAGT GGTGGGGGTTCA-3' (SEQ ID NO:94).

Nucleotides in bold denote the changes made to create Hind III and BamH I restriction sites (underlined). A full-length KVLQT1 cDNA clone (identical to that reported by Yang et al., (1997)) was isolated from a human cardiac cDNA library and subcloned into the pSP64 plasmid expression vector. All constructs were confirmed by DNA sequence analyses. Complementary RNAs were synthesized using the mCAP RNA capping kit (Stratagene).

Isolation of *Xenopus laevis* oocytes and cRNA injection were performed as described (Sanguinetti et al., 1995). Voltage clamp data were acquired and analyzed using PCLAMP v6.0 software (Axon Instruments). Isochronal (7.5 seconds) rather than steady state measurements were used to estimate the voltage dependence of $I_{Ks}$ activation. The voltage-dependence of $I_{Ks}$ activation was determined by fitting peak tail currents to a Boltzmann function. $V_{1/2}$, the voltage at which the current was half-activated using this pulse protocol, and the slope factor, were calculated from these data. Activating current was fitted to a biexponential function to obtain slow and fast time constants of activation. Deactivation time constants were obtained by fitting decaying tail currents at various test potentials to a single exponential function.

All data are mean ±S.E.M. Statistical analyses were performed using repeated measures analysis of variance, with the Fisher's Least Significance post hoc test and the unpaired Student's T-test. A p value <0.05 was considered statistically significant.

D. Results

Ion channel β subunits are ancillary proteins that coassemble with α subunits to modulate the gating kinetics and enhance stability of multimeric channel complexes (Rettig et al., 1994; Shi et al., 1996). Despite their functional importance, dysfunction of potassium β subunits has not been associated with disease. Recent physiologic studies suggest that KCNE1 encodes β subunits that coassemble with KvLQT1 α subunits to form the slowly activating delayed rectifier K⁺ ($I_{Ks}$) channel (Sanguinetti et al., 1996b; Barhanin et al., 1996). Because KVLQT1 mutations cause arrhythmia susceptibility in the long QT syndrome (LQT) (Q. Wang et al., 1996; Neyroud et al., 1997; Splawski et al., 1997a), we hypothesized that mutations in KCNE1 also cause this disorder. Here KCNE1 missense mutations are defined in affected members of two LQT families. Both mutations (S74L, D76N) reduced $I_{Ks}$ by shifting the voltage dependence of activation and accelerating channel deactivation. D76N hminK also had a dominant negative effect. The functional consequences of these mutations would be delayed cardiac repolarization and an increased risk of arrhythmia. These data establish KCNE1 as an LQT gene and confirm that hminK is an integral protein of the $I_{Ks}$ channel.

Individuals with LQT have been ascertained and phenotypically characterized (Keating et al., 1991a: Jiang et al., 1994). Single strand conformation polymorphism (SSCP) analyses using primers that span KCNE1 led to the identification of an anomalous conformer in affected members of kindred 1789 (FIG. 13A). This conformer was not observed in unaffected family members or in 200 unrelated control individuals (400 chromosomes). DNA sequence analysis revealed a G to A transition at the first nucleotide of codon 76, causing an Asp to Asn substitution (D76N) (FIG. 13C). The sequences for KCNE1 cDNA and its protein product are listed here as SEQ ID NO:3 and SEQ ID NO:4, respectively. The first nucleotide of codon 76 is base 418 of SEQ ID NO:3.

Further SSCP analyses defined a second anomaly that cosegregated with the disease in kindred 1754 (FIG. 13B). This anomaly was not observed in unaffected members of the family or in 200 controls. DNA sequence analysis revealed a C to T transition in the second nucleotide of codon 74 (base 413 of SEQ ID NO:3), leading to substitution of Ser to Leu (S74L) (FIG. 13C). Analyses of further DNA samples obtained from unrelated individuals with LQT revealed additional KCNE1 mutations. Table 7 lists the KCNE1 mutations found in LQT families.

TABLE 7

Summary of KCNE1 Mutations

| Codon | Nucleotide change | Coding effect | Mutation | Kindred |
|---|---|---|---|---|
| 28 | TCG to TTG | Missense | S28L | 1789 |
| 32 | CGC to CAC | Missense | R32H | 2521 |
| 74 | TCG to TTG | Missense | S74L | 1754 |
| 76 | GAC to AAC | Missense | D76N | 1789 |
| 98 | CGG to TGG | Missense | R98W | 2016 |
| 127 | CCT to GCT | Missense | P127A | 2016 |
| 127 | CCT to ACT | Missense | P127T | 2819 |

To determine the functional consequences of these KCNE1 mutations, we expressed mutant and wild-type (WT) proteins in Xenopus oocytes. Because the stoichiometry of KVLQT1 and minK interaction is not known, varying amounts of KCNE1 cRNA (0.01–2.5 ng/oocyte) were coinjected with a fixed quantity of KVLQT1 cRNA (6 ng/oocyte) and the resultant currents recorded. $I_{Ks}$ amplitude increased as a function of injected KCNE1, and saturated at KCNE1 cRNA levels ≧0.6 ng/oocyte (FIGS. 14A–14B). Subsequent coexpression experiments were performed using 1.2 ng/oocyte KCNE1 and 6 ng/oocyte KVLQT1 cRNA, to insure that KCNE1 was not a limiting factor for expression of heteromultimeric channels.

Figure 15A:
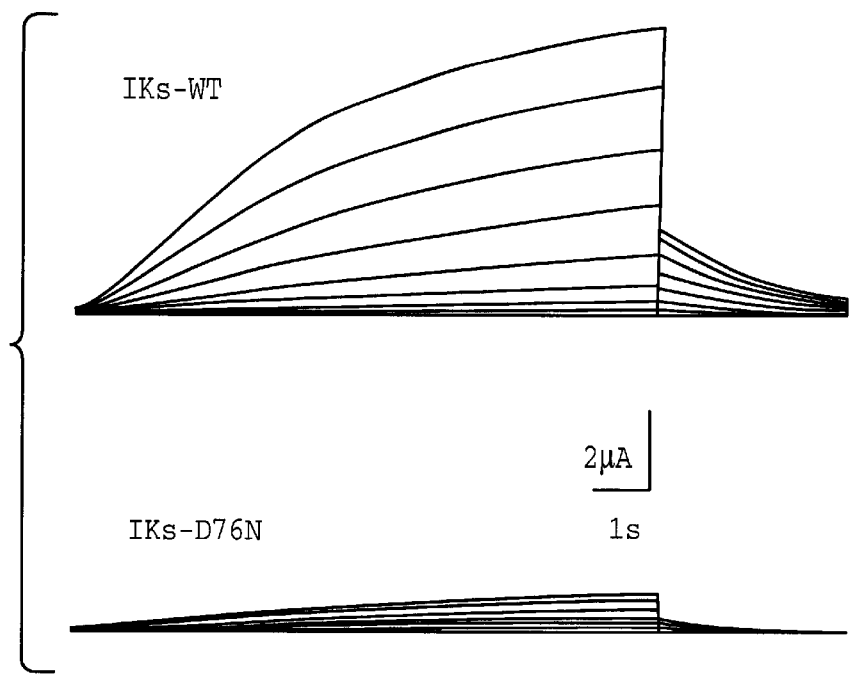
Figure 15B:
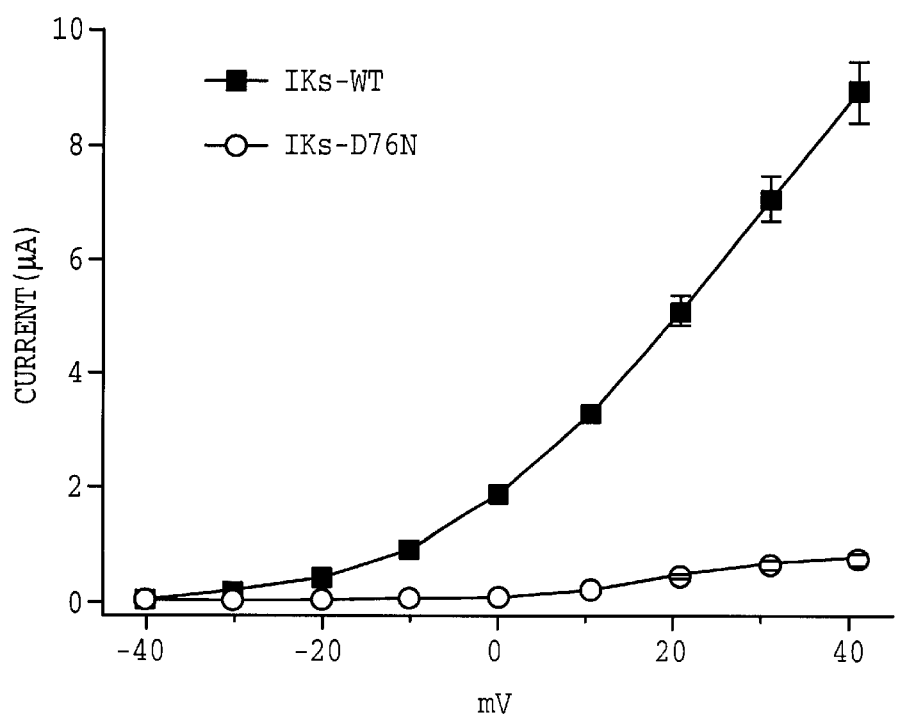

Coinjection of D76N KCNE1 and KVLQT1 cRNA failed to induce detectable K⁺ currents (n=13). Because LQT is inherited as an autosomal dominant trait, affected individuals possess one normal and one mutant KCNE1 allele. Therefore, mutant KCNE1 cRNA was coinjected with WT KCNE1 and KVLQT1 cRNA. The current ($I_{Ks-D76N}$) induced by coinjection of D76N KCNE1 (0.6 ng/oocyte), WT KCNE1 (0.6 ng/oocyte) and KVLQT1 cRNA (6 ng/oocyte) was 91% smaller than the current ($I_{Ks-WT}$) induced by WT KCNE1 (1.2 ng/oocyte) and KVLQT1 (6 ng/oocyte) cRNA at +40 mV (FIGS. 15A and 15B). Thee data indicate that D76N hminK subunits form heteromultimeric channels with WT hminK and KVLQT1, and reduce $I_{Ks}$ by a strong dominant-negative mechanism.

Figure 15C:
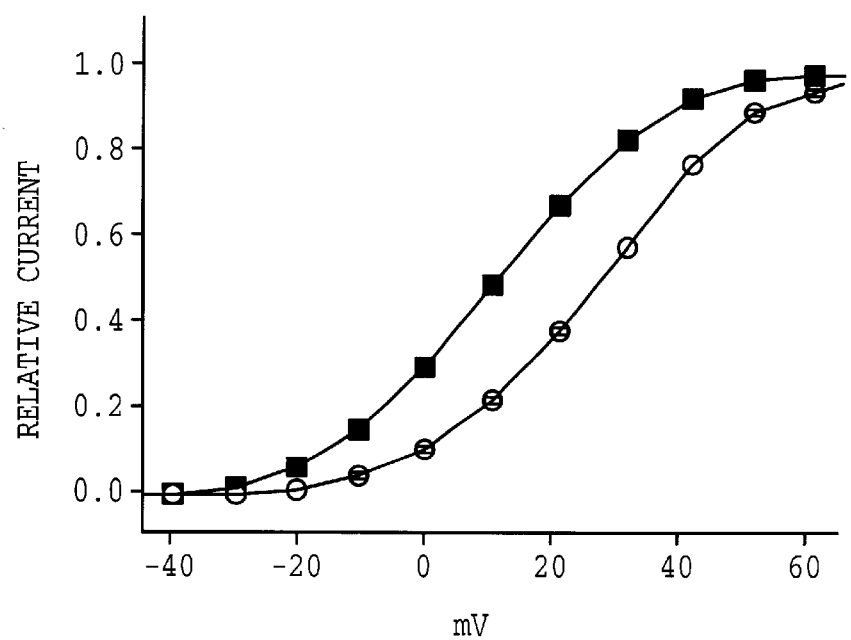
Figure 15D:
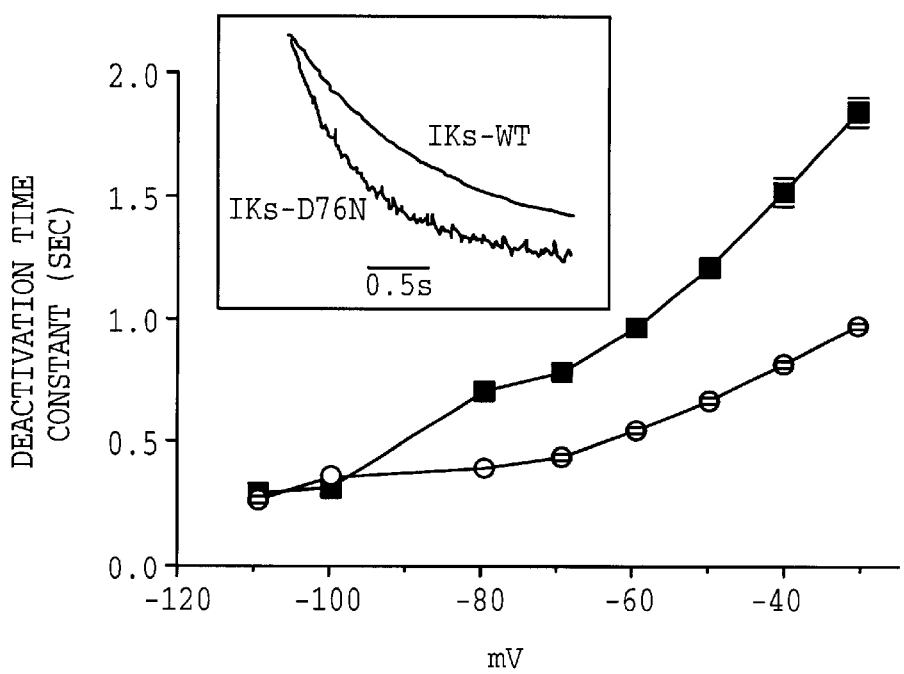

To compare the biophysical properties of wild-type and mutant channels, the voltage dependence of activation and the kinetics of deactivation for $I_{Ks-D76N}$ and $I_{Ks-WT}$ were characterized. The magnitude of $I_{Ks}$ does not reach steady state even when elicited with pulses of 100 second duration (Swanson et al., 1993). Therefore, tail current amplitude following 7.5 second test pulses was used as an empirical measure of the voltage dependence of $I_{Ks}$. $I_{Ks-D76N}$ tail currents were half-maximal at +28 mV, a +16 mV shift relative to $I_{Ks-WT}$ (FIG. 15C). A shift in channel gating was confirmed by the voltage dependence of current deactivation. The rate of $I_{Ks-D76N}$ channel closure (deactivation) was faster than $I_{Ks-WT}$ at voltages $\geq$ −80 mV (FIG. 15D). The voltage dependence of the time constants of deactivation were shifted by approximately +30 mV. Thus, D76N hminK reduces $I_{Ks}$ by three mechanisms: a dominant negative suppression of channel function, an increased rate of channel deactivation and a positive shift in the voltage dependence of channel activation. These effects would reduce outward current during the repolarization phase and lengthen the duration of a cardiac action potential.

Figure 16A:
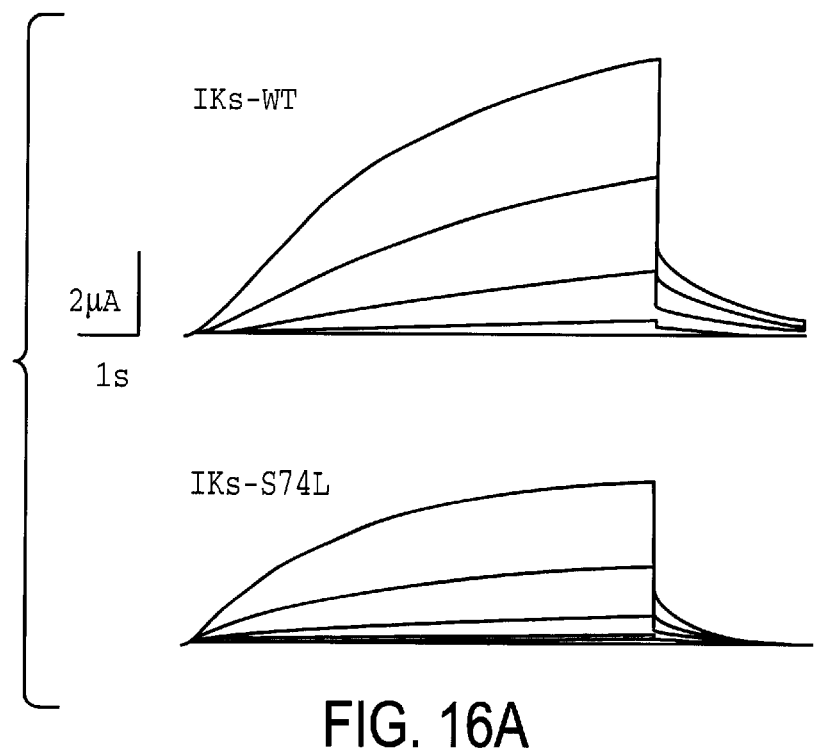
Figure 16B:
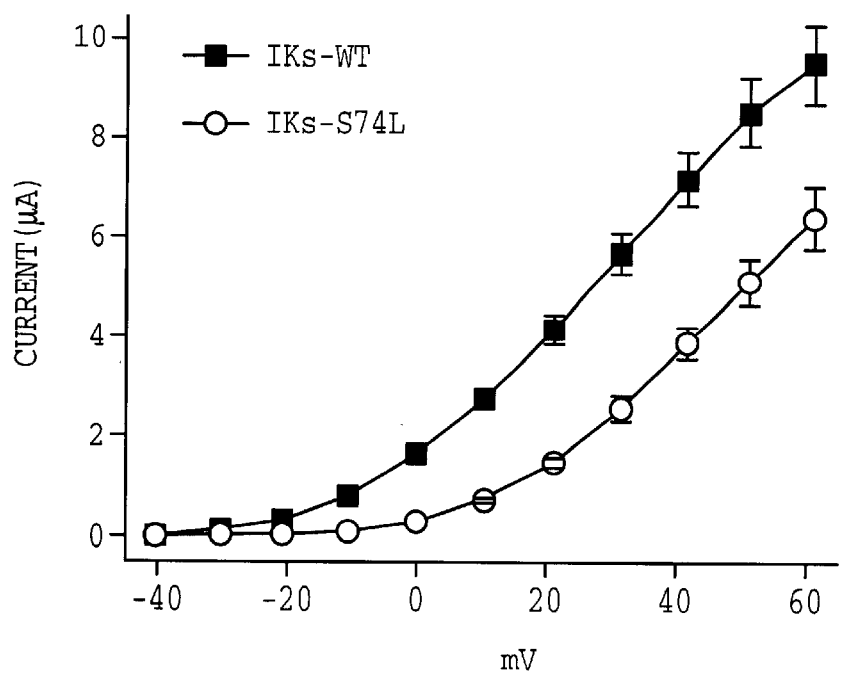
Figure 16C:
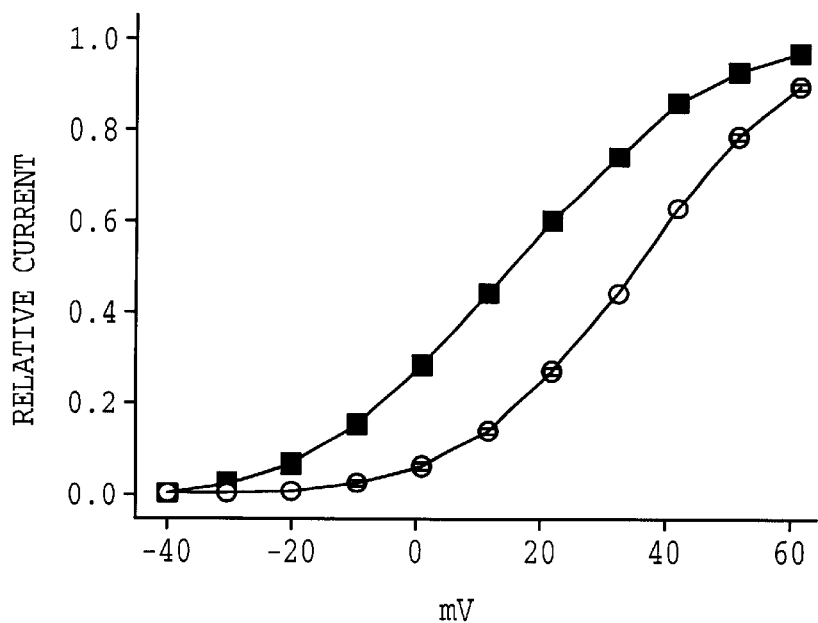
Figure 16D:
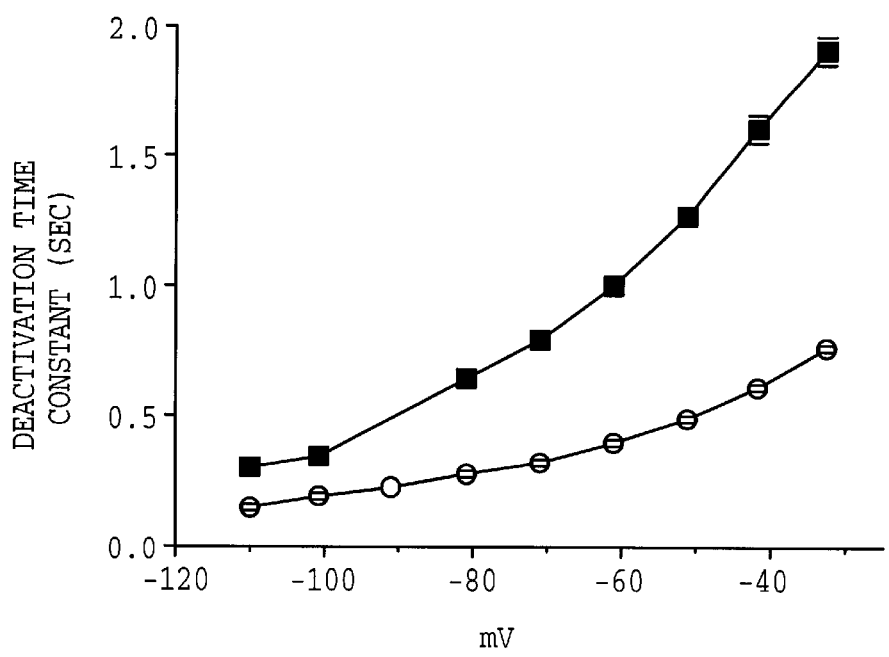

Unlike D76N hminK, S74L hminK formed $I_{Ks}$ channels when coexpressed with KVLQT1, albeit with altered function. Current induced by injection of S74L KCNE1 (1.2 ng/oocyte) and KVLQT1 (6.0 ng/oocyte) cRNA had a threshold for activation that was approximately 40 mV higher than $I_{Ks-WT}$. The resultant current was 66% smaller than $I_{Ks-WT}$ after 7.5 second pulses to +60 mV (n=15). When S74L KCNE1 (0.6 ng/oocyte) and WT KCNE1 (0.6 ng/oocyte) were coinjected with KVLQT1 (6.0 ng/oocyte) cRNA, the resultant current ($I_{Ks-S74L}$) was reduced by approximately 33% at +60 mV compared to $I_{Ks-WT}$ (FIGS. 16A–16B). As shown in FIG. 16C, this reduction was due primarily to a positive shift in the voltage dependence of current activation. The voltage dependence of deactivation was shifted approximately +40 mV (FIG. 16D). This shift caused a marked increase in the rate of $I_{Ks-S74L}$ deactivation. Thus, S74L hminK subunits form heteromultimeric channels with WT hminK and KVLQT1, and reduce $I_{Ks}$ by a shift in the voltage dependence of channel activation and an increased rate of channel deactivation. Because $I_{Ks-S74L}$ did not equal $I_{Ks-WT}$ at +60 mV (as expected for a simple shift in gating), it is possible tat S74L mutant subunits also reduce the number of functional $I_{Ks}$ channels and/or single channel conductance.

The observation that LQT-associated mutations of KCNE1 alter gating kinetics provides compelling evidence that hminK forms an integral part of the $I_{Ks}$ channel, rather than simply serving as a chaperone. Earlier studies of minK, performed before the discovery of KVLQT1, also support this conclusion (Takumi et al., 1991; Goldstein and Miller, 1991; Wang and Goldstein, 1995; K W Wang et al., 1996). In oe of these studies, a mutant rat minK subunit (D77N), analogous to D76N hminK, coassembled with WT minK and suppressed $I_{Ks}$ function, a dominant-lethal effect (Wang and Goldstein, 1995).

It is concluded that mutations in KCNE1, the gene that encodes β subunits of $I_{Ks}$ channels, cause arrhythmia susceptibility by reducing $I_{Ks}$ and thereby delaying myocellular repolarization. Because regional heterogeneity in $I_{Ks}$ exists within the myocardium (Liu and Antzelevitch, 1995), mutations in KCNE1 would cause abnormal regional disparity in action potential duration, creating a substrate for arrhythmia. The discovery of LQT-associated mutations in KCNE1 will facilitate presymptomatic diagnosis of this disorder and may have implications for therapy.

EXAMPLE 16

Genomic Structure of KCNE1

The genomic DNA of KCNE1 was examined and the exon/intron boundaries determined for all exons essentially as done for KVLQT1. An adult heart cDNA library was screened with a PCR product amplified from total human DNA and containing the entire coding sequence to isolate two identical 1.7 kb KCNE1 clones. Two overlapping cosmid clones encompassing the entire KCNE1 cDNA were also isolated using full length KCNE1 as a probe (FIG. 17). The cosmids were sequenced by a dideoxy chain termination method on an Applied Biosystems model 373A DNA sequencer to define the genomic structure of the KCNE1 gene. Three exons comprise KCNE1 cDNA (FIG. 18 and Table 8). The two introns were located in the 5'-UTR. The donor and acceptor splice sites for both introns were GT and AG, respectively. Three pairs of primers were designed for screening KCNE1 (Table 9). The first and second pair overlap and cover the entire coding sequence. The third pair amplifies part of the coding region including the putative transmembrane domain and some of the flanking sequences.

TABLE 8

Intron/Exon Boundaries in KCNE1

| Exon No. | intron/EXON[a] | EXON SIZE (bp) | EXON/Intron[a] |
|---|---|---|---|
| 1 | 5'UTR...CCACACCCG (95) | 33 | TCAGACCCGGgtgagttagg (96) |
| 2 | caatcaccagGAAAAATCCC (97) | 111 | GGATATTCAGgtaggacctg (98) |
| 3 | ttcctttaagAGGT...ATG (99) | 437 | TTCCCCATGA...3'UTR (100) |

[a]SEQ ID NO is shown in parentheses following each sequence

TABLE 9

Primers Used to Amplify KCNE1 Coding Sequence

| Exon No. | Forward Primer[a] | | Reverse Primer[a] | | Size (bp) | C[b] |
|---|---|---|---|---|---|---|
| 3 | CTGCAGCAGTGGAACCTTAATG | (101) | GTTCGAGTGCTCCAGCTTCTTG | (102) | 264 | 1 |
| 3 | GGGCATCATGCTGAGCTACAT | (103) | TTTAGCCAGTGGTGGGGTTCA | (104) | 231 | 1 |
| 3 | GTTCAGCAGGGTGGCAACAT | (105) | GCCAGATGGTTTTCAACGACA | (106) | 281 | 1 |

[a]SEQ ID NO is shown in parentheses following each sequence.
[b]Conditions of the PCR as described in Example 10D.

EXAMPLE 17

Generation of Polyclonal Antibody against KVLQT1 or KCNE1

Segments of KVLQT1 or KCNE1 coding sequence are expressed as fusion protein in E. coli. The overexpressed protein is purified by gel elution and used to immunize rabbits and mice using a procedure similar to the one described by Harlow and Lane (1988). This procedure has been shown to generate Abs against various other proteins (for example, see Kraemer et al., 1993).

Briefly, a stretch of KVLQT1 or KCNE1 coding sequence is cloned as a fusion protein in plasmid PET5A (Novagen, Inc., Madison, Wis.). After induction with IPTG, the overexpression of a fusion protein with the expected molecular weight is verified by SDS/PAGE. Fusion protein is purified from the gel by electroelution. Identification of the protein as the KVLQT1 or KCNE1 fusion product is verified by protein sequencing at the N-terminus. Next, the purified protein is used as immunogen in rabbits. Rabbits are immunized with 100 μg of the protein in complete Freund's adjuvant and boosted twice in 3 week intervals, first with 100 μg of immunogen in incomplete Freund's adjuvant followed by 100 μg of immunogen in PBS. Antibody containing serum is collected two weeks thereafter.

This procedure is repeated to generate antibodies against the mutant forms of the KVLQT1 or KCNE1 gene product. These antibodies, in conjunction with antibodies to wild type KVLQT1 or KCNE1, are used to detect the presence and the relative level of the mutant forms in various tissues and biological fluids.

EXAMPLE 18

Generation of Monoclonal Antibodies Specific for KVLQT1 or KCNE1

Monoclonal antibodies are generated according to the following protocol. Mice are immunized with immunogen comprising intact KVLQT1, KCNE1, KVLQT1 peptides or KCNE1 peptides (wild type or mutant) conjugated to keyhole limpet hemocyanin using glutaraldehyde or EDC as is well known.

The immunogen is mixed with an adjuvant. Each mouse receives four injections of 10 to 100 μg of immunogen and after the fourth injection blood samples are taken from the mice to determine if the serum contains antibody to the immunogen. Serum titer is determined by ELISA or RIA. Mice with sera indicating the presence of antibody to the immunogen are selected for hybridoma production.

Spleens are removed from immune mice and a single cell suspension is prepared (see Harlow and Lane, 1988). Cell fusions are performed essentially as described by Kohler and Milstein (1975). Briefly. P3.65.3 myeloma cells (American Type Culture Collection, Rockville Md.) are fused with immune spleen cells using polyethylene glycol as described by Harlow and Lane (1988). Cells are plated at a density of $2 \times 10^5$ cells/well in 96 well tissue culture plates. Individual wells are examined for growth and the supernatants of wells with growth are tested for the presence of KVLQT1 or KCNE1 specific antibodies by ELISA or RIA using wild type or mutant KVLQT1 or KCNE1 target protein. Cells in positive wells are expanded and subcloned to establish and confirm monoclonality.

Clones with the desired specificities are expanded and grown as ascites in mice or in a hollow fiber system to produce sufficient quantities of antibody for characterization and assay development.

EXAMPLE 19

Sandwich Assay for KVLQT1 or KCNE1

Monoclonal antibody is attached to a solid surface such as a plate, tube, bead or particle. Preferably, the antibody is attached to the well surface of a 96-well ELISA plate. 100 μL sample (e.g., serum, urine, tissue cytosol) containing the KVLQT1 or KCNE1 peptide/protein (wild-type or mutants) is added to the solid phase antibody. The sample is incubated for 2 hrs at room temperature. Next the sample fluid is decanted, and the solid phase is washed with buffer to remove unbound material. 100 μL of a second monoclonal antibody (to a different determinant on the KVLQT1 or KCNE1 peptide/protein) is added to the solid phase. This antibody is labeled with a detector molecule (e.g., $^{125}$I, enzyme, fluorophore, or a chromophore) and the solid phase with the second antibody is incubated for two hrs at room temperature. The second antibody is decanted and the solid phase is washed with buffer to remove unbound material.

The amount of bound label, which is proportional to the amount of KVLQT1 or KCNE1 peptide/protein present in the sample, is quantified. Separate assays are performed using monoclonal antibodies which are specific for the wild-type KVLQT1 or KCNE1 as well as monoclonal antibodies specific for each of the mutations identified in KVLQT1 or KCNE1.

EXAMPLE 20

Assay to Screen Drugs Affecting the KVLQT1 and KCNE1 K$^+$ Channel

With the knowledge that KVLQT1 and KCNE1 coassemble to form a cardiac $I_{Ks}$ potassium channel, it is now possible to devise an assay to screen for drugs which will have an effect on this channel. The two genes, KVLQT1 and KCNE1, are cotransfected into oocytes or mammalian cells and coexpressed as described above. The cotransfection is performed using any combination of wild-type or specifically mutated KVLQT1 and KCNE1. When one of the genes used for cotransfection contains a mutation which causes LQT a change in the induced current is seen as compared to cotransfection with wild-type genes only. A drug candidate is added to the bathing solution of the transfected cells to test the effects of the drug candidates upon the induced current. A drug candidate which alters the induced current such that it is closer to the current seen with cells cotransfected with wild-type KVLQT1 and KCNE1 is useful for treating LQT.

While the invention has been disclosed in this patent application by reference to the details of preferred embodiments of the invention, it is to be understood that the disclosure is intended in an illustrative rather than in a limiting sense, as it is contemplated that modifications will readily occur to those skilled in the art, within the spirit of the invention and the scope of the appended claims.

LIST OF REFERENCES

Altschul S F, et al. (1997). *Nucl. Acids Res.* 25:3389–3402.
Anand, R (1992). *Techniques for the Analysis of Complex Genomes,* (Academic Press).
Anderson W F, et al. (1980). *Proc. Natl. Acad. Sci. USA* 77:5399–5403.
Anderson M A and Gussella J F (1984). *In Vitro* 20:856–858.
Antzelevitch C and Sicouri S (1994). *J. Am. Col. Card.* 23:259–277.
Attali B, et al. (1993). *Nature* 365:850–852.
Attwell D, et al. (1979). *Pflugers Arch.* 379:137–142.
Ausubel F M, et al. (1992). *Current Protocols in Molecular Biology,* (John Wiley and Sons, New York, N.Y.).
Balser J R, et al. (1990). *J. Gen. Physiol.* 96:835–863.
Balser J R, et al. (1991). *Circ. Res.* 69:519–529.
Bandyopadhyay P K and Temin H M (1984). *Mol. Cell. Biol.* 4:749–754.
Barhanin J, et al. (1996). *Nature* 384:78–80.
Bartel P L, et al. (1993). "Using the 2-hybrid system to detect protein-protein interactions." In *Cellular Interactions in Development: A Practical Approach,* Oxford University Press, pp. 153–179.
Bazzett H (1920). *Heart* 7:353–370.
Beaucage S L and Caruthers M H (1981). *Tetra. Letts.* 22:1859–1862.
Berglund P, et al. (1993). *Biotechnology* 11:916–920.
Berkner K L, et al. (1988). *BioTechniques* 6:616–629.
Berkner K L, (1992). *Curr. Top. Microbiol. Immunol.* 158:39–66.
Borman S (1996). *Chemical & Engineering News,* December 9 issue. pp. 42–43.
Breakefield X O and Geller A I (1987). *Mol. Neurobiol.* 1:337–371.
Brinster R L, et al. (1981). *Cell* 27:223–231.
Bruggemann A, et al. (1993). *Nature* 365:445–448.
Buchschacher G L and Panganiban A T (1992). *J. Virol.* 66:2731–2739.
Buckler A J, et al. (1991). *Proc. Natl. Acad. Sci. USA* 88:4005–4009.
Burn T C, et al. (1995). *Gene* 161:183–187.
Busch A E, et al. (1992). *Science* 255:1705–1707.
Capecchi M R (1989). *Science* 244:1288.
Cardiac Arrhythmia Suppression Trial II Investigators (1992). *N. Engl. J. Med.* 327:227–233.
Cariello N F (1988). *Am. J. Human Genetics* 42:726–734.
Chee M, et al. (1996). *Science* 274:610–614.
Chevray P M and Nathans D N (1992). *Proc. Natl. Acad. Sci. USA* 89:5789–5793.
Chin H M, et al. (1991). *Genomics* 11:914–919.
Church D M, et al. (1994). *Nat. Genet.* 6:98–105.
Compton J (1991). *Nature* 350:91–92.
Conner B J, et al. (1983). *Proc. Natl. Acad. Sci. USA* 80:278–282.
Costantini F and Lacy E (1981). i Nature 294:92–94.
Cotten M, et al. (1990). *Proc. Natl. Acad. Sci. USA* 87:4033–4037.
Cotton R G, et al. (1988). *Proc. Natl. Acad. Sci. USA* 85:4397–4401.
Covarrubias M, et al. (1991). *Neuron* 7:763–773.
Cui J, et al. (1994). *J. Gen. Physiol.* 104:87–105.
Culver K W, et al. (1992). *Science* 256:1550–1552.
Culver K (1996). *Gene Therapy: A Primer for Physicians.* 2nd Ed., Mary Ann Liebert.
Curiel D T, et al. (1991). *Proc. Natl. Acad. Sci. USA* 88:8850–8854.
Curiel D T, et al. (1992). *Hum. Gene Ther.* 3:147–154.
Curran M E, et al. (1995). *Cell* 80:795–804.
DeRisi J, et al. (1996). *Nat. Genet.* 14:457–460.
Deutscher M (1990). *Meth. Enzymology* 182:83–89 (Academic Press. San Diego, Calif.).
Donehower L A, et al. (1992). *Nature* 356:215.
Duggal P et al. (1998). *Circulation* 97:142–146.
Editorial (1996). *Nature Genetics* 14:367–370.
Elghanian R, et al. (1997). *Science* 277:1078–1081.
Enhancers and Eukaryotic Gene Expression, Cold Spring Harbor Press, Cold Spring Harbor, N.Y. (1983).
Erickson J, et al. (1990). *Science* 249:527–533.
Fahy E, et al. (1991). *PCR Methods Appl.* 1:25–33.
Felgner P L, et al. (1987). *Proc. Natl. Acad. Sci. USA* 84:7413–7417.
Fields S and Song O-K (1989). *Nature* 340:245–246.
Fiers W, et al. (1978). *Nature* 273:113–120.
Fink D J, et al. (1992). *Hum. Gene Ther.* 3:11–19.
Fink D J, et al. (1996). *Ann. Rev. Neurosci.* 19:265–287.
Finkelstein J, et al. (1990). *Genomics* 7:167–172.
Fodor S P A (1997). *Science* 277:393–395.
Freese A, et al. (1990). *Biochem. Pharmacol.* 40:2189–2199.
Friedman T (1991). In *Therapy for Genetic Diseases,* T. Friedman, ed., Oxford University Press. pp. 105–121.
Gellens M, et al. (1992). *Proc. Natl. Acad. Sci. USA* 89:554–558.
George A L, et al. (1995). *Cytogenet. Cell. Genet.* 68:67–70.
Glover D (1985). *DNA Cloning,* I and II (Oxford Press).
Goding (1986). *Monoclonal Antibodies: Principles and Practice,* 2d ed. (Academic Press, N.Y.).
Godowski P J, et al. (1988). *Science* 241:812–816.
Goldstein S A N and Miller C (1991). *Neuron* 7:403–408.
Gordon J W, et al. (1980). *Proc. Natl. Acad. Sci. USA* 77:7380–7384.
Gorziglia M and Kapikian A Z (1992). *J. Virol.* 66:4407–4412.
Graham F L and van der Eb A J (1973). *Virology* 52:456–467.
Green E D and Olson M V (1990). *Proc. Natl. Acad. Sci. USA* 87:1213–1217.
Grompe M (1993). *Nature Genetics* 5:111–117.
Grompe M, et al. (1989). *Proc. Natl. Acad. Sci. USA* 86:5855–5892.
Guthrie G and Fink G R (1991). *Guide to Yeast Genetics and Molecular Biology* (Academic Press).
Gyapay G, et al. (1994). *Nat. Genet.* 7:246–339.
Hacia J G, et al. (1996). *Nature Genetics* 14:441–447.
Harlow E and Lane D (1988). *Antibodies: A laboratory Manual* (Cold Spring Harbor Laboratory, Cold Spring Harbor, N.Y.).
Hasty P K, et al. (1991). *Nature* 350:243.
Hausdorff S F, et al. (1991). *Biochem.* 30:3341–3346.

Heginbotham L, et al. (1994). *Biophys. J,* 66:1061–1067.
Helseth E, et al. (1990). *J. Virol.* 64:2416–2420.
Hodgson J (1991). *Bio/Technology* 9:19–21.
Huse W D, et al. (1989). *Science* 246:1275–1281.
Innis M A, et al. (1990). *PCR Protocols: A Guide to Methods and Applications* (Academic Press, San Diego).
Jablonski E, et al. (1986). *Nucl. Acids Res.* 14:6115–6128.
Jakoby W B and Pastan I H (eds.) (1979). *Cell Culture, Methods in Enzymology* volume 58 (Academic Press, Inc., Harcourt Brace Jovanovich (New York)).
January C T and Riddle J M (1989). *Circ. Res.* 64:977–990.
Jervell A and Lange-Nielsen F (1957). *Am. Heart J.* 54:59–68.
Jiang C, et al. (1994). *Nat. Genet.* 8:141–147.
Johnson P A, et al. (1992). *J. Virol.* 66:2952–2965.
Johnson, et al. (1993). "Peptide Turn Mimetics" in *Biotechnology and Pharmacy,* Pezzuto et al., eds., Chapman and Hall, New York.
Kaneda Y, et al. (1989). *J. Biol. Chem.* 264:12126–12129.
Kanehisa M (1984). *Nucl. Acids Res.* 12:203–213.
Kannel W B, et al. (1987). *Am. Heart J.* 113:799–804.
Keating M T, et al. (1991a). *Science* 252:704–706.
Keating M T, et al. (1991b). *Am. J. Hum. Genet.* 49:1335–1339.
Kinszler K W, et al. (1991). *Science* 251:1366–1370.
Kohler G and Milstein C (1975). *Nature* 256:495–497.
Kraemer F B, et al. (1993). *J. Lipid Res.* 34:663–672.
Kubo T, et al. (1988). *FEBS Lett.* 241:119.
Kwiatkowski T J, et al. (1990). *Nucl. Acids Res.* 18:7191–7192.
Kyte J and Doolittle R F (1982). *J. Mol. Biol.* 157:105–132.
Landegren U, et al. (1988). *Science* 242:229–237.
Lathrop, G M, et al. (1985). *Am. J. Hum. Genet.* 37:482–498.
Lee J E, et al. (1995). *Science* 268:836–844.
Lesage F, et al. (1993). *Receptors and Channel* 1:143–152.
Li G-R, et al. (1996). *Circ. Res.* 78:689–696.
Lim C S, et al. (1991). *Circulation* 83:2007–2011.
Lipshutz R J, et al. (1995). *BioTechniques* 19:442–447.
Liu D W and Antzelevitch C (1995). *Circ. Res.* 76:351–365.
Lockhart D J, et al. (1996). *Nature Biotechnology* 14:1675–1680.
MacKinnon R (1991). *Nature* 350:232–235.
MacKinnon R, et al. (1993). *Science* 262:757–759.
Madzak C, et al. (1992). *J. Gen. Virol.* 73:1533–1536.
Magovcevic I, et al. (1992). *Genomics* 12:125–129.
Maniatis T, et al. (1982). *Molecular Cloning: A Laboratory Manual* (Cold Spring Harbor Laboratory, Cold Spring Harbor, N.Y.).
Mann R and Baltimore D (1985). *J. Virol.* 54:401–407.
Marchuk D, et al. (1991). *Nucl. Acids Res.* 19:1154.
Margolskee R F (1992). *Curr. Top. Microbiol. Immunol.* 158:67–95.
Martin R, et al. (1990). *BioTechiques* 9:762–768.
Matsuura H, et al. (1987). *Pflugers Arch.* 410:596–603.
Matteucci M D and Caruthers M H (1981). *J. Am. Chem. Soc.* 103:3185.
Matthews J A and Kricka L J (1988). *Anal. Biochem.* 169:1.
Merrifield B (1963). *J. Am. Chem. Soc.* 85:2149–2156.
Metzger D, et al. (1988). *Nature* 334:31–36.
Mifflin T E (1989). *Clinical Chem.* 35:1819–1825.
Miller A D (1992). *Curr. Top. Microbiol. Immunol.* 158:1–24.
Miller A D, et al. (1985). *Mol. Cell. Biol.* 5:431–437.
Miller A D, et al. (1988). *J. Virol.* 62:4337–4345.
Modrich P (1991). *Ann. Rev. Genet.* 25:229–253.
Mombaerts P, et al. (1992). *Cell* 68:869.

Moss A J and McDonald J (1971). *N. Engl. J. Med.* 285:903–904.
Moss A J, et al. (1991). *Circulation* 84:1136–1144.
Moss B (1992). *Curr. Top. Microbiol. Immunol.* 158:25–38.
Moss B (1996). *Proc. Natl. Acad. Sci. USA* 93:11341–11348.
Muzyczka N (1992). *Curr. Top. Microbiol. Immunol.* 158:97–129.
Nabel E G, et al. (1990). *Science* 249:1285–1288.
Nabel (1992). *Hum. Gene Ther.* 3:399–410.
Naldini L, et al. (1996). *Science* 272:263–267.
Newton C R, et al. (1989). *Nucl. Acids Res.* 17:2503–2516.
Neyroud N, et al. (1997). *Nat. Genet.* 15:186–189.
Nguyen Q, et al. (1992). *BioTechniques* 13:116–123.
Novack D F, et al. (1986). *Proc. Natl. Acad. Sci. USA* 83:586–590.
Ochman H, et al. (1988). *Genetics* 120:621–623.
Ohi S, et al. (1990). *Gene* 89:279–282.
Orita M, et al. (1989). *Proc. Natl. Acad. Sci. USA* 86:2766–2770.
Page K A, et al. (1990). *J. Virol.* 64:5270–5276.
Pellicer A, et al. (1980). *Science* 209:1414–1422.
Petropoulos C J, et al. (1992). *J. Virol.* 66:3391–3397.
Philpott K L, et al. (1992). *Science* 256:1448.
Pongs O, et al. (1988). *EMBO J.* 7:1087–1095.
Quantin B, et al. (1992). *Proc. Natl. Acad. Sci. USA* 89:2581–2584.
*Remington's Pharmaceutical Sciences,* 18th Ed. (1990, Mack Publishing Co., Easton, Pa.).
Rettig J, et al. (1994). *Nature* 369:289–294.
Rigby P W J, et al. (1977). *J. Mol. Biol.* 113:237–251.
Romano C (1965). *Lancet* 1658–659.
Romano C, et al. (1963). *Clin. Pediatr.* 45:656–683.
Rosenfeld M A, et al. (1992). *Cell* 68:143–155.
Ruano G and Kidd K K (1989). *Nucl. Acids Res.* 17:8392.
Russell M W, et al. (1995). *Am. J. Hum. Genet.* 57:503–507.
Russell D and Hirata R (1998). *Nature Genetics* 18:323 328.
Sambrook J, et al. (1989). *Molecular Cloning: A Laboratory Manual,* 2nd Ed. (Cold Spring Harbor Laboratory, Cold Spring Harbor, N.Y.).
Sanguinetti M C and Jurkiewicz N K (1990). *J. Gen. Physiol.* 96:195–215.
Sanguinetti M C, et al. (1995). *Cell* 81:299–307.
Sanguinetti M C, et al. (1996a). *Proc. Natl. Acad. Sci. USA* 93:2208–2212.
Sanguinetti M C, et al. (1996b). *Nature* 384:80–83.
Scharf S J, et al. (1986). *Science* 233:1076–1078.
Schneider G, et al. (1998). *Nature Genetics* 18:180–183.
Schott J, et al. (1995). *Am. J. Hum. Genet.* 57:1114–1122.
Schultze-Bahr E, et al. (1997). *Nat. Genet.* 17:267–268.
Schwartz P J, et al. (1975). *Am. Heart J.* 109:378–390.
Schwartz P J, et al. (1994). "The long QT syndrome." In *Cardiac Electrophysiology: from cell to bedside.* D. P. Zipes and J. Jalife eds. (W. B. Sanders Company) pp.788–811.
Scopes P (1982). *Protein Purification: Principles and Practice.* (Springer-Verlag, New York).
Seino S, et al. (1992). *Genomics* 13: 1375–1377.
Sheffield V C, et al. (1989). *Proc. Natl. Acad. Sci. USA* 86:232–236.
Sheffield V C, et al. (1991). *Am. J. Hum. Genet.* 49:699–706.
Shenk T E, et al. (1975). *Proc. Natl. Acad. Sci. USA* 72:989–993.
Shi G, et al. (1996). *Neuron* 16:843–852.
Shimada T, et al. (1991). *J. Clin. Invest.* 88:1043–1047.
Shinkai Y, et al. (1992). *Cell* 68:855.
Shoemaker D D, et al. (1996). *Nature Genetics* 14:450–456.

Smith P L, et al. (1996). *Nature* 379:833–836.
Snouwaert J N, et al. (1992). *Science* 257:1083.
Sorge J, et al. (1984). *Mol. Cell. Biol.* 4:1730–1737.
Spargo C A, et al. (1996). *Mol. Cell. Probes* 10:247–256.
Spector P S, et al. (1996). *J. Gen. Physiol.* 107:611–619.
Splawski I, et al. (1997a). *N. Engl. J. Med.* 336:1562–1567.
Splawski I, et al. (1997b). *Nat. Genet.* 17:338–340.
Sternberg N (1990). *Proc. Natl. Acad. Sci. USA* 87:103–107.
Stewart M J, et al. (1992). *Hum. Gene Ther.* 3:267–275.
Stratford-Perricaudet L D, et al. (1990). *Hum. Gene Ther.* 1:241–256.
Surawicz B (1989). *J. Am. Coll. Cardiol.* 14:172–184.
Swanson R, et al. (1993). *Seminars in the Neurosciences* 5:117–124.
Takumi T, et al. (1988). *Science* 242:1042–1045.
Takumi T, et al. (1991). *J. Biol. Chem.* 266:22192–22198.
Tanigami A, et al. (1992). *Am. J. Hum. Genet.* 50:56–64.
Tokino T, et al. (1991). *Am. J. Hum. Genet.* 48:258–268.
Tyson J, et al. (1997). *Hum. Mol. Genet.* 6:2179–2185.
Valancius V and Smithies O (1991). *Mol. Cell Biol.* 11:1402.
Vetter D E, et al. (1996). Neuron 17:1251–1264.
Vincent G M, et al. (1992). *N. Engl. J. Med.* 327:846–852.
Wagner E, et al. (1991). *Proc. Natl. Acad. Sci. USA* 88:4255–4259.
Wagner E, et al. (1990). *Proc. Natl. Acad. Sci. USA* 87:3410–3414.
Walker G T, et al., (1992). *Nucl. Acids Res.* 20:1691–1696.
Wang K W and Goldstein S A (1995). *Neuron* 14:1303–1309.
Wang K W, et al. (1996). *Neuron* 16:571–577.
Wang C Y and Huang L (1989). *Biochemistry* 28:9508–9514.
Wang Q and Keating M T (1994). *BioTechniques* 17:282–284.
Wang Q, et al. (1995a). *Cell* 80:805–811.
Wang Q, et al. (1995b). *Hum. Mol. Genet.* 4:1603–1607.
Wang Q, et al. (1996). *Nat. Genet.* 12:17–23.
Ward O C (1964). *J. Ir. Med. Assoc.* 54:103–106.
Warmke J E and Ganetzky B (1994). *Proc. Natl. Acad. Sci.* 91::3438–3442.
Wartell R M, et al. (1990). *Nucl. Acids Res.* 8:2699–2705.
Weinstein L S et al. (1988). *FEBS Letters* 232:333–340.
Wells J A (1991). *Methods Enzymol.* 202:390–411.
Wetmur J G and Davidson N (1968). *J. Mol. Biol.* 31:349–370.
White M B, et al. (1992). *Genomics* 12:301–306.
White R and Lalouel J M (1988). *Annu. Rev,. Genet.* 99:259–979.
Wilkinson G W and Akrigg A (1992). *Nucleic Acids Res.* 20:2233–2239.
Willich S N, et al. (1987). *Am. J. Cardiol.* 60:801–806.
Wolff J A, et al. (1990). *Science* 247:1465–1468.
Wolff J A, et al. (1991). BioTechniques 11:474–485.
Wu D Y and Wallace R B (1989). *Genomics* 4:560–569.
Wu C H, et al. (1989). *J. Biol. Chem.* 264:16985–16987.
Wu G Y, et al. (1991). *J. Biol. Chem.* 266:14338–14342.
Wymore R S, et al. (1994). *Genomics* 20:191202.
Yang W P, et al. (1997). *Proc. Natl. Acad. Sci. USA* 94:4017–4021.
Zenke M, et al. (1990). *Proc. Natl. Acad. Sci. USA* 87:3655–3659.
Zipes D P (1987). *Am. J. Cardiol.* 59:26E–31E.
Patents and Patent Applications
European Patent Application Publication No. 0332435.
EPO Publication No. 225,807.
Hitzeman et al., EP 73.675A.
EP 425,731 A.
WO 84/03564.
WO 90/07936.
WO 92/19195.
WO 93/07282.
WO 94/25503.
WO 95/01203.
WO 95/05452.
WO 96/02286.
WO 96/02646.
WO 96/11698.
WO 96/40871.
WO 96/40959.
WO 97/02048.
WO 97/12635.
U.S. Pat. No. 3,817,837.
U.S. Pat. No. 3,850,752.
U.S. Pat. No. 3,939,350.
U.S. Pat. No. 3,996,345.
U.S. Pat. No. 4,275,149.
U.S. Pat. No. 4,277,437.
U.S. Pat. No. 4,366,241.
U.S. Pat. No. 4,376,110.
U.S. Pat. No. 4,486,530.
U.S. Pat. No. 4,554,101.
U.S. Pat. No. 4,683,195.
U.S. Pat. No. 4,683,202.
U.S. Pat. No. 4,816,567.
U.S. Pat. No. 4,868,105.
U.S. Pat. No. 5,252,479.
U.S. Pat. No. 5,270,184.
U.S. Pat. No. 5,409,818.
U.S. Pat. No. 5,436,146.
U.S. Pat. No. 5,455,166.
U.S. Pat. No. 5,550,050.
U.S. Pat. No. 5,691,198.
U.S. Pat. No. 5,735,500.
U.S. Pat. No. 5,747,469.

What is claimed is:

1. An isolated DNA comprising nucleic acid of SEQ ID NO:3 or its complement.
2. A cell transfected with the DNA of claim 1.
3. A vector comprising the isolated DNA of claim 1.
4. A cell transfected with the vector of claim 3.
5. An isolated DNA encoding a polypeptide of SEQ ID NO:4 comprising a mutation, wherein said mutation causes said isolated DNA to encode:
   a) a leucine at codon 74,
   b) an asparagine at codon 76,
   c) a leucine at codon 28,
   d) a histidine at codon 32,
   e) a tryptophan at codon 98,
   f) an alanine at codon 127, or
   g) a threonine at codon 127.
6. A cell transfected with the DNA of claim 5.
7. A vector comprising the isolated DNA of claim 5.
8. A cell transfected with the vector of claim 7.
9. An isolated DNA of SEQ ID NO: 3 comprising a mutation, wherein said mutation is selected from:
   a) an A at base 418,
   b) a T at base 413,
   c) a T at base 275,
   d) an A at base 287,
   e) a T at base 484,
   f) a G at base 571, or
   g) an A at base 571.
10. A cell transfected with the DNA of claim 9.
11. A vector comprising the isolated DNA of claim 9.
12. A cell transfected with the vector of claim 11.
13. A cell transfected with a nucleic acid encoding a polypeptide of SEQ ID NO:4 wherein said polypeptide comprises:
   a) a Leu rather than a Ser at residue 74,
   b) an Asn rather than an Asp at residue 76,
   c) a Leu rather than a Ser at residue 28,
   d) a His rather than an Arg at residue 32,
   e) a Frp rather than an Arg at residue 98,
   f) an Ala rather than a Pro at residue 127, or
   g) a Thrrather than a Pro at residue 127.
14. A cell cotransfected with:
   A) i) a nucleic acid encoding a polypeptide of SEQ ID NO:4 and ii) a nucleic acid encoding a polypeptide of SEQ ID NO:2;
   B) i) a nucleic acid encoding a polypeptide of SEQ ID NO:4 and ii) a nucleic acid encoding a polypeptide of SEQ ID NO:2 comprising a missense mutation;
   C) i) a nucleic acid encoding a polypeptide of SEQ ID NO:4 comprising a missense mutation and ii) a nucleic encoding a polypeptide of SEQ ID NO:2; or
   D) i) a nucleic acid encoding a polypeptide of SEQ ID NO:4 comprising a missense mutation and ii) a nucleic acid encoding a polypeptide of SEQ ID NO:2 comprising a missense mutation.
15. The cell of claim 14 wherein:
   i) said missense mutation of SEQ ID NO:4 is selected from the group consisting of:

a) a Leu at residue 28,
b) a His at residue 32,
c) a Leu at residue 74,
d) an Asn at residue 76,
e) a Trp at residue 98,
f) an Ala at residue 127, and
g) a Thr at residue 127; and ii) said missense mutation of SEQ ID NO:2 is selected from the group consisting of:
a) a Pro at residue 178,
b) an Arg at residue 189,
c) a Gin at residue 190,
d) a Met at residue 254,
e) a Phe at residue 273,
f) an Arg at residue 306,
g) an Ile at residue 312,
h) a Glu at residue 341,
i) a Val at residue 341,
j) a Glu at residue 345,
k) an Arg at residue 168,
l) a Ser at residue 314,
m) a Cys at residue 315,
n) an Asn at residue 318,
o) a Pro at residue 353, and
p) a Trp at residue 366.

16. A cell cotransfected with:
i) a nucleic acid encoding a polypeptide of SEQ ID NO:4; and
ii) a nucleic acid encoding a polypeptide of SEQ ID NO:2 comprising a Trp at residue 167 and a deletion of residue 168.

17. A cell cotransfected with:
i) a nucleic acid encoding a polypeptide of SEQ ID NO:4 comprising a missense mutation; and
ii) a nucleic acid encoding a polypeptide of SEQ ID NO:2 comprising a Trp at residue 167 and a deletion of residue 168.

18. The cell of claim 17 wherein said missense mutation of SEQ ID NO:4 is selected from the group consisting of:
a) a Leu at residue 28,
b) a His at residue 32,
c) a Leu at residue 74,
d) an Asn at residue 76,
e) a Trp at residue 98,
f) an Ala at residue 127, and
g) a Thr at residue 127.

* * * * *

SEQUENCE LISTING

<160> NUMBER OF SEQ ID NOS: 114

<210> SEQ ID NO 1
<211> LENGTH: 3181
<212> TYPE: DNA
<213> ORGANISM: Homo sapiens
<220> FEATURE:
<221> NAME/KEY: CDS
<222> LOCATION: (163)..(2190)

<400> SEQUENCE: 1

```
ctgcccctc cggccccgcc ccgagcgccc gggctgggcc ggcagcggcc cccgcggcg    60 gggctggcag cagtggctgc ccgcactgcg cccgggcgct cgccttcgct gcagctcccg   120
gtgccgccgc tcgggccggc ccccggcag gccctcctcg tt atg gcc gcg gcc      174
                                            Met Ala Ala Ala
                                             1 tcc tcc ccg ccc agg gcc gag agg aag cgc tgg ggt tgg ggc cgc ctg    222
Ser Ser Pro Pro Arg Ala Glu Arg Lys Arg Trp Gly Trp Gly Arg Leu
  5              10                  15                  20 cca ggc gcc cgg cgg ggc agc gcg ggc ctg gcc aag aag tgc ccc ttc    270
Pro Gly Ala Arg Arg Gly Ser Ala Gly Leu Ala Lys Lys Cys Pro Phe
                 25                  30                  35 tcg ctg gag ctg gcg gag ggc ggc ccg gcg ggc ggc gcg ctc tac gcg    318
Ser Leu Glu Leu Ala Glu Gly Gly Pro Ala Gly Gly Ala Leu Tyr Ala
             40                  45                  50 ccc atc gcg ccc ggc gcc cca ggt ccc gcg ccc cct gcg tcc ccg gcc    366
Pro Ile Ala Pro Gly Ala Pro Gly Pro Ala Pro Pro Ala Ser Pro Ala
         55                  60                  65 gcg ccc gcc gcg ccc cca gtt gcc tcc gac ctt ggc ccg cgg ccg ccg    414
Ala Pro Ala Ala Pro Pro Val Ala Ser Asp Leu Gly Pro Arg Pro Pro
 70                  75                  80 gtg agc cta gac ccg cgc gtc tcc atc tac agc acg cgc cgc ccg gtg    462
Val Ser Leu Asp Pro Arg Val Ser Ile Tyr Ser Thr Arg Arg Pro Val
 85                  90                  95                 100 ttg gcg cgc acc cac gtc cag ggc cgc gtc tac aac ttc ctc gag cgt    510
Leu Ala Arg Thr His Val Gln Gly Arg Val Tyr Asn Phe Leu Glu Arg
                105                 110                 115 ccc acc ggc tgg aaa tgc ttc gtt tac cac ttc gcc gtc ttc ctc atc    558
Pro Thr Gly Trp Lys Cys Phe Val Tyr His Phe Ala Val Phe Leu Ile
            120                 125                 130 gtc ctg gtc tgc ctc atc ttc agc gtg ctg tcc acc atc gag cag tat    606
Val Leu Val Cys Leu Ile Phe Ser Val Leu Ser Thr Ile Glu Gln Tyr
            135                 140                 145 gcc gcc ctg gcc acg ggg act ctc ttc tgg atg gag atc gtg ctg gtg    654
Ala Ala Leu Ala Thr Gly Thr Leu Phe Trp Met Glu Ile Val Leu Val
150                 155                 160 gtg ttc ttc ggg acg gag tac gtg gtc cgc ctc tgg tcc gcc ggc tgc    702
Val Phe Phe Gly Thr Glu Tyr Val Val Arg Leu Trp Ser Ala Gly Cys
165                 170                 175                 180 cgc agc aag tac gtg ggc ctc tgg ggg cgg ctg cgc ttt gcc cgg aag    750
Arg Ser Lys Tyr Val Gly Leu Trp Gly Arg Leu Arg Phe Ala Arg Lys
                185                 190                 195 ccc att tcc atc atc gac ctc atc gtg gtc gtg gcc tcc atg gtg gtc    798
Pro Ile Ser Ile Ile Asp Leu Ile Val Val Val Ala Ser Met Val Val
            200                 205                 210 ctc tgc gtg ggc tcc aag ggg cag gtg ttt gcc acg tcg gcc atc agg    846
Leu Cys Val Gly Ser Lys Gly Gln Val Phe Ala Thr Ser Ala Ile Arg
            215                 220                 225 ggc atc cgc ttc ctg cag atc ctg agg atg cta cac gtc gac cgc cag    894
Gly Ile Arg Phe Leu Gln Ile Leu Arg Met Leu His Val Asp Arg Gln
            230                 235                 240 gga ggc acc tgg agg ctc ctg ggc tcc gtg gtc ttc atc cac cgc cag    942
Gly Gly Thr Trp Arg Leu Leu Gly Ser Val Val Phe Ile His Arg Gln
245                 250                 255                 260 gag ctg ata acc acc ctg tac atc ggc ttc ctg ggc ctc atc ttc tcc    990
Glu Leu Ile Thr Thr Leu Tyr Ile Gly Phe Leu Gly Leu Ile Phe Ser
            265                 270                 275 tcg tac ttt gtg tac ctg gct gag aag gac gcg gtg aac gag tca ggc   1038
```

```
Ser Tyr Phe Val Tyr Leu Ala Glu Lys Asp Ala Val Asn Glu Ser Gly
            280                 285                 290 cgc gtg gag ttc ggc agc tac gca gat gcg ctg tgg tgg ggg gtg gtc       1086
Arg Val Glu Phe Gly Ser Tyr Ala Asp Ala Leu Trp Trp Gly Val Val
            295                 300                 305 aca gtc acc acc atc ggc tat ggg gac aag gtg ccc cag acg tgg gtc       1134
Thr Val Thr Thr Ile Gly Tyr Gly Asp Lys Val Pro Gln Thr Trp Val
310             315                 320 ggg aag acc atc gcc tcc tgc ttc tct gtc ttt gcc atc tcc ttc ttt       1182
Gly Lys Thr Ile Ala Ser Cys Phe Ser Val Phe Ala Ile Ser Phe Phe
325             330                 335                 340 gcg ctc cca gcg ggg att ctt ggc tcg ggg ttt gcc ctg aag gtg cag       1230
Ala Leu Pro Ala Gly Ile Leu Gly Ser Gly Phe Ala Leu Lys Val Gln
                345                 350                 355 cag aag cag agg cag aag cac ttc aac cgg cag atc ccg gcg gca gcc       1278
Gln Lys Gln Arg Gln Lys His Phe Asn Arg Gln Ile Pro Ala Ala Ala
            360                 365                 370 tca ctc att cag acc gca tgg agg tgc tat gct gcc gag aac ccc gac       1326
Ser Leu Ile Gln Thr Ala Trp Arg Cys Tyr Ala Ala Glu Asn Pro Asp
            375                 380                 385 tcc tcc acc tgg aag atc tac atc cgg aag gcc ccc cgg agc cac act       1374
Ser Ser Thr Trp Lys Ile Tyr Ile Arg Lys Ala Pro Arg Ser His Thr
        390                 395                 400 ctg ctg tca ccc agc ccc aaa ccc aag aag tct gtg gtg gta aag aaa       1422
Leu Leu Ser Pro Ser Pro Lys Pro Lys Lys Ser Val Val Val Lys Lys
405             410                 415                 420 aaa aag ttc aag ctg gac aaa gac aat ggg gtg act cct gga gag aag       1470
Lys Lys Phe Lys Leu Asp Lys Asp Asn Gly Val Thr Pro Gly Glu Lys
                425                 430                 435 atg ctc aca gtc ccc cat atc acg tgc gac ccc cca gaa gag cgg cgg       1518
Met Leu Thr Val Pro His Ile Thr Cys Asp Pro Pro Glu Glu Arg Arg
            440                 445                 450 ctg gac cac ttc tct gtc gac ggc tat gac agt tct gta agg aag agc       1566
Leu Asp His Phe Ser Val Asp Gly Tyr Asp Ser Ser Val Arg Lys Ser
            455                 460                 465 cca aca ctg ctg gaa gtg agc atg ccc cat ttc atg aga acc aac agc       1614
Pro Thr Leu Leu Glu Val Ser Met Pro His Phe Met Arg Thr Asn Ser
        470                 475                 480 ttc gcc gag gac ctg gac ctg gaa ggg gag act ctg ctg aca ccc atc       1662
Phe Ala Glu Asp Leu Asp Leu Glu Gly Glu Thr Leu Leu Thr Pro Ile
485             490                 495                 500 acc cac atc tca cag ctg cgg gaa cac cat cgg gcc acc att aag gtc       1710
Thr His Ile Ser Gln Leu Arg Glu His His Arg Ala Thr Ile Lys Val
                505                 510                 515 att cga cgc atg cag tac ttt gtg gcc aag aag aaa ttc cag caa gcg       1758
Ile Arg Arg Met Gln Tyr Phe Val Ala Lys Lys Lys Phe Gln Gln Ala
            520                 525                 530 cgg aag cct tac gat gtg cgg gac gtc att gag cag tac tcg cag ggc       1806
Arg Lys Pro Tyr Asp Val Arg Asp Val Ile Glu Gln Tyr Ser Gln Gly
            535                 540                 545 cac ctc aac ctc atg gtg cgc atc aag gag ctg cag agg agg ctg gac       1854
His Leu Asn Leu Met Val Arg Ile Lys Glu Leu Gln Arg Arg Leu Asp
        550                 555                 560 cag tcc att ggg aag ccc tca ctg ttc atc tcc gtc tca gaa aag agc       1902
Gln Ser Ile Gly Lys Pro Ser Leu Phe Ile Ser Val Ser Glu Lys Ser
565             570                 575                 580 aag gat cgc ggc agc aac acg atc ggc gcc cgc ctg aac cga gta gaa       1950
Lys Asp Arg Gly Ser Asn Thr Ile Gly Ala Arg Leu Asn Arg Val Glu
                585                 590                 595
```

-continued

| | |
|---|---|
| gac aag gtg acg cag ctg gac cag agg ctg gca ctc atc acc gac atg<br>Asp Lys Val Thr Gln Leu Asp Gln Arg Leu Ala Leu Ile Thr Asp Met<br>600 605 610 | 1998 |
| ctt cac cag ctg ctc tcc ttg cac ggt ggc agc acc ccc ggc agc ggc<br>Leu His Gln Leu Leu Ser Leu His Gly Gly Ser Thr Pro Gly Ser Gly<br>615 620 625 | 2046 |
| ggc ccc ccc aga gag ggc ggg gcc cac atc acc cag ccc tgc ggc agt<br>Gly Pro Pro Arg Glu Gly Gly Ala His Ile Thr Gln Pro Cys Gly Ser<br>630 635 640 | 2094 |
| ggc ggc tcc gtc gac cct gag ctc ttc ctg ccc agc aac acc ctg ccc<br>Gly Gly Ser Val Asp Pro Glu Leu Phe Leu Pro Ser Asn Thr Leu Pro<br>645 650 655 660 | 2142 |
| acc tac gag cag ctg acc gtg ccc agg agg ggc ccc gat gag ggg tcc<br>Thr Tyr Glu Gln Leu Thr Val Pro Arg Arg Gly Pro Asp Glu Gly Ser<br>665 670 675 | 2190 |
| tgaggagggg atgggctgg gggatgggcc tgagtgagag gggaggccaa gagtggcccc | 2250 |
| acctggccct ctctgaagga ggccacctcc taaaaggccc agagagaaga gccccactct | 2310 |
| cagaggcccc aatacccat ggaccatgct gtctggcaca gcctgcactt ggggctcag | 2370 |
| caaggccacc tcttcctggc cggtgtgggg gccccgtctc aggtctgagt tgttacccca | 2430 |
| agcgccctgg ccccacatg gtgatgttga catcactggc atggtggttg ggacccagtg | 2490 |
| gcagggcaca gggcctggcc catgtatggc caggaagtag cacaggctga gtgcaggccc | 2550 |
| accctgcttg gcccagggg cttcctgagg ggagacagag caaccctgg accccagcct | 2610 |
| caaatccagg accctgccag gcacaggcag ggcaggacca gccacgctg actacagggc | 2670 |
| caccggcaat aaaagcccag gagcccattt ggagggcctg ggcctggctc cctcactctc | 2730 |
| aggaaatgct gacccatggg caggagactg tggagactgc tcctgagccc ccagcttcca | 2790 |
| gcaggaggga cagtctcacc atttccccag ggcacgtggt tgagtggggg aacgcccac | 2850 |
| ttccctgggt tagactgcca gctcttccta gctggagagg agccctgcct ctccgcccct | 2910 |
| gagcccactg tgcgtgggc tcccgcctcc aaccctcgc ccagtcccag cagccagcca | 2970 |
| aacacacaga aggggactgc cacctcccct tgccagctgc tgagccgcag agaagtgacg | 3030 |
| gttcctacac aggacagggg ttccttctgg gcattacatc gcatagaaat caataatttg | 3090 |
| tggtgatttg gatctgtgtt ttaatgagtt tcacagtgtg attttgatta ttaattgtgc | 3150 |
| aagctttcc taataaacgt ggagaatcac a | 3181 |

<210> SEQ ID NO 2
<211> LENGTH: 676
<212> TYPE: PRT
<213> ORGANISM: Homo sapiens

<400> SEQUENCE: 2

Met Ala Ala Ser Ser Pro Pro Arg Ala Glu Arg Lys Arg Trp Gly
1               5                   10                  15

Trp Gly Arg Leu Pro Gly Ala Arg Arg Gly Ser Ala Gly Leu Ala Lys
                20                  25                  30

Lys Cys Pro Phe Ser Leu Glu Leu Ala Glu Gly Gly Pro Ala Gly Gly
            35                  40                  45

Ala Leu Tyr Ala Pro Ile Ala Pro Gly Ala Pro Gly Pro Ala Pro Pro
        50                  55                  60

Ala Ser Pro Ala Ala Pro Ala Ala Pro Val Ala Ser Asp Leu Gly
65                  70                  75                  80

Pro Arg Pro Pro Val Ser Leu Asp Pro Arg Val Ser Ile Tyr Ser Thr
                85                  90                  95

-continued

```
Arg Arg Pro Val Leu Ala Arg Thr His Val Gln Gly Arg Val Tyr Asn
            100                 105                 110
Phe Leu Glu Arg Pro Thr Gly Trp Lys Cys Phe Val Tyr His Phe Ala
            115                 120                 125
Val Phe Leu Ile Val Leu Val Cys Leu Ile Phe Ser Val Leu Ser Thr
            130                 135                 140
Ile Glu Gln Tyr Ala Ala Leu Ala Thr Gly Thr Leu Phe Trp Met Glu
145                 150                 155                 160
Ile Val Leu Val Val Phe Phe Gly Thr Glu Tyr Val Val Arg Leu Trp
                    165                 170                 175
Ser Ala Gly Cys Arg Ser Lys Tyr Val Gly Leu Trp Gly Arg Leu Arg
                    180                 185                 190
Phe Ala Arg Lys Pro Ile Ser Ile Ile Asp Leu Ile Val Val Val Ala
                    195                 200                 205
Ser Met Val Val Leu Cys Val Gly Ser Lys Gly Gln Val Phe Ala Thr
            210                 215                 220
Ser Ala Ile Arg Gly Ile Arg Phe Leu Gln Ile Leu Arg Met Leu His
225                 230                 235                 240
Val Asp Arg Gln Gly Gly Thr Trp Arg Leu Leu Gly Ser Val Val Phe
                    245                 250                 255
Ile His Arg Gln Glu Leu Ile Thr Thr Leu Tyr Ile Gly Phe Leu Gly
                    260                 265                 270
Leu Ile Phe Ser Ser Tyr Phe Val Tyr Leu Ala Glu Lys Asp Ala Val
                    275                 280                 285
Asn Glu Ser Gly Arg Val Glu Phe Gly Ser Tyr Ala Asp Ala Leu Trp
290                 295                 300
Trp Gly Val Val Thr Val Thr Thr Ile Gly Tyr Gly Asp Lys Val Pro
305                 310                 315                 320
Gln Thr Trp Val Gly Lys Thr Ile Ala Ser Cys Phe Ser Val Phe Ala
                    325                 330                 335
Ile Ser Phe Phe Ala Leu Pro Ala Gly Ile Leu Gly Ser Gly Phe Ala
                    340                 345                 350
Leu Lys Val Gln Gln Lys Gln Arg Gln Lys His Phe Asn Arg Gln Ile
            355                 360                 365
Pro Ala Ala Ala Ser Leu Ile Gln Thr Ala Trp Arg Cys Tyr Ala Ala
370                 375                 380
Glu Asn Pro Asp Ser Ser Thr Trp Lys Ile Tyr Ile Arg Lys Ala Pro
385                 390                 395                 400
Arg Ser His Thr Leu Leu Ser Pro Ser Pro Lys Pro Lys Lys Ser Val
                    405                 410                 415
Val Val Lys Lys Lys Lys Phe Lys Leu Asp Lys Asp Asn Gly Val Thr
                    420                 425                 430
Pro Gly Glu Lys Met Leu Thr Val Pro His Ile Thr Cys Asp Pro Pro
            435                 440                 445
Glu Glu Arg Arg Leu Asp His Phe Ser Val Asp Gly Tyr Asp Ser Ser
            450                 455                 460
Val Arg Lys Ser Pro Thr Leu Leu Glu Val Ser Met Pro His Phe Met
465                 470                 475                 480
Arg Thr Asn Ser Phe Ala Glu Asp Leu Asp Leu Glu Gly Glu Thr Leu
                    485                 490                 495
Leu Thr Pro Ile Thr His Ile Ser Gln Leu Arg Glu His His Arg Ala
            500                 505                 510
```

```
Thr Ile Lys Val Ile Arg Arg Met Gln Tyr Phe Val Ala Lys Lys Lys
        515                 520                 525

Phe Gln Gln Ala Arg Lys Pro Tyr Asp Val Arg Asp Val Ile Glu Gln
        530                 535                 540

Tyr Ser Gln Gly His Leu Asn Leu Met Val Arg Ile Lys Glu Leu Gln
545                 550                 555                 560

Arg Arg Leu Asp Gln Ser Ile Gly Lys Pro Ser Leu Phe Ile Ser Val
                565                 570                 575

Ser Glu Lys Ser Lys Asp Arg Gly Ser Asn Thr Ile Gly Ala Arg Leu
            580                 585                 590

Asn Arg Val Glu Asp Lys Val Thr Gln Leu Asp Gln Arg Leu Ala Leu
        595                 600                 605

Ile Thr Asp Met Leu His Gln Leu Leu Ser Leu His Gly Gly Ser Thr
        610                 615                 620

Pro Gly Ser Gly Gly Pro Pro Arg Glu Gly Gly Ala His Ile Thr Gln
625                 630                 635                 640

Pro Cys Gly Ser Gly Gly Ser Val Asp Pro Glu Leu Phe Leu Pro Ser
                645                 650                 655

Asn Thr Leu Pro Thr Tyr Glu Gln Leu Thr Val Pro Arg Arg Gly Pro
            660                 665                 670

Asp Glu Gly Ser
        675

<210> SEQ ID NO 3
<211> LENGTH: 1703
<212> TYPE: DNA
<213> ORGANISM: Homo sapiens
<220> FEATURE:
<221> NAME/KEY: CDS
<222> LOCATION: (193)..(579)

<400> SEQUENCE: 3
acacccggct ctctcggcat ctcagacccg ggaaaaatcc ctctgctttc tctggccagt     60
ttcacacaat catcaggtga gccgaggatc cattggagga aggcattatc tgtatccaga    120
ggaaatagcc aaggatattc agaggtgtgc ctgggaagtt tgagctgcag cagtggaacc    180
ttaatgccca gg atg atc ctg tct aac aca aca gcg gtg acg ccc ttt ctg    231
              Met Ile Leu Ser Asn Thr Thr Ala Val Thr Pro Phe Leu
                1               5                   10 acc aag ctg tgg cag gag aca gtt cag cag ggt ggc aac atg tcg ggc      279
Thr Lys Leu Trp Gln Glu Thr Val Gln Gln Gly Gly Asn Met Ser Gly
 15                  20                  25 ctg gcc cgc agg tcc ccc cgc agc ggt gac ggc aag ctg gag gcc ctc      327
Leu Ala Arg Arg Ser Pro Arg Ser Gly Asp Gly Lys Leu Glu Ala Leu
 30                  35                  40                  45 tac gtc ctc atg gta ctg gga ttc ttc ggc ttc ttc acc ctg ggc atc      375
Tyr Val Leu Met Val Leu Gly Phe Phe Gly Phe Phe Thr Leu Gly Ile
                 50                  55                  60 atg ctg agc tac atc cgc tcc aag aag ctg gag cac tcg aac gac cca      423
Met Leu Ser Tyr Ile Arg Ser Lys Lys Leu Glu His Ser Asn Asp Pro
         65                  70                  75 ttc aac gtc tac atc gag tcc gat gcc tgg caa gag aag gac aag gcc      471
Phe Asn Val Tyr Ile Glu Ser Asp Ala Trp Gln Glu Lys Asp Lys Ala
     80                  85                  90 tat gtc cag gcc cgg gtc ctg gag agc tac agg tcg tgc tat gtc gtt      519
Tyr Val Gln Ala Arg Val Leu Glu Ser Tyr Arg Ser Cys Tyr Val Val
 95                 100                 105 gaa aac cat ctg gcc ata gaa caa ccc aac aca cac ctt cct gag acg      567
```

```
Glu Asn His Leu Ala Ile Glu Gln Pro Asn Thr His Leu Pro Glu Thr
110                 115                 120                 125 aag cct tcc cca tgaaccccac cactggctaa actggacacc tcctgctggn          619
Lys Pro Ser Pro nnnnagattt tctaatcaca ttcctctcat actctttatt gtgatggata ccactggatt    679 tcttttttggc tgttgtaang ggtgagggg t ggattaatga cactgtttca ctgtttctct  739
aaaatcacgt tcttttgtga tagactgtca gtggttcccc catatctgtc cctgccttgc    799
taaatttagc agaatccctg aggacatggc tctgagaat agcagctgca tttcccagac     859
tcccttgcag ctagcaaggt tgtgtgacta agccctggcc agtaggcatg gaagtgaaga    919
ctgtaatgtc caagtaatcc ttggaaagaa aagaacgtgc ccttaactaa ctttgtcctg    979
cttcccagtg gctggatgtg gaggaggtgg agagcagtta tgagactggg aaagttcggg    1039
gcactcaaag agccacacac atctgggcct gggcgacgtg gatcctcctt accacccacc    1099
aggccagatt tacaggagag agaaatccac tccactcttc cttaagccac tgttattctg    1159
atctctgtta aggtcgcaga atcaatgccc ttactgatac acctaccta taggactgaa     1219 cctaaaggca tgacatttcc atacttgtca caagcacaca ctgattctgc ccttgtcact    1279
tctgtgctca ctcttgtggc tctatcctcc tcctgcccct tccgccttcca ctcctccctt   1339 gcacccatcc tgcacacatc tccctgaaaa cacacaggca catacactca tatacataga    1399
cacacataca cacctcaatc tagaaagaac ttgctttgta cagggctgag atggaggaga    1459
aaaaaatgcc cccttcagaa tgcataccaa ggggaaggtg ctcggtcact gtgggagcag    1519
ggaaaggtgc ccccactccc cgagagccag gggaaggagt ggctctgggc agagagggac    1579
acatagcact ggggtggcag gtccttttga ggtgatgggc cggttttgtg agatgaattg    1639
tatcccccaa aaagacaggt accttcaatg tgacctaatt gggaaataga gtctttgcag    1699
atga                                                                 1703

<210> SEQ ID NO 4
<211> LENGTH: 129
<212> TYPE: PRT
<213> ORGANISM: Homo sapiens

<400> SEQUENCE: 4

Met Ile Leu Ser Asn Thr Thr Ala Val Thr Pro Phe Leu Thr Lys Leu
 1               5                  10                  15

Trp Gln Glu Thr Val Gln Gln Gly Gly Asn Met Ser Gly Leu Ala Arg
                20                  25                  30

Arg Ser Pro Arg Ser Gly Asp Gly Lys Leu Glu Ala Leu Tyr Val Leu
            35                  40                  45

Met Val Leu Gly Phe Phe Gly Phe Phe Thr Leu Gly Ile Met Leu Ser
        50                  55                  60

Tyr Ile Arg Ser Lys Lys Leu Glu His Ser Asn Asp Pro Phe Asn Val
65                  70                  75                  80

Tyr Ile Glu Ser Asp Ala Trp Gln Glu Lys Asp Lys Ala Tyr Val Gln
                85                  90                  95

Ala Arg Val Leu Glu Ser Tyr Arg Ser Cys Tyr Val Val Glu Asn His
            100                 105                 110

Leu Ala Ile Glu Gln Pro Asn Thr His Leu Pro Glu Thr Lys Pro Ser
        115                 120                 125

Pro
```

```
<210> SEQ ID NO 5
<211> LENGTH: 63
<212> TYPE: DNA
<213> ORGANISM: Artificial Sequence
<220> FEATURE:
<223> OTHER INFORMATION: Description of Artificial Sequence:Hypothetical
      sequence to demonstrate calculation of percent
      homology or identity.

<400> SEQUENCE: 5
accgtagcta cgtacgtata tagaaagggc gcgatcgtcg tcgcgtatga cgacttagca      60
tgc                                                                   63

<210> SEQ ID NO 6
<211> LENGTH: 130
<212> TYPE: DNA
<213> ORGANISM: Artificial Sequence
<220> FEATURE:
<223> OTHER INFORMATION: Description of Artificial Sequence:Hypothetical
      sequence to demonstrate calculation of percent
      homology or identity.

<400> SEQUENCE: 6
accggtagct acgtacgtta tttagaaagg ggtgtgtgtg tgtgtgtaaa ccggggtttt      60
cgggatcgtc cgtcgcgtat gacgacttag ccatgcacgg tatatcgtat taggactagc    120
gattgactag                                                           130

<210> SEQ ID NO 7
<211> LENGTH: 17
<212> TYPE: DNA
<213> ORGANISM: Homo sapiens

<400> SEQUENCE: 7
cagatcctga ggatgct                                                    17

<210> SEQ ID NO 8
<211> LENGTH: 17
<212> TYPE: DNA
<213> ORGANISM: Homo sapiens

<400> SEQUENCE: 8
gtacctggct gagaagg                                                    17

<210> SEQ ID NO 9
<211> LENGTH: 10
<212> TYPE: DNA
<213> ORGANISM: Homo sapiens

<400> SEQUENCE: 9
atggccgcgg                                                            10

<210> SEQ ID NO 10
<211> LENGTH: 20
<212> TYPE: DNA
<213> ORGANISM: Homo sapiens

<400> SEQUENCE: 10
acttcgccgt gtgagtatcg                                                 20

<210> SEQ ID NO 11
<211> LENGTH: 20
<212> TYPE: DNA
<213> ORGANISM: Homo sapiens
```

-continued

```
<400> SEQUENCE: 11
tgtcttgcag cttcctcatc                                                20

<210> SEQ ID NO 12
<211> LENGTH: 20
<212> TYPE: DNA
<213> ORGANISM: Homo sapiens

<400> SEQUENCE: 12
cttctggatg gtacgtagca                                                20

<210> SEQ ID NO 13
<211> LENGTH: 20
<212> TYPE: DNA
<213> ORGANISM: Homo sapiens

<400> SEQUENCE: 13
gtccctgcag gagatcgtgc                                                20

<210> SEQ ID NO 14
<211> LENGTH: 20
<212> TYPE: DNA
<213> ORGANISM: Homo sapiens

<400> SEQUENCE: 14
tccatcatcg gtgagtcatg                                                20

<210> SEQ ID NO 15
<211> LENGTH: 20
<212> TYPE: DNA
<213> ORGANISM: Homo sapiens

<400> SEQUENCE: 15
cactccacag acctcatcgt                                                20

<210> SEQ ID NO 16
<211> LENGTH: 20
<212> TYPE: DNA
<213> ORGANISM: Homo sapiens

<400> SEQUENCE: 16
gggccatcag gtgcgtctgt                                                20

<210> SEQ ID NO 17
<211> LENGTH: 20
<212> TYPE: DNA
<213> ORGANISM: Homo sapiens

<400> SEQUENCE: 17
tccttcgcag gggcatccgc                                                20

<210> SEQ ID NO 18
<211> LENGTH: 20
<212> TYPE: DNA
<213> ORGANISM: Homo sapiens

<400> SEQUENCE: 18
ccaccgccag gtgggtggcc                                                20

<210> SEQ ID NO 19
<211> LENGTH: 20
<212> TYPE: DNA
<213> ORGANISM: Homo sapiens
```

<400> SEQUENCE: 19
tctggcctag gagctgataa                                                    20

<210> SEQ ID NO 20
<211> LENGTH: 20
<212> TYPE: DNA
<213> ORGANISM: Homo sapiens

<400> SEQUENCE: 20 gtgggggtg gtaagtcgga                                                     20

<210> SEQ ID NO 21
<211> LENGTH: 20
<212> TYPE: DNA
<213> ORGANISM: Homo sapiens

<400> SEQUENCE: 21
ctccctgcag gtcacagtca                                                    20

<210> SEQ ID NO 22
<211> LENGTH: 20
<212> TYPE: DNA
<213> ORGANISM: Homo sapiens

<400> SEQUENCE: 22
gctcccagcg gtaggtgccc                                                    20

<210> SEQ ID NO 23
<211> LENGTH: 20
<212> TYPE: DNA
<213> ORGANISM: Homo sapiens

<400> SEQUENCE: 23
tccttcccag gggattcttg                                                    20

<210> SEQ ID NO 24
<211> LENGTH: 20
<212> TYPE: DNA
<213> ORGANISM: Homo sapiens

<400> SEQUENCE: 24
actcattcag gtgcggtgcc                                                    20

<210> SEQ ID NO 25
<211> LENGTH: 20
<212> TYPE: DNA
<213> ORGANISM: Homo sapiens

<400> SEQUENCE: 25
cccacctcag accgcatgga                                                    20

<210> SEQ ID NO 26
<211> LENGTH: 20
<212> TYPE: DNA
<213> ORGANISM: Homo sapiens

<400> SEQUENCE: 26
gtctgtggtg gtgagtagcc                                                    20

<210> SEQ ID NO 27
<211> LENGTH: 20
<212> TYPE: DNA

```
<213> ORGANISM: Homo sapiens

<400> SEQUENCE: 27 tttttttag gtaaagaaaa                                              20

<210> SEQ ID NO 28
<211> LENGTH: 20
<212> TYPE: DNA
<213> ORGANISM: Homo sapiens

<400> SEQUENCE: 28
gacagttctg gtgagaaccc                                             20

<210> SEQ ID NO 29
<211> LENGTH: 20
<212> TYPE: DNA
<213> ORGANISM: Homo sapiens

<400> SEQUENCE: 29
ttctcctcag taaggaagag                                             20

<210> SEQ ID NO 30
<211> LENGTH: 20
<212> TYPE: DNA
<213> ORGANISM: Homo sapiens

<400> SEQUENCE: 30
acatctcaca gtgagtgcct                                             20

<210> SEQ ID NO 31
<211> LENGTH: 20
<212> TYPE: DNA
<213> ORGANISM: Homo sapiens

<400> SEQUENCE: 31
tccactgcag gctgcgggaa                                             20

<210> SEQ ID NO 32
<211> LENGTH: 20
<212> TYPE: DNA
<213> ORGANISM: Homo sapiens

<400> SEQUENCE: 32
gaaattccag gtaagccctg                                             20

<210> SEQ ID NO 33
<211> LENGTH: 20
<212> TYPE: DNA
<213> ORGANISM: Homo sapiens

<400> SEQUENCE: 33
tgtcccgcag caagcgcgga                                             20

<210> SEQ ID NO 34
<211> LENGTH: 20
<212> TYPE: DNA
<213> ORGANISM: Homo sapiens

<400> SEQUENCE: 34
tgcagaggag gtgggcacgg                                             20

<210> SEQ ID NO 35
<211> LENGTH: 20
```

```
<212> TYPE: DNA
<213> ORGANISM: Homo sapiens

<400> SEQUENCE: 35
ttctctccag gctggaccag                                              20

<210> SEQ ID NO 36
<211> LENGTH: 20
<212> TYPE: DNA
<213> ORGANISM: Homo sapiens

<400> SEQUENCE: 36
tccgtctcag gtgggtttct                                              20

<210> SEQ ID NO 37
<211> LENGTH: 20
<212> TYPE: DNA
<213> ORGANISM: Homo sapiens

<400> SEQUENCE: 37
tcccccatag aaaagagcaa                                              20

<210> SEQ ID NO 38
<211> LENGTH: 20
<212> TYPE: DNA
<213> ORGANISM: Homo sapiens

<400> SEQUENCE: 38
agaagacaag gtaggctcac                                              20

<210> SEQ ID NO 39
<211> LENGTH: 20
<212> TYPE: DNA
<213> ORGANISM: Homo sapiens

<400> SEQUENCE: 39
gtccccgcag gtgacgcagc                                              20

<210> SEQ ID NO 40
<211> LENGTH: 10
<212> TYPE: DNA
<213> ORGANISM: Homo sapiens

<400> SEQUENCE: 40
ggggtcctga                                                         10

<210> SEQ ID NO 41
<211> LENGTH: 19
<212> TYPE: DNA
<213> ORGANISM: Homo sapiens

<400> SEQUENCE: 41
ctcgccttcg ctgcagctc                                               19

<210> SEQ ID NO 42
<211> LENGTH: 19
<212> TYPE: DNA
<213> ORGANISM: Homo sapiens

<400> SEQUENCE: 42
gcgcgggtct aggctcacc                                               19

<210> SEQ ID NO 43
```

```
<211> LENGTH: 18
<212> TYPE: DNA
<213> ORGANISM: Homo sapiens

<400> SEQUENCE: 43
cgccgcgccc ccagttgc                                                    18

<210> SEQ ID NO 44
<211> LENGTH: 19
<212> TYPE: DNA
<213> ORGANISM: Homo sapiens

<400> SEQUENCE: 44
cagagctccc ccacaccag                                                   19

<210> SEQ ID NO 45
<211> LENGTH: 24
<212> TYPE: DNA
<213> ORGANISM: Homo sapiens

<400> SEQUENCE: 45
atgggcagag gccgtgatgc tgac                                             24

<210> SEQ ID NO 46
<211> LENGTH: 22
<212> TYPE: DNA
<213> ORGANISM: Homo sapiens

<400> SEQUENCE: 46
atccagccat gccctcagat gc                                               22

<210> SEQ ID NO 47
<211> LENGTH: 24
<212> TYPE: DNA
<213> ORGANISM: Homo sapiens

<400> SEQUENCE: 47
gttcaaacag gttgcagggt ctga                                             24

<210> SEQ ID NO 48
<211> LENGTH: 21
<212> TYPE: DNA
<213> ORGANISM: Homo sapiens

<400> SEQUENCE: 48
cttcctggtc tggaaacctg g                                                21

<210> SEQ ID NO 49
<211> LENGTH: 20
<212> TYPE: DNA
<213> ORGANISM: Homo sapiens

<400> SEQUENCE: 49
ctcttccctg gggccctggc                                                  20

<210> SEQ ID NO 50
<211> LENGTH: 22
<212> TYPE: DNA
<213> ORGANISM: Homo sapiens

<400> SEQUENCE: 50 tgcggggag cttgtggcac ag                                                22
```

```
<210> SEQ ID NO 51
<211> LENGTH: 22
<212> TYPE: DNA
<213> ORGANISM: Homo sapiens

<400> SEQUENCE: 51
tcagccccac accatctcct tc                                              22

<210> SEQ ID NO 52
<211> LENGTH: 20
<212> TYPE: DNA
<213> ORGANISM: Homo sapiens

<400> SEQUENCE: 52
ctgggcccct accctaaccc                                                 20

<210> SEQ ID NO 53
<211> LENGTH: 23
<212> TYPE: DNA
<213> ORGANISM: Homo sapiens

<400> SEQUENCE: 53
tcctggagcc cgacactgtg tgt                                             23

<210> SEQ ID NO 54
<211> LENGTH: 22
<212> TYPE: DNA
<213> ORGANISM: Homo sapiens

<400> SEQUENCE: 54
tgtcctgccc actcctcagc ct                                              22

<210> SEQ ID NO 55
<211> LENGTH: 20
<212> TYPE: DNA
<213> ORGANISM: Homo sapiens

<400> SEQUENCE: 55
tggctgacca ctgtccctct                                                 20

<210> SEQ ID NO 56
<211> LENGTH: 22
<212> TYPE: DNA
<213> ORGANISM: Homo sapiens

<400> SEQUENCE: 56
ccccaggacc ccagctgtcc aa                                              22

<210> SEQ ID NO 57
<211> LENGTH: 21
<212> TYPE: DNA
<213> ORGANISM: Homo sapiens

<400> SEQUENCE: 57
gctggcagtg gcctgtgtgg a                                               21

<210> SEQ ID NO 58
<211> LENGTH: 24
<212> TYPE: DNA
<213> ORGANISM: Homo sapiens

<400> SEQUENCE: 58
aacagtgacc aaaatgacag tgac                                            24
```

<210> SEQ ID NO 59
<211> LENGTH: 19
<212> TYPE: DNA
<213> ORGANISM: Homo sapiens

<400> SEQUENCE: 59
tggctcagca ggtgacagc                                            19

<210> SEQ ID NO 60
<211> LENGTH: 19
<212> TYPE: DNA
<213> ORGANISM: Homo sapiens

<400> SEQUENCE: 60
tggtggcagg tgggctact                                            19

<210> SEQ ID NO 61
<211> LENGTH: 19
<212> TYPE: DNA
<213> ORGANISM: Homo sapiens

<400> SEQUENCE: 61
gcctggcaga cgatgtcca                                            19

<210> SEQ ID NO 62
<211> LENGTH: 19
<212> TYPE: DNA
<213> ORGANISM: Homo sapiens

<400> SEQUENCE: 62
caactgcctg agggttct                                             19

<210> SEQ ID NO 63
<211> LENGTH: 20
<212> TYPE: DNA
<213> ORGANISM: Homo sapiens

<400> SEQUENCE: 63
ctgtccccac actttctcct                                           20

<210> SEQ ID NO 64
<211> LENGTH: 20
<212> TYPE: DNA
<213> ORGANISM: Homo sapiens

<400> SEQUENCE: 64
tgagctccag tccctccag                                            20

<210> SEQ ID NO 65
<211> LENGTH: 19
<212> TYPE: DNA
<213> ORGANISM: Homo sapiens

<400> SEQUENCE: 65
tggccactca caatctcct                                            19

<210> SEQ ID NO 66
<211> LENGTH: 19
<212> TYPE: DNA
<213> ORGANISM: Homo sapiens

<400> SEQUENCE: 66
gccttgacac cctccacta                                            19

<210> SEQ ID NO 67
<211> LENGTH: 19
<212> TYPE: DNA
<213> ORGANISM: Homo sapiens

<400> SEQUENCE: 67
ggcacaggga ggagaagtg                                                  19

<210> SEQ ID NO 68
<211> LENGTH: 19
<212> TYPE: DNA
<213> ORGANISM: Homo sapiens

<400> SEQUENCE: 68
cggcaccgct gatcatgca                                                  19

<210> SEQ ID NO 69
<211> LENGTH: 19
<212> TYPE: DNA
<213> ORGANISM: Homo sapiens

<400> SEQUENCE: 69
ccagggccag gtgtgactg                                                  19

<210> SEQ ID NO 70
<211> LENGTH: 20
<212> TYPE: DNA
<213> ORGANISM: Homo sapiens

<400> SEQUENCE: 70
tgggcccaga gtaactgaca                                                 20

<210> SEQ ID NO 71
<211> LENGTH: 21
<212> TYPE: DNA
<213> ORGANISM: Homo sapiens

<400> SEQUENCE: 71
ggccctgatt tgggtgtttt a                                               21

<210> SEQ ID NO 72
<211> LENGTH: 19
<212> TYPE: DNA
<213> ORGANISM: Homo sapiens

<400> SEQUENCE: 72
ggacgctaac cagaaccac                                                  19

<210> SEQ ID NO 73
<211> LENGTH: 20
<212> TYPE: DNA
<213> ORGANISM: Homo sapiens

<400> SEQUENCE: 73
caccactgac tctctcgtct                                                 20

<210> SEQ ID NO 74
<211> LENGTH: 18
<212> TYPE: DNA
<213> ORGANISM: Homo sapiens

<400> SEQUENCE: 74

-continued ccatccccca gccccatc                                              18

<210> SEQ ID NO 75
<211> LENGTH: 22
<212> TYPE: DNA
<213> ORGANISM: Homo sapiens

<400> SEQUENCE: 75
gagatcgtgc tggtggtgtt ct                                         22

<210> SEQ ID NO 76
<211> LENGTH: 21
<212> TYPE: DNA
<213> ORGANISM: Homo sapiens

<400> SEQUENCE: 76
cttcctggtc tggaaacctg g                                          21

<210> SEQ ID NO 77
<211> LENGTH: 20
<212> TYPE: DNA
<213> ORGANISM: Homo sapiens

<400> SEQUENCE: 77
ctcttccctg gggccctggc                                            20

<210> SEQ ID NO 78
<211> LENGTH: 22
<212> TYPE: DNA
<213> ORGANISM: Homo sapiens

<400> SEQUENCE: 78
tgcgggggag cttgtggcac ag                                         22

<210> SEQ ID NO 79
<211> LENGTH: 20
<212> TYPE: DNA
<213> ORGANISM: Homo sapiens

<400> SEQUENCE: 79
gggcatccgc ttcctgcaga                                            20

<210> SEQ ID NO 80
<211> LENGTH: 20
<212> TYPE: DNA
<213> ORGANISM: Homo sapiens

<400> SEQUENCE: 80
ctgggcccct accctaaccc                                            20

<210> SEQ ID NO 81
<211> LENGTH: 22
<212> TYPE: DNA
<213> ORGANISM: Homo sapiens

<400> SEQUENCE: 81
tcctggagcc cgaactgtgt gt                                         22

<210> SEQ ID NO 82
<211> LENGTH: 22
<212> TYPE: DNA
<213> ORGANISM: Homo sapiens

<400> SEQUENCE: 82

-continued tgtcctgccc actcctcagc ct    22

<210> SEQ ID NO 83
<211> LENGTH: 22
<212> TYPE: DNA
<213> ORGANISM: Homo sapiens

<400> SEQUENCE: 83
ccccaggacc ccagctgtcc aa    22

<210> SEQ ID NO 84
<211> LENGTH: 20
<212> TYPE: DNA
<213> ORGANISM: Homo sapiens

<400> SEQUENCE: 84
aggctgacca ctgtccctct    20

<210> SEQ ID NO 85
<211> LENGTH: 21
<212> TYPE: DNA
<213> ORGANISM: Homo sapiens

<400> SEQUENCE: 85
gctggcagtg gcctgtgtgg a    21

<210> SEQ ID NO 86
<211> LENGTH: 24
<212> TYPE: DNA
<213> ORGANISM: Homo sapiens

<400> SEQUENCE: 86
aacagtgacc aaaatgacag tgac    24

<210> SEQ ID NO 87
<211> LENGTH: 22
<212> TYPE: DNA
<213> ORGANISM: Homo sapiens

<400> SEQUENCE: 87
ctgcagcagt ggaaccttaa tg    22

<210> SEQ ID NO 88
<211> LENGTH: 22
<212> TYPE: DNA
<213> ORGANISM: Homo sapiens

<400> SEQUENCE: 88
gttcgagtgc tccagcttct tg    22

<210> SEQ ID NO 89
<211> LENGTH: 22
<212> TYPE: DNA
<213> ORGANISM: Homo sapiens

<400> SEQUENCE: 89
agggcatcat gctgagctac at    22

<210> SEQ ID NO 90
<211> LENGTH: 21
<212> TYPE: DNA
<213> ORGANISM: Homo sapiens

<400> SEQUENCE: 90
tttagccagt ggtggggttc a                                            21

<210> SEQ ID NO 91
<211> LENGTH: 20
<212> TYPE: DNA
<213> ORGANISM: Homo sapiens

<400> SEQUENCE: 91
gttcagcagg gtggcaacat                                              20

<210> SEQ ID NO 92
<211> LENGTH: 21
<212> TYPE: DNA
<213> ORGANISM: Homo sapiens

<400> SEQUENCE: 92
gccagatggt tttcaacgac a                                            21

<210> SEQ ID NO 93
<211> LENGTH: 28
<212> TYPE: DNA
<213> ORGANISM: Homo sapiens
<220> FEATURE:
<221> NAME/KEY: misc_difference
<222> LOCATION: (9)
<223> OTHER INFORMATION: Base change made to create a restriction enzyme
      site.

<400> SEQUENCE: 93
cagtggaagc ttaatgccca ggatgatc                                     28

<210> SEQ ID NO 94
<211> LENGTH: 35
<212> TYPE: DNA
<213> ORGANISM: Homo sapiens
<220> FEATURE:
<221> NAME/KEY: misc_difference
<222> LOCATION: (7)..(8)
<223> OTHER INFORMATION: Base changes made to create a restriction
      enzyme site.

<400> SEQUENCE: 94
caggaggatc cagtttagcc agtggtgggg gttca                             35

<210> SEQ ID NO 95
<211> LENGTH: 9
<212> TYPE: DNA
<213> ORGANISM: Homo sapiens

<400> SEQUENCE: 95 ccacacccg                                                           9

<210> SEQ ID NO 96
<211> LENGTH: 20
<212> TYPE: DNA
<213> ORGANISM: Homo sapiens

<400> SEQUENCE: 96
tcagacccgg gtgagttagg                                              20

<210> SEQ ID NO 97
<211> LENGTH: 20
<212> TYPE: DNA
<213> ORGANISM: Homo sapiens

```
<400> SEQUENCE: 97
caatcaccag gaaaaatccc                                          20

<210> SEQ ID NO 98
<211> LENGTH: 20
<212> TYPE: DNA
<213> ORGANISM: Homo sapiens

<400> SEQUENCE: 98
ggatattcag gtaggacctg                                          20

<210> SEQ ID NO 99
<211> LENGTH: 14
<212> TYPE: DNA
<213> ORGANISM: Homo sapiens

<400> SEQUENCE: 99
ttcctttaag aggt                                                14

<210> SEQ ID NO 100
<211> LENGTH: 10
<212> TYPE: DNA
<213> ORGANISM: Homo sapiens

<400> SEQUENCE: 100
ttccccatga                                                     10

<210> SEQ ID NO 101
<211> LENGTH: 22
<212> TYPE: DNA
<213> ORGANISM: Homo sapiens

<400> SEQUENCE: 101
ctgcagcagt ggaaccttaa tg                                       22

<210> SEQ ID NO 102
<211> LENGTH: 22
<212> TYPE: DNA
<213> ORGANISM: Homo sapiens

<400> SEQUENCE: 102
gttcgagtgc tccagcttct tg                                       22

<210> SEQ ID NO 103
<211> LENGTH: 21
<212> TYPE: DNA
<213> ORGANISM: Homo sapiens

<400> SEQUENCE: 103
gggcatcatg ctgagctaca t                                        21

<210> SEQ ID NO 104
<211> LENGTH: 21
<212> TYPE: DNA
<213> ORGANISM: Homo sapiens

<400> SEQUENCE: 104
tttagccagt ggtggggttc a                                        21

<210> SEQ ID NO 105
<211> LENGTH: 20
<212> TYPE: DNA
```

-continued

```
<213> ORGANISM: Homo sapiens

<400> SEQUENCE: 105
gttcagcagg gtggcaacat                                                   20

<210> SEQ ID NO 106
<211> LENGTH: 21
<212> TYPE: DNA
<213> ORGANISM: Homo sapiens

<400> SEQUENCE: 106
gccagatggt tttcaacgac a                                                 21

<210> SEQ ID NO 107
<211> LENGTH: 26
<212> TYPE: PRT
<213> ORGANISM: Homo sapiens

<400> SEQUENCE: 107

Phe Leu Ile Val Leu Val Cys Leu Ile Phe Ser Val Leu Ser Thr Ile
  1               5                  10                  15

Glu Gln Tyr Ala Ala Leu Ala Thr Gly Thr
             20                  25

<210> SEQ ID NO 108
<211> LENGTH: 61
<212> TYPE: PRT
<213> ORGANISM: Homo sapiens

<400> SEQUENCE: 108

Leu Phe Trp Met Glu Ile Val Leu Val Val Phe Phe Gly Thr Glu Tyr
  1               5                  10                  15

Val Val Arg Leu Trp Ser Ala Gly Cys Arg Ser Lys Tyr Val Gly Leu
                 20                  25                  30

Trp Gly Arg Leu Arg Phe Ala Arg Lys Pro Ile Ser Ile Ile Asp Leu
             35                  40                  45

Ile Val Val Val Ala Ser Met Val Val Leu Cys Val Gly
         50                  55                  60

<210> SEQ ID NO 109
<211> LENGTH: 137
<212> TYPE: PRT
<213> ORGANISM: Homo sapiens

<400> SEQUENCE: 109

Ser Lys Gly Gln Val Phe Ala Thr Ser Ala Ile Arg Gly Ile Arg Phe
  1               5                  10                  15

Leu Gln Ile Leu Arg Met Leu His Val Asp Arg Gln Gly Gly Thr Trp
                 20                  25                  30

Arg Leu Leu Gly Ser Val Val Phe Ile His Arg Gln Glu Leu Ile Thr
             35                  40                  45

Thr Leu Tyr Ile Gly Phe Leu Gly Leu Ile Phe Ser Ser Tyr Phe Val
         50                  55                  60

Tyr Leu Ala Glu Lys Asp Ala Val Asn Glu Ser Gly Arg Val Glu Phe
 65                  70                  75                  80

Gly Ser Tyr Ala Asp Ala Leu Trp Trp Gly Val Val Thr Val Thr Thr
                 85                  90                  95

Ile Gly Tyr Gly Asp Lys Val Pro Gln Thr Trp Val Gly Lys Thr Ile
                100                 105                 110
```

```
Ala Ser Cys Phe Ser Val Phe Ala Ile Ser Phe Phe Ala Leu Pro Ala
        115                 120                 125

Gly Ile Leu Gly Ser Gly Phe Ala Leu
        130                 135

<210> SEQ ID NO 110
<211> LENGTH: 66
<212> TYPE: PRT
<213> ORGANISM: Drosophila melanogaster

<400> SEQUENCE: 110

Ile Leu Leu Ser Ile Val Ile Phe Cys Leu Glu Thr Leu Pro Glu Phe
  1               5                  10                  15

Lys His Tyr Lys Val Phe Asn Thr Thr Thr Asn Gly Thr Lys Ile Glu
             20                  25                  30

Glu Asp Glu Val Pro Asp Ile Thr Asp Pro Phe Phe Leu Ile Glu Thr
         35                  40                  45

Leu Cys Ile Ile Trp Phe Thr Phe Glu Leu Thr Val Arg Phe Leu Ala
     50                  55                  60

Cys Pro
 65

<210> SEQ ID NO 111
<211> LENGTH: 123
<212> TYPE: PRT
<213> ORGANISM: Drosophila melanogaster

<400> SEQUENCE: 111

Asn Lys Leu Asn Phe Cys Arg Asp Val Met Asn Val Ile Asp Ile Ile
  1               5                  10                  15

Ala Ile Ile Pro Tyr Phe Ile Thr Leu Ala Thr Val Ala Glu Glu
             20                  25                  30

Glu Asp Thr Leu Asn Leu Pro Lys Ala Pro Val Ser Pro Gln Asp Lys
         35                  40                  45

Ser Ser Asn Gln Ala Met Ser Leu Ala Ile Leu Arg Val Ile Arg Leu
     50                  55                  60

Val Arg Val Phe Arg Ile Phe Lys Leu Ser Arg His Ser Lys Gly Leu
 65                  70                  75                  80

Gln Ile Leu Gly Arg Thr Leu Lys Ala Ser Met Arg Glu Leu Gly Leu
                 85                  90                  95

Leu Ile Phe Phe Leu Phe Ile Gly Val Val Leu Phe Ser Ser Ala Val
            100                 105                 110

Tyr Phe Ala Glu Ala Gly Ser Glu Asn Ser Phe
        115                 120

<210> SEQ ID NO 112
<211> LENGTH: 58
<212> TYPE: PRT
<213> ORGANISM: Drosophila melanogaster

<400> SEQUENCE: 112

Phe Lys Ser Ile Pro Asp Ala Phe Trp Trp Ala Val Val Thr Met Thr
  1               5                  10                  15

Thr Val Gly Tyr Gly Asp Met Thr Pro Val Gly Phe Trp Gly Lys Ile
             20                  25                  30

Val Gly Ser Leu Cys Val Val Ala Gly Val Leu Thr Ile Ala Leu Pro
         35                  40                  45

Val Pro Val Ile Val Ser Asn Phe Asn Tyr
```

-continued

```
        50                  55

<210> SEQ ID NO 113
<211> LENGTH: 376
<212> TYPE: PRT
<213> ORGANISM: Xenopus laevis

<400> SEQUENCE: 113

Met Asn Glu Asn Ala Ile Asn Ser Leu Tyr Glu Ala Ile Pro Leu Pro
  1               5                  10                  15

Gln Asp Gly Ser Ser Asn Gly Gln Arg Gln Glu Asp Arg Gln Ala Asn
             20                  25                  30

Ser Phe Glu Leu Lys Arg Glu Thr Leu Val Ala Thr Asp Pro Pro Arg
         35                  40                  45

Pro Thr Ile Asn Leu Asp Pro Arg Val Ser Ile Tyr Ser Gly Arg Arg
     50                  55                  60

Pro Leu Phe Ser Arg Thr Asn Ile Gln Gly Arg Val Tyr Asn Phe Leu
 65                  70                  75                  80

Glu Arg Pro Thr Gly Trp Lys Cys Phe Val Tyr His Phe Thr Val Phe
                 85                  90                  95

Leu Ile Val Leu Ile Cys Leu Ile Phe Ser Val Leu Ser Thr Ile Gln
            100                 105                 110

Gln Tyr Asn Asn Leu Ala Thr Glu Thr Leu Phe Trp Met Glu Ile Val
        115                 120                 125

Leu Val Val Phe Phe Gly Ala Glu Tyr Val Val Arg Leu Trp Ser Ala
    130                 135                 140

Gly Cys Arg Ser Lys Tyr Val Gly Val Trp Gly Arg Leu Arg Phe Ala
145                 150                 155                 160

Arg Lys Pro Ile Ser Val Ile Asp Leu Ile Val Val Val Ala Ser Val
                165                 170                 175

Ile Val Leu Cys Val Gly Ser Asn Gly Gln Val Phe Ala Thr Ser Ala
            180                 185                 190

Ile Arg Gly Ile Arg Phe Leu Gln Ile Leu Arg Met Leu His Val Asp
        195                 200                 205

Arg Gln Gly Gly Thr Trp Arg Leu Leu Gly Ser Val Val Phe Ile His
    210                 215                 220

Arg Gln Glu Leu Ile Thr Thr Leu Tyr Ile Gly Phe Leu Gly Leu Ile
225                 230                 235                 240

Phe Ser Ser Tyr Phe Val Tyr Leu Ala Glu Lys Asp Ala Ile Asp Ser
                245                 250                 255

Ser Gly Glu Tyr Gln Phe Gly Ser Tyr Ala Asp Ala Leu Trp Trp Gly
            260                 265                 270

Val Val Thr Val Thr Thr Ile Gly Tyr Gly Asp Lys Val Pro Gln Thr
        275                 280                 285

Trp Ile Gly Lys Thr Ile Ala Ser Cys Phe Ser Val Phe Ala Ile Ser
    290                 295                 300

Phe Phe Ala Leu Pro Ala Gly Ile Leu Gly Ser Gly Phe Ala Leu Lys
305                 310                 315                 320

Val Gln Gln Lys Gln Arg Gln Lys His Phe Asn Arg Gln Ile Pro Ala
                325                 330                 335

Ala Ala Ser Leu Ile Gln Thr Ala Trp Arg Cys Tyr Ala Ala Glu Asn
            340                 345                 350

Pro Asp Ser Ala Thr Trp Lys Ile Tyr Ile Arg Lys Gln Ser Arg Asn
        355                 360                 365
```

-continued

```
His His Ile Met Ser Pro Ser Pro
    370             375

<210> SEQ ID NO 114
<211> LENGTH: 570
<212> TYPE: PRT
<213> ORGANISM: Homo sapiens

<400> SEQUENCE: 114

Gln Gly Arg Val Tyr Asn Phe Leu Glu Arg Pro Thr Gly Trp Lys Cys
 1               5                  10                  15

Phe Val Tyr His Phe Ala Val Phe Leu Ile Val Leu Val Cys Leu Ile
            20                  25                  30

Phe Ser Val Leu Ser Thr Ile Glu Gln Tyr Ala Ala Leu Ala Thr Gly
        35                  40                  45

Thr Leu Phe Trp Met Glu Ile Val Leu Val Val Phe Phe Gly Thr Glu
    50                  55                  60

Tyr Val Val Arg Leu Trp Ser Ala Gly Cys Arg Ser Lys Tyr Val Gly
65                  70                  75                  80

Leu Trp Gly Arg Leu Arg Phe Ala Arg Lys Pro Ile Ser Ile Ile Asp
                85                  90                  95

Leu Ile Val Val Val Ala Ser Met Val Val Leu Cys Val Gly Ser Lys
            100                 105                 110

Gly Gln Val Phe Ala Thr Ser Ala Ile Arg Gly Ile Arg Phe Leu Gln
        115                 120                 125

Ile Leu Arg Met Leu His Val Asp Arg Gln Gly Gly Thr Trp Arg Leu
    130                 135                 140

Leu Gly Ser Val Val Phe Ile His Arg Gln Glu Leu Ile Thr Thr Leu
145                 150                 155                 160

Tyr Ile Gly Phe Leu Gly Leu Ile Phe Ser Ser Tyr Phe Val Tyr Leu
                165                 170                 175

Ala Glu Lys Asp Ala Val Asn Glu Ser Gly Arg Val Glu Phe Gly Ser
            180                 185                 190

Tyr Ala Asp Ala Leu Trp Trp Gly Val Val Thr Val Thr Thr Ile Gly
        195                 200                 205

Tyr Gly Asp Lys Val Pro Gln Thr Trp Val Gly Lys Thr Ile Ala Ser
    210                 215                 220

Cys Phe Ser Val Phe Ala Ile Ser Phe Phe Ala Leu Pro Ala Gly Ile
225                 230                 235                 240

Leu Gly Ser Gly Phe Ala Leu Lys Val Gln Gln Lys Gln Arg Gln Lys
                245                 250                 255

His Phe Asn Arg Gln Ile Pro Ala Ala Ala Ser Leu Ile Gln Thr Ala
            260                 265                 270

Trp Arg Cys Tyr Ala Ala Glu Asn Pro Asp Ser Ser Thr Trp Lys Ile
        275                 280                 285

Tyr Ile Arg Lys Ala Pro Arg Ser His Thr Leu Leu Ser Pro Ser Pro
    290                 295                 300

Lys Pro Lys Lys Ser Val Val Lys Lys Lys Phe Lys Leu Asp
305                 310                 315                 320

Lys Asp Asn Gly Val Thr Pro Gly Glu Lys Met Leu Thr Val Pro His
                325                 330                 335

Ile Thr Cys Asp Pro Pro Glu Glu Arg Arg Leu Asp His Phe Ser Val
            340                 345                 350

Asp Gly Tyr Asp Ser Ser Val Arg Lys Ser Pro Thr Leu Leu Glu Val
        355                 360                 365
```

```
Ser Met Pro His Phe Met Arg Thr Asn Ser Phe Ala Glu Asp Leu Asp
    370             375             380

Leu Glu Gly Glu Thr Leu Leu Thr Pro Ile Thr His Ile Ser Gln Leu
385             390             395                     400

Arg Glu His His Arg Ala Thr Ile Lys Val Ile Arg Arg Met Gln Tyr
            405             410                     415

Phe Val Ala Lys Lys Phe Gln Gln Ala Arg Lys Pro Tyr Asp Val
            420             425             430

Arg Asp Val Ile Glu Gln Tyr Ser Gln Gly His Leu Asn Leu Met Arg
            435             440             445

Val Ile Lys Glu Leu Gln Arg Arg Leu Asp Gln Ser Ile Gly Lys Pro
    450             455             460

Ser Leu Phe Ile Ser Val Ser Glu Lys Ser Lys Asp Arg Gly Ser Asn
465             470             475             480

Thr Ile Gly Ala Arg Leu Asn Arg Val Glu Asp Lys Val Thr Gln Leu
            485             490             495

Asp Gln Arg Leu Ala Leu Ile Thr Asp Met Leu His Gln Leu Leu Ser
            500             505             510

Leu His Gly Gly Ser Thr Pro Gly Ser Gly Gly Pro Pro Arg Glu Gly
    515             520             525

Gly Ala His Ile Thr Gln Pro Cys Gly Ser Gly Gly Ser Val Asp Pro
    530             535             540

Glu Leu Phe Leu Pro Ser Asn Thr Leu Pro Thr Tyr Glu Gln Leu Thr
545             550             555             560

Val Pro Arg Arg Gly Pro Asp Glu Gly Ser
            565             570
```